US009777277B2

(12) United States Patent
Lau et al.

(10) Patent No.: US 9,777,277 B2
(45) Date of Patent: Oct. 3, 2017

(54) ORGANIC SMALL HAIRPIN RNAS

(71) Applicant: BRANDEIS UNIVERSITY, Waltham, MA (US)

(72) Inventors: Nelson Lau, Watertown, MA (US); Mei Zeng, Newton, MA (US); Suzanne Paradis, Lexington, MA (US); Marissa Kuzirian, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 14/892,629

(22) PCT Filed: Jan. 29, 2014

(86) PCT No.: PCT/US2014/013640
§ 371 (c)(1),
(2) Date: Nov. 20, 2015

(87) PCT Pub. No.: WO2014/193489
PCT Pub. Date: Dec. 4, 2014

(65) Prior Publication Data

US 2016/0177314 A1 Jun. 23, 2016

Related U.S. Application Data

(60) Provisional application No. 61/829,621, filed on May 31, 2013.

(51) Int. Cl.
*C07H 21/04* (2006.01)
*C12N 15/113* (2010.01)

(52) U.S. Cl.
CPC ........ *C12N 15/1137* (2013.01); *C12N 15/113* (2013.01); *C12N 2310/14* (2013.01); *C12N 2310/141* (2013.01); *C12N 2310/531* (2013.01); *C12N 2320/30* (2013.01)

(58) Field of Classification Search
None
See application file for complete search history.

(56) References Cited

U.S. PATENT DOCUMENTS

2005/0181382 A1 8/2005 Zamore et al.
2006/0218654 A1 9/2006 Seibler et al.
2012/0021516 A1 1/2012 Hannon et al.
2012/0183955 A1 7/2012 Rao

OTHER PUBLICATIONS

Zeng et al., "Organic Small Hairpin RNAs (OshR): A Do-It-Yourself Platform for Transgene-Based Gene Silencing," Methods 63:101-109 (2013).
International Search Report and Written Opinion for corresponding PCT/US2014/013640 (May 12, 2014).
International Preliminary Report on Patentability for corresponding PCT/US2014/013640 (Dec. 10, 2015).

*Primary Examiner* — Kimberly Chong
(74) *Attorney, Agent, or Firm* — LeClairRyan, a Professional Corporation

(57) ABSTRACT

Disclosed are improved shRNA molecules, termed "organic shRNA" (OshRNA), that incorporate certain structural features that increase the likelihood that the desired guide strand is produced while reducing accumulation of passenger strands that might contribute to off-target effects. Also provided herein are nucleic acids encoding OshRNAs, kits, cells, and transgenic animals comprising such nucleic acids, as well as methods of making and using OshRNAs and/or nucleic acids encoding OshRNAs.

58 Claims, 38 Drawing Sheets

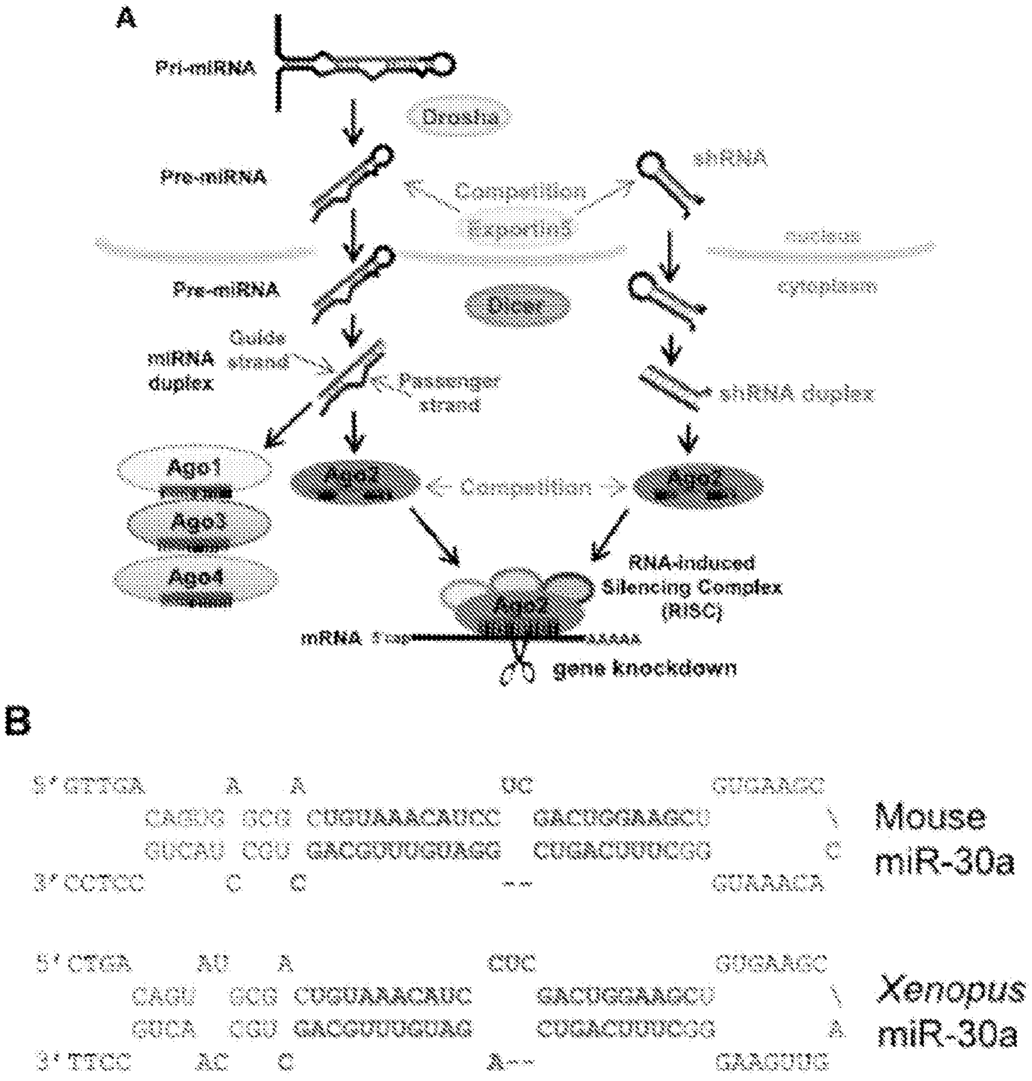
Figures 1A–B

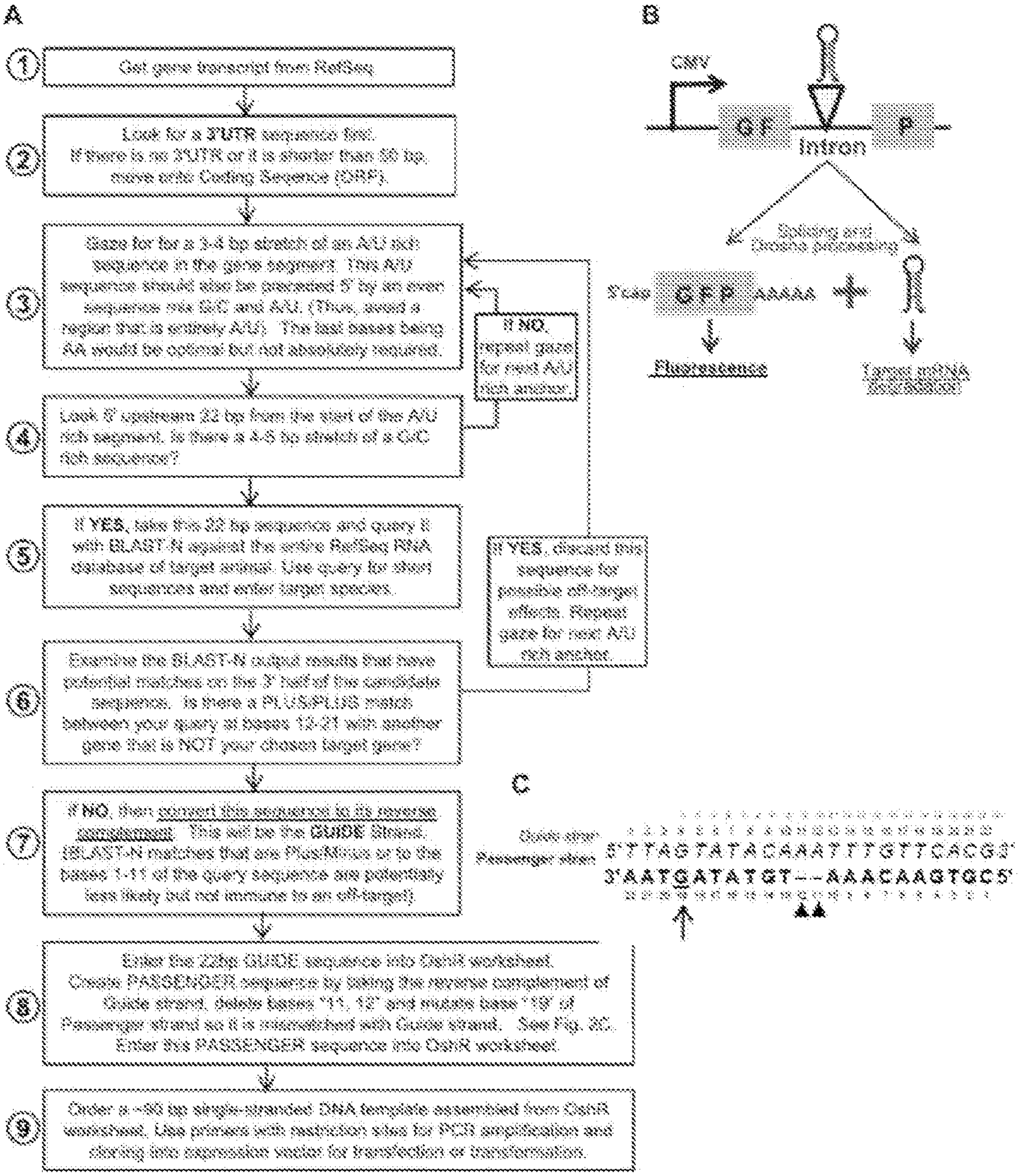
Figures 2A–C

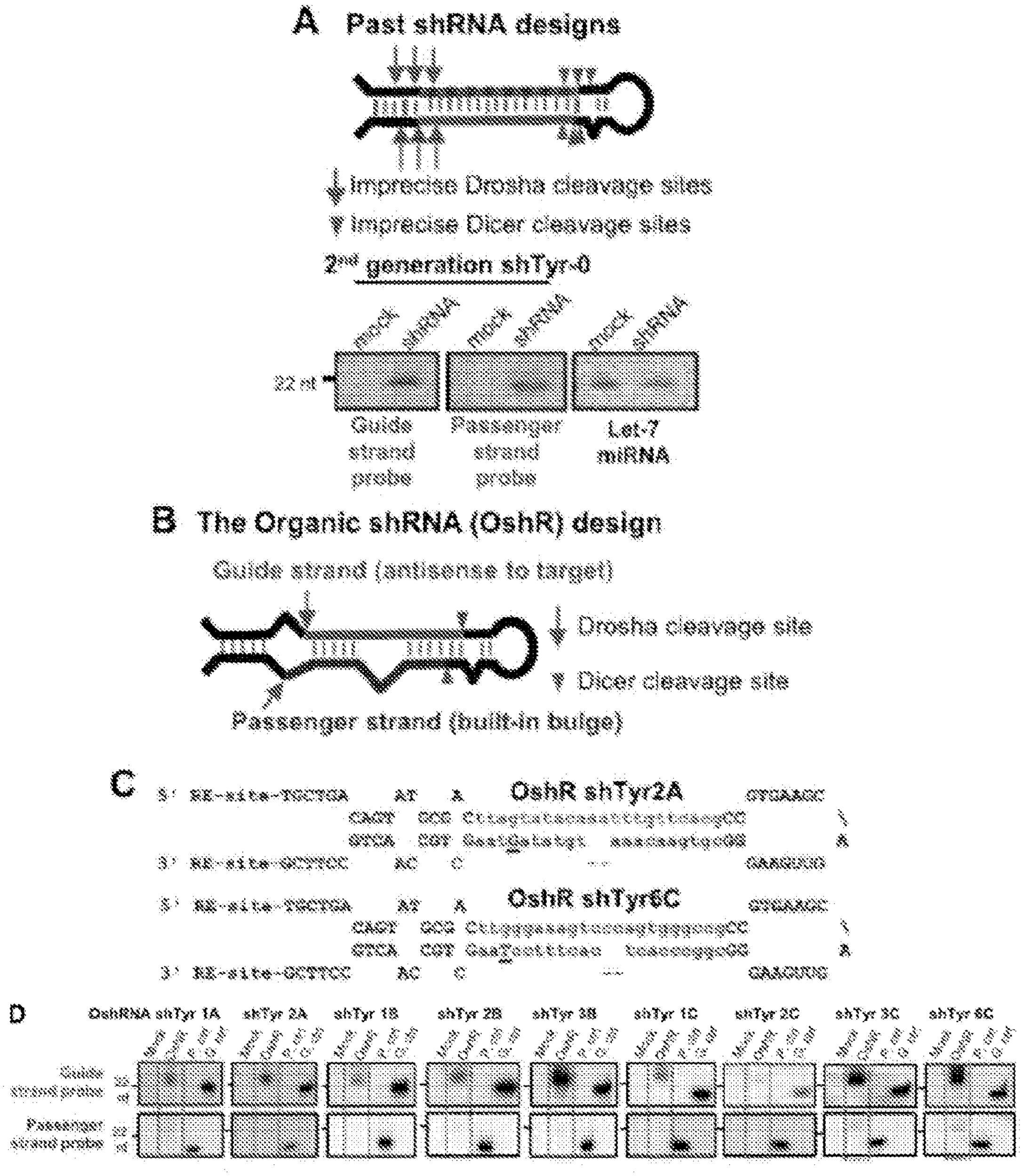
Figures 3A–D

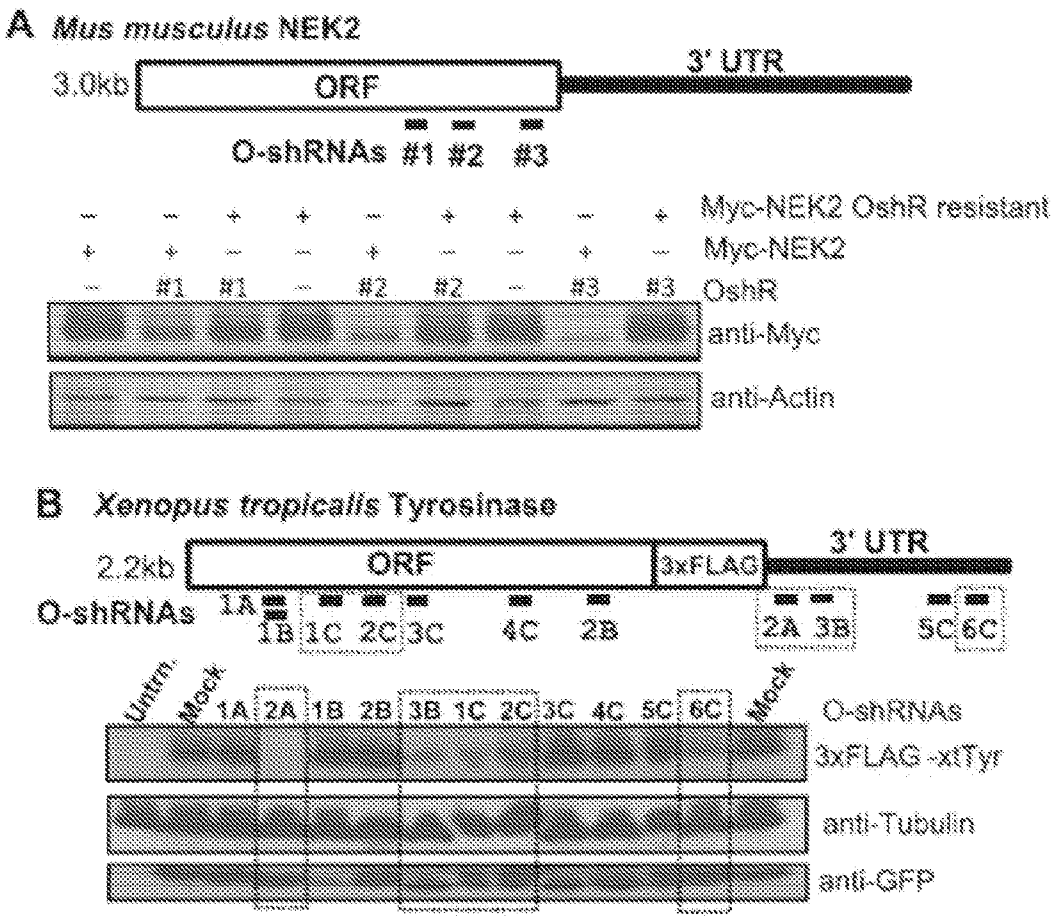
Figures 4A–B

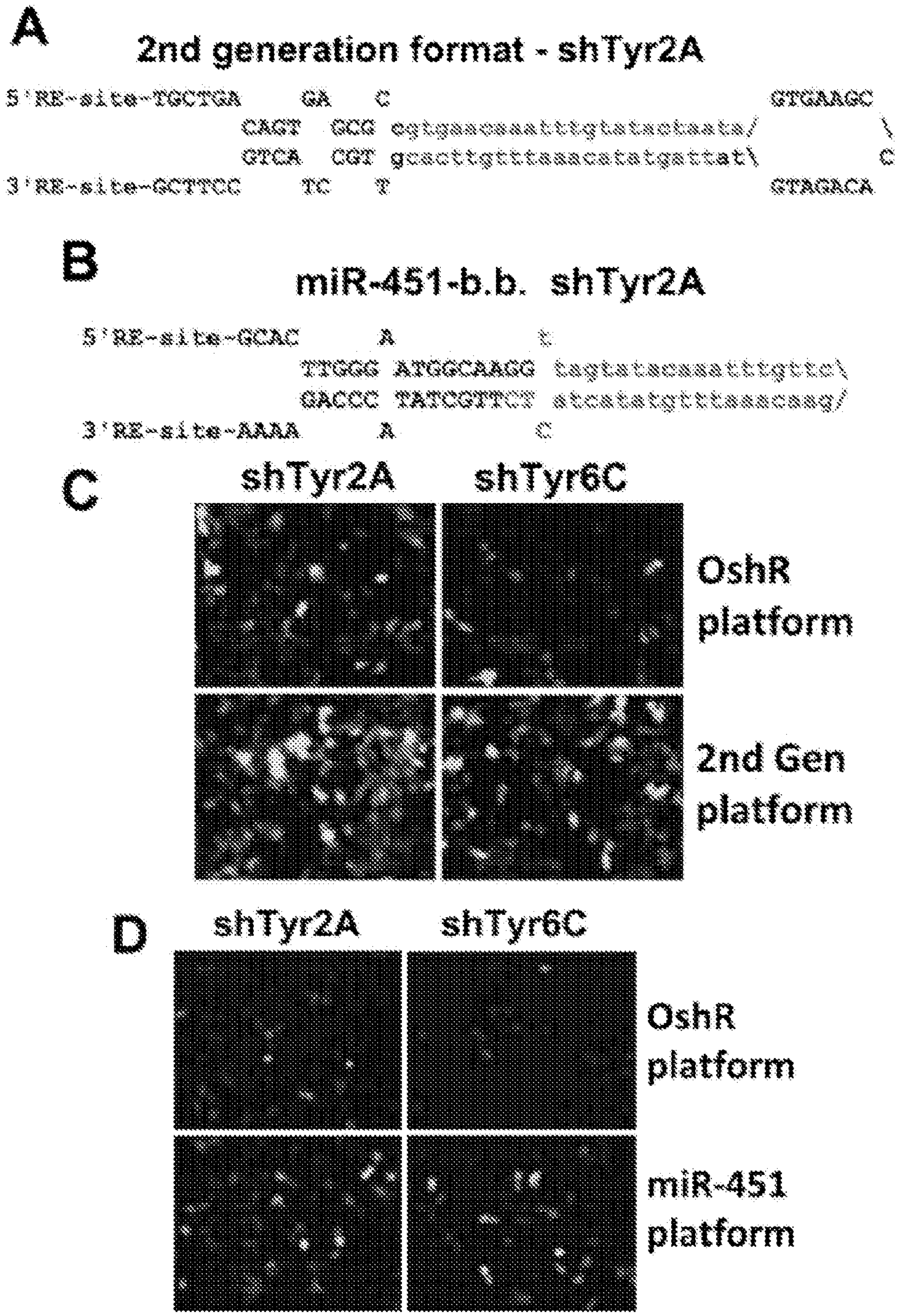
Figures 5A–D

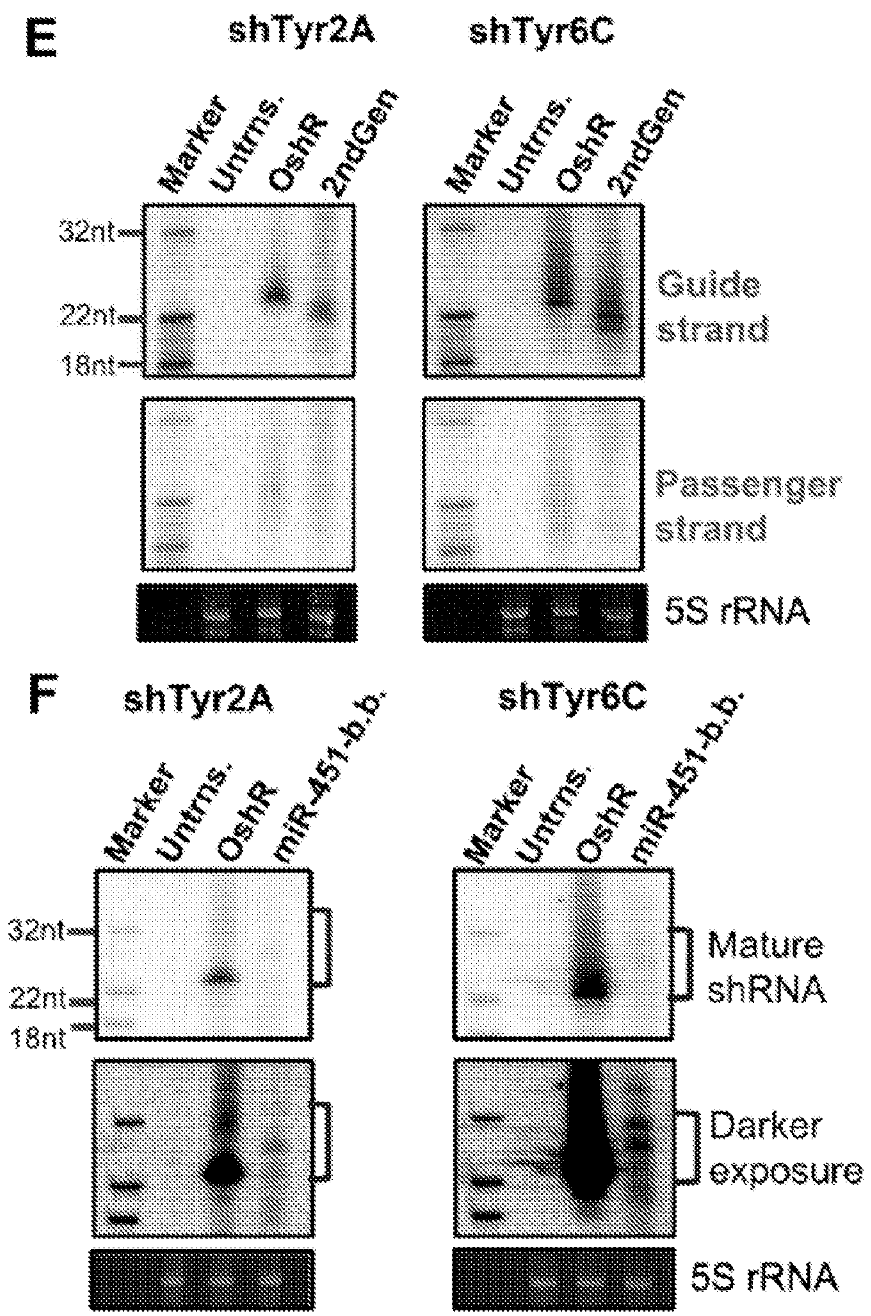
Figures 5E–F

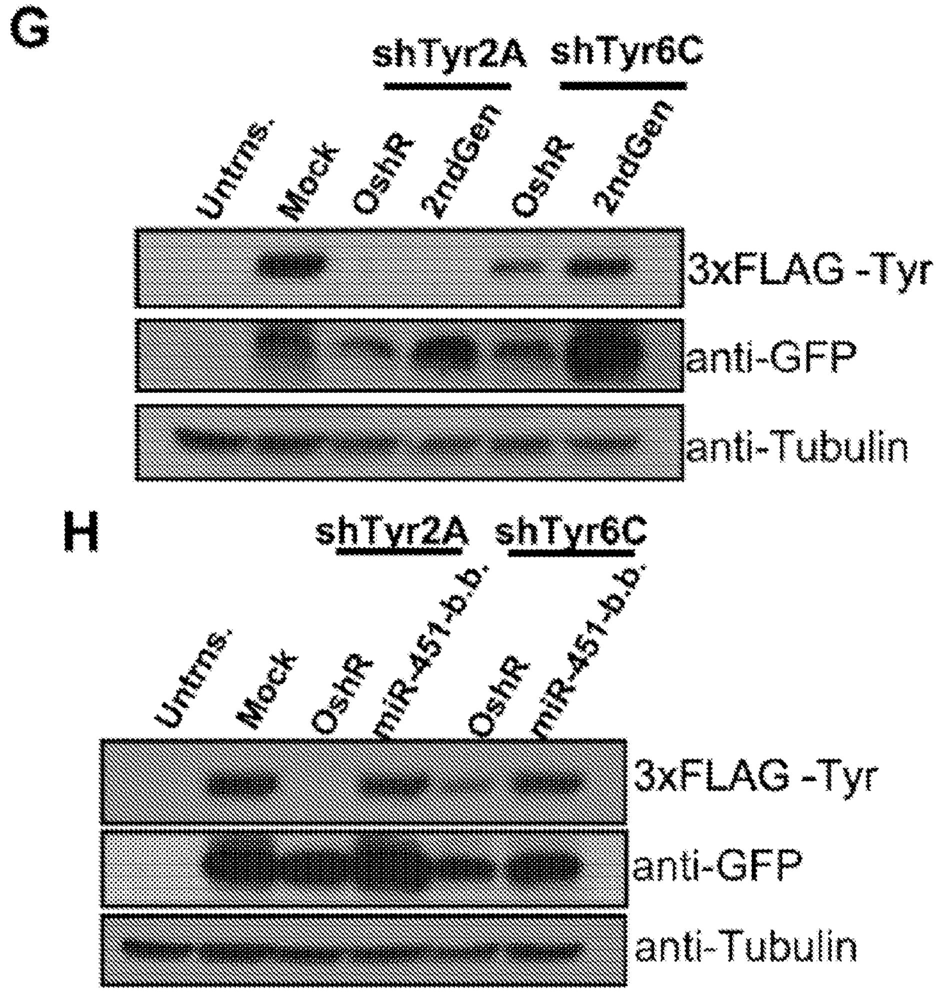
Figures 5G–H

ORGANIC shRNA DESIGNER EMBODIMENT

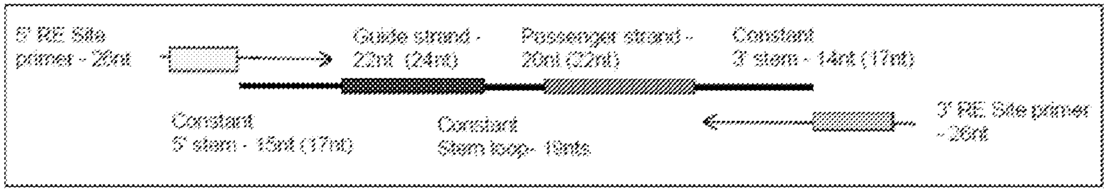

| | Length | Sequence | | Length | Sequence |
|---|---|---|---|---|---|
| 5RES - SphI | 26 | tttGCATGCtgctgacagtatgcgac | 3RES - SalI | 26 | aaaGTCGACcgaaggcagttggcagc |
| 5RES - SalI | 26 | tttGTCGACtgctgacagtatgcgac | 3RES - NsiI | 26 | aaaATGCATcgaaggcagttggcagc |
| 5RES - NsiI | 26 | tttATGCATtgctgacagtatgcgac | 3RES - MluI | 26 | aaaACGCGTcgaaggcagttggcagc |
| **Guide strand** | 22 | TTAGTATACAAATTTGTTCACG | 5Constant Stem | 15 | ctgacagtatgcgac |
| Pass. Strand Reversed | 22 | AATGATATGT--AAACAAGTGC | Constant Stem Loop | 19 | ccgtgaagcagttgaaggg |
| **Passenger strand** | 20 | CGTGAACAAATGTATAGTAA | 3Constant Stem | 17 | gctgccaactgccttcg |

| | Length | Sequence |
|---|---|---|
| **shRNA template oligo** | 93 | ctgacagtatgcgacTTAGTATACAAATTTGTTCACGccgtgaagcagttgaagggCGTGAACAAATGTATAGTAAgctgccaactgccttcg |
| SphI-SalI shRNA final | 113 | tttGCATGCtgctgacagtatgcgacTTAGTATACAAATTTGTTCACGccgtgaagcagttgaagggCGTGAACAAATGTATAGTAAgctgccaactgccttcgGTCGACttt |
| SphI-NsiI shRNA final | 113 | tttGCATGCtgctgacagtatgcgacTTAGTATACAAATTTGTTCACGccgtgaagcagttgaagggCGTGAACAAATGTATAGTAAgctgccaactgccttcgATGCATttt |
| SphI-MluI shRNA final | 113 | tttGCATGCtgctgacagtatgcgacTTAGTATACAAATTTGTTCACGccgtgaagcagttgaagggCGTGAACAAATGTATAGTAAgctgccaactgccttcgACGCGTttt |
| SalI-NsiI shRNA final | 113 | tttGTCGACtgctgacagtatgcgacTTAGTATACAAATTTGTTCACGccgtgaagcagttgaagggCGTGAACAAATGTATAGTAAgctgccaactgccttcgATGCATttt |
| SalI-MluI shRNA final | 113 | tttGTCGACtgctgacagtatgcgacTTAGTATACAAATTTGTTCACGccgtgaagcagttgaagggCGTGAACAAATGTATAGTAAgctgccaactgccttcgACGCGTttt |
| NsiI-MluI shRNA final | 113 | tttATGCATtgctgacagtatgcgacTTAGTATACAAATTTGTTCACGccgtgaagcagttgaagggCGTGAACAAATGTATAGTAAgctgccaactgccttcgACGCGTttt |

Sequencing primers for shRNA cloned into pGSH0

| | | |
|---|---|---|
| pGSH0_FW3 | 18 | ttgagggagacaccctcg |
| pGSH0_RV2 | 21 | TTTGTATAGTTCATCCATGCC |

Figure 6

Xt_Tyr_NM001103048_3xFlag, SEQ ID NO:30
GATCAGGCTCGGGGGGAGAGTGAGGAGCAGCATGGAAAGGAACATGGTCCCTCTGGCATTCTGCTGCCTGTTCTTCT
TCCTCCATGTTTGCAGGGGCCAGTTCCCAAGGGCATGTAGCACCGCAGAGTCGCTCCTGAGCAAGGAGTGTTGCCCT
GTGTGGTCTGGAGATGGGTCCTCTTGTGGCCAGCTATCAGGAAGGGGTGTCTGCCAGGATGTTGTCCTGACCAGCTC
TGCTACTGGCCCTCAGTTTCCATTCACTGGGGTTGACGATAGAGAGAACTGGCCAACAGTATTTTACAACAGGACGT
GCCAATGCCTTGGCAACTTCATGGGCTATAACTGTGCAGACTGCAAATTTGGCTTCAGAGGGCCAAACTGCACAGAG
AGAAGAACAATGATAAGAAAGGAGATATTCCGAATGAGCAGTGCTGAGAAGAGCAAATTCGTTGCCTACTTGAATTT
GGCTAAGCACACCACCAGCCGTGACTATGTCATAGTCACTGGCACCTACGCCCAGATGAATAATGGCTCCAACCCTA
TGTTTGCGGATATCAACGTGTATGACCTCTTTGTCTGGATGCATTACTATGCCTCCCGTGATGTCTTCATAGGAGAA
GATGCTCTCTGGAGAGACATTGACTTTGCCCATGAAGCTCCGGCTTTTGTGCCCTGGCACAGGTACTTCCTGCTGCA
CTGGGAACATGAGATTCAGAAACTCACAGGAGATGAGAATTTTACCATCCCTTTCTGGGATTGGAGAGATGCCCAAG
GTTGTGACATATGTACGGATGAGCTTCTGGGAGGGGTCCATCCCACCACCACCAGCCTATTAAGCCCGGCATCCTTC
TTCGCTTCATGGCAGATAGTATGCAGCCGCCCTGAGGAATACAATGCTCAGAGGATCCTATGCAATGGTACCGGGGA
AGGGCCCCTGTTCAGAAATCCTGGTGGCCACGATCGGAGCAGAACCCCCCGATTGCCTACAACAGCTGAAGTTGAGC
TGTGTCTGTCATTAACAAATTACGAAACGGAGCCCATGGATCGGTCGGCCAACTTTAGCTTCAGGAACACCCTAGAA
GGATTTGCAGATCCACGAACTGGGATAGCCAACCGCTCTCAAAGCAACATGCATAACTCGCTGCATGTGTTCCTCAA
CGGCTCCATGTCTTCCGTCCAAGGATCGGCCAATGACCCAGTTTTTGTCTTGCACCATGCTTTTGTCGACAGCATCT
TTGAGCAATGGCTCAGAAGACACGGAGCTTCAGTAGACATTTACCCAGAAGCCAATGCACCAATTGGCCACAATCGT
GGCTACTACATGGTTCCATTTATTCCTCTATACACAAATGGAGAATTCTTTGCCGCTTCTAGAGATCTTGGATATGA
TTACGATTATCTAGCAGAATCAGGTTCCATTGAAGACTTCCTTTTGCCCTACCTGGAGCAAGCGCGACAAATCTGGC
AGTGGCTGGTAGGCGCGGCTGTAGTTGGGGGACTCATTACTGCTGTGATTGCCACTATTGTCGGCTTGGCGTGCCGA
CGGAAAAGAAAATTCCCATCGGAGGAAACGCAGCCGCTGCTCATGGAAGCCGAAGATTATCAACCCACCTATCAGTC
TCACCTAGACTACAAAGACGATGACGACAAGGATTATAAGGATGACGATGATAAAGACTATAAAGATGATGATGACA
AATAGAACCCAAACACTAGCTAACTGTAACTAGCTACTCGTGAACAAATTTGTATACTAATTTTTATATTCGGTGGG
AGCCAACTGTGTGCTCCTTGTCTAATGTGGGAAGTAACTAGTTTTAACCCATTTTATTGCCTAAGACTTGGGTTCCA
GGGACCCCACAGAACAGCATCGACTACAGGCCCACTCTCCGTCCTTCTCTCACTTTATTCTCTTAATGACTTCTCCTT
ACATTCAACCTTCTTCCTTCCATTTCTCCTCTTTGTTCTCTTATAGAGATGGAGAATGACCATGGTCTCGGCATAAC
AGGCAAATGGTTGGGTGAGCAGGGGGTCCCACCTATACCTCGGCCCACTGGGACTTTCCCAATATCCCGGGGACCCA
GTCCGACACTGGCCTTGAGAGGAAAGTCATATTGCCCAGTCAAGTGGATAGAGGGTTAATCAAGTTGTGTAACACAC
AATGTACTTTTTATAAATATATATATAAAAAATATATATAATATGTATACTTCCCAATTGATATGCCCAGCCATCCC
TATATGTACAAAGCTGAAAGATTAAGGTTTAAATTCCATGTGATAAGGGCTACAAGTAAATAATATTTGGGAGAAAA
AAAAAAAAAAAAAAAAAAAAAAAAAAAAAAAAAAAAAAAAAAAA pGSH0, SEQ ID NO:31
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC

Figure 7

CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCCTTCGTCGACCTTCATGCATCTTCACGCGTAGCTTCCCTT
AATACAAGTGAGATGATGGCATACCATCTTTCGGGACTGAGTTGATGTGAAGAGTTTTTCTGTTTTGCTGATC
ACTTGTATATTATGTGACTAATAGTTAAAGTGCCAAAATAAAATGTGGGAACATTGAATGTGTATCCTACTTA
AGGGAATCGATTTCAAGGAGGACGGAAACATCCTCGGCCACAAGTTGGAATACAACTACAACTCCCACAACGT
ATACATCATGGCCGACAAGCAAAAGAACGGCATCAAAGCCAACTTCAAGACCCGCCACAACATCGAAGACGGC
GGCGTGCAACTCGCTGATCATTATCAACAAAATACTCCAATTGGCGATGACCCTGTCCTTTTACCAGACAACC
ATTACCTGTCCACACAATCTGCCCTTTCGAAAGATCCCAACGAAAAGAGAGACCACATGGTCCTTCTTGAGTT
TGTAACGGCTGCTGGGATTACACATGGCATGGATGAACTATACAAAAATCTAGAACTATAGTGAGTCGTATTA
CGTAGATCCAGACATGATAAGATACATTGATGAGTTTGGACAAACCACAACTAGAATGCAGTGAAAAAAATGC
TTTATTTGTGAAATTTGTGATGCTATTGCTTTATTTGTAACCATTATAAGCTGCAATAAACAAGTTAACAACA
ACAATTGCATTCATTTTATGTTTCAGGTTCAGGGGGAGGTGTGGGAGGTTTTTTAATTCGCGGCCGCCACCGC
GGTGGAGCTCCAGCTTTTGTTCCCTTTAGTGAGGGTTAATTGCGCGCATTACCCTGTTATCCCTACGCGCTTG
GCGTAATCATGGTCATAGCTGTTTCCTGTGTGAAATTGTTATCCGCTCACAATTCCACACAACATACGAGCCG
GAAGCATAAAGTGTAAAGCCTGGGGTGCCTAATGAGTGAGCTAACTCACATTAATTGCGTTGCGCTCACTGCC
CGCTTTCCAGTCGGGAAACCTGTCGTGCCAGCTGCATTAATGAATCGGCCAACGCGCGGGGAGAGGCGGTTTG
CGTATTGGGCGCTCTTCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGTATGTAGG
CGGTGCTACAGAGTTCTTGAAGTGGTGGCCTAACTACGGCTACACTAGAAGAACAGTATTTGGTATCTGCGCT
CTGCTGAAGCCAGTTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCCAGTGCTGCAATGATACCGCGA
GACCCACGCTCACCGGCTCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTCTGAGAATAG
TGTATGCGGCGACCGAGTTGCTCTTGCCCGGCGTCAATACGGGATAATACCGCGCCACATAGCAGAACTTTAA
AAGTGCTCATCATTGGAAAACGTTCTTCGGGGCGAAAACTCTCAAGGATCTTACCGCTGTTGAGATCCAGTTC
GATGTAACCCACTCGTGCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAATACTCATACTCTTCCTTT

Figure 7 (cont.)

TTCAATATTATTGAAGCATTTATCAGGGTTATTGTCTCATGAGCGGATACATATTTGAATGTATTTAGAAAAA
TAAACAAATAGGGGTTCCGCGCACATTTCCCCGAAAAGTGCCAC pGSH0_OshRNA_Tyr1A, SEQ ID NO:32
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCCTTCGTCGACTGCTGACAGTATGCGACTTAGTATACAAAT
TTGTTCACGCCGTGAAGCAGTTGAAGGGCGTGAACAAATGTATAGTAAGCTGCCAACTGCCTTCGATGCATCT
TCACGCGTAGCTTCCCTTAATACAAGTGAGATGATGGCATACCATCTTTCGGGACTGAGTTGATGTGAAGAGT
TTTTCTGTTTTGCTGATCACTTGTATATTATGTGACTAATAGTTAAAGTGCCAAAATAAAATGTGGGAACATT
GAATGTGTATCCTACTTAAGGGAATCGATTTCAAGGAGGACGGAAACATCCTCGGCCACAAGTTGGAATACAA
CTACAACTCCCACAACGTATACATCATGGCCGACAAGCAAAAGAACGGCATCAAAGCCAACTTCAAGACCCGC
CACAACATCGAAGACGGCGGCGTGCAACTCGCTGATCATTATCAACAAAATACTCCAATTGGCGATGACCCTG
TCCTTTTACCAGACAACCATTACCTGTCCACACAATCTGCCCTTTCGAAAGATCCCAACGAAAAGAGAGACCA
CATGGTCCTTCTTGAGTTTGTAACGGCTGCTGGGATTACACATGGCATGGATGAACTATACAAAAATCTAGAA
CTATAGTGAGTCGTATTACGTAGATCCAGACATGATAAGATACATTGATGAGTTTGGACAAACCACAACTAGA
ATGCAGTGAAAAAAATGCTTTATTTGTGAAATTTGTGATGCTATTGCTTTATTTGTAACCATTATAAGCTGCA
ATAAACAAGTTAACAACAACAATTGCATTCATTTTATGTTTCAGGTTCAGGGGGAGGTGTGGGAGGTTTTTTA
ATTCGCGGCCGCCACCGCGGTGGAGCTCCAGCTTTTGTTCCCTTTAGTGAGGGTTAATTGCGCGCATTACCCT
GTTATCCCTACGCGCTTGGCGTAATCATGGTCATAGCTGTTTCCTGTGTGAAATTGTTATCCGCTCACAATTC
CACACAACATACGAGCCGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCCAT

Figure 7 (cont.)

AGGCTCCGCCCCCCTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCCCGACCGCTGCGCCTTATCCGGTA
ACTATCGTCTTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTAAGGGATTTTGGTCATG
AGATTATCAAAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCATCTGGCCCCAGT
GCTGCAATGATACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAATACGGGATAATACCGCGC
CACATAGCAGAACTTTAAAAGTGCTCATCATTGGAAAACGTTCTTCGGGGCGAAAACTCTCAAGGATCTTACC
GCTGTTGAGATCCAGTTCGATGTAACCCACTCGTGCACCCAACTGATCTTCAGCATCTTTTACTTTCACCAGC
GTTTCTGGGTGAGCAAAAACAGGAAGGCAAAATGCCGCAAAAAAGGGAATAAGGGCGACACGGAAATGTTGAA
TACTCATACTCTTCCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCCAC pGSH0_OshRNA_Tyr2A, SEQ ID NO:33
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC

Figure 7 (cont.)

CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCCTTCGTCGACTGCTGACAGTATGCGACTTAGTATACAAAT
TTGTTCACGCCGTGAAGCAGTTGAAGGGCGTGAACAAATGTATAGTAAGCTGCCAACTGCCTTCGATGCATCT
TCACGCGTAGCTTCCCTTAATACAAGTGAGATGATGGCATACCATCTTTCGGGACTGAGTTGATGTGAAGAGT
TTTTCTGTTTTGCTGATCACTTGTATATTATGTGACTAATAGTTAAAGTGCCAAAATAAAATGTGGGAACATT
GAATGTGTATCCTACTTAAGGGAATCGATTTCAAGGAGGACGGAAACATCCTCGGCCACAAGTTGGAATACAA
CTACAACTCCCACAACGTATACATCATGGCCGACAAGCAAAAGAACGGCATCAAAGCCAACTTCAAGACCCGC
CACAACATCGAAGACGGCGGCGTGCAACTCGCTGATCATTATCAACAAAATACTCCAATTGGCGATGACCCTG
TCCTTTTACCAGACAACCATTACCTGTCCACACAATCTGCCCTTTCGAAAGATCCCAACGAAAAGAGAGACCA
CATGGTCCTTCTTGAGTTTGTAACGGCTGCTGGGATTACACATGGCATGGATGAACTATACAAAAATCTAGAA
CTATAGTGAGTCGTATTACGTAGATCCAGACATGATAAGATACATTGATGAGTTTGGACAAACCACAACTAGA
ATGCAGTGAAAAAAATGCTTTATTTGTGAAATTTGTGATGCTATTGCTTTATTTGTAACCATTATAAGCTGCA
ATAAACAAGTTAACAACAACAATTGCATTCATTTTATGTTTCAGGTTCAGGGGGAGGTGTGGGAGGTTTTTTA
ATTCGCGGCCGCCACCGCGGTGGAGCTCCAGCTTTTGTTCCCTTTAGTGAGGGTTAATTGCGCGCATTACCCT
GTTATCCCTACGCGCTTGGCGTAATCATGGTCATAGCTGTTTCCTGTGTGAAATTGTTATCCGCTCACAATTC
CACACAACATACGAGCCGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCCCGACCGCTGCGCCTTATCCGGTA
ACTATCGTCTTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTAAGGGATTTTGGTCATG
AGATTATCAAAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCATCTGGCCCCAGT
GCTGCAATGATACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAATACGGGATAATACCGCGC
CACATAGCAGAACTTTAAAAGTGCTCATCATTGGAAAACGTTCTTCGGGGCGAAAACTCTCAAGGATCTTACC
GCTGTTGAGATCCAGTTCGATGTAACCCACTCGTGCACCCAACTGATCTTCAGCATCTTTTACTTTCACCAGC
GTTTCTGGGTGAGCAAAAACAGGAAGGCAAAATGCCGCAAAAAAGGGAATAAGGGCGACACGGAAATGTTGAA
TACTCATACTCTTCCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCCAC pGSH0_OshRNA_Tyr1B, SEQ ID NO:34
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA

Figure 7 (cont.)

AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTATGCGACTTATTCATCTGGGCGTAGGTGCC
TGTGAAGCAGTTGAAGGGGGACCTACGAAGATGAACAAGCTGCCAACTGCCTTCGATGCATCTTCACGCGTAG
CTTCCCTTAATACAAGTGAGATGATGGCATACCATCTTTCGGGACTGAGTTGATGTGAAGAGTTTTTCTGTTT
TGCTGATCACTTGTATATTATGTGACTAATAGTTAAAGTGCCAAAATAAAATGTGGGAACATTGAATGTGTAT
CCTACTTAAGGGAATCGATTTCAAGGAGGACGGAAACATCCTCGGCCACAAGTTGGAATACAACTACAACTCC
CACAACGTATACATCATGGCCGACAAGCAAAAGAACGGCATCAAAGCCAACTTCAAGACCCGCCACAACATCG
AAGACGGCGGCGTGCAACTCGCTGATCATTATCAACAAAATACTCCAATTGGCGATGACCCTGTCCTTTTACC
AGACAACCATTACCTGTCCACACAATCTGCCCTTTCGAAAGATCCCAACGAAAAGAGAGACCACATGGTCCTT
CTTGAGTTTGTAACGGCTGCTGGGATTACACATGGCATGGATGAACTATACAAAAATCTAGAACTATAGTGAG
TCGTATTACGTAGATCCAGACATGATAAGATACATTGATGAGTTTGGACAAACCACAACTAGAATGCAGTGAA
AAAAATGCTTTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAATTCGCGGCC
GCCACCGCGGTGGAGCTCCAGCTTTTGTTCCCTTTAGTGAGGGTTAATTGCGCGCATTACCCTGTTATCCCTA
CGCGCTTGGCGTAATCATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAA

Figure 7 (cont.)

AAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC pGSH0_OshRNA_Tyr2B, SEQ ID NO:35

CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTATGCGACTTGTGGCCAATTGGTGCATTGGC
TGTGAAGCAGTTGAAGGGCCAATGCACCTTGGCCATAAGCTGCCAACTGCCTTCGATGCATCTTCACGCGTAG
CTTCCCTTAATACAAGTGAGATGATGGCATACCATCTTTCGGGACTGAGTTGATGTGAAGAGTTTTTCTGTTT
TGCTGATCACTTGTATATTATGTGACTAATAGTTAAAGTGCCAAAATAAAATGTGGGAACATTGAATGTGTAT
CCTACTTAAGGGAATCGATTTCAAGGAGGACGGAAACATCCTCGGCCACAAGTTGGAATACAACTACAACTCC
CACAACGTATACATCATGGCCGACAAGCAAAAGAACGGCATCAAAGCCAACTTCAAGACCCGCCACAACATCG

Figure 7 (cont.)

AAGACGGCGGCGTGCAACTCGCTGATCATTATCAACAAAATACTCCAATTGGCGATGACCCTGTCCTTTTACC
AGACAACCATTACCTGTCCACACAATCTGCCCTTTCGAAAGATCCCAACGAAAAGAGAGACCACATGGTCCTT
CTTGAGTTTGTAACGGCTGCTGGGATTACACATGGCATGGATGAACTATACAAAAATCTAGAACTATAGTGAG
TCGTATTACGTAGATCCAGACATGATAAGATACATTGATGAGTTTGGACAAACCACAACTAGAATGCAGTGAA
AAAAATGCTTTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAATTCGCGGCC
GCCACCGCGGTGGAGCTCCAGCTTTTGTTCCCTTTAGTGAGGGTTAATTGCGCGCATTACCCTGTTATCCCTA
CGCGCTTGGCGTAATCATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC pGSH0_OshRNA_Tyr3B, SEQ ID NO:36
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA

Figure 7 (cont.)

TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTATGCGACTTCCCACATTAGACAAGGAGCAC
TGTGAAGCAGTTGAAGGGTGCTCCTTGAAATGTGGAAAGCTGCCAACTGCCTTCGATGCATCTTCACGCGTAG
CTTCCCTTAATACAAGTGAGATGATGGCATACCATCTTTCGGGACTGAGTTGATGTGAAGAGTTTTTCTGTTT
TGCTGATCACTTGTATATTATGTGACTAATAGTTAAAGTGCCAAAATAAAATGTGGGAACATTGAATGTGTAT
CCTACTTAAGGGAATCGATTTCAAGGAGGACGGAAACATCCTCGGCCACAAGTTGGAATACAACTACAACTCC
CACAACGTATACATCATGGCCGACAAGCAAAAGAACGGCATCAAAGCCAACTTCAAGACCCGCCACAACATCG
AAGACGGCGGCGTGCAACTCGCTGATCATTATCAACAAAATACTCCAATTGGCGATGACCCTGTCCTTTTACC
AGACAACCATTACCTGTCCACACAATCTGCCCTTTCGAAAGATCCCAACGAAAAGAGAGACCACATGGTCCTT
CTTGAGTTTGTAACGGCTGCTGGGATTACACATGGCATGGATGAACTATACAAAAATCTAGAACTATAGTGAG
TCGTATTACGTAGATCCAGACATGATAAGATACATTGATGAGTTTGGACAAACCACAACTAGAATGCAGTGAA
AAAAATGCTTTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAATTCGCGGCC
GCCACCGCGGTGGAGCTCCAGCTTTTGTTCCCTTTAGTGAGGGTTAATTGCGCGCATTACCCTGTTATCCCTA
CGCGCTTGGCGTAATCATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCT

Figure 7 (cont.)

GAGAATAGTGTATGCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC pGSH0_OshRNA_Tyr1C, SEQ ID NO:37

CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTATGCGACTAATGCATCCAGACAAAGAGGCT
GTGAAGCAGTTGAAGGGCCTCTTTGAGGATGCACTAGCTGCCAACTGCCTTCGACGCGTAGCTTCCCTTAATA
CAAGTGAGATGATGGCATACCATCTTTCGGGACTGAGTTGATGTGAAGAGTTTTTCTGTTTTGCTGATCACTT
GTATATTATGTGACTAATAGTTAAAGTGCCAAAATAAAATGTGGGAACATTGAATGTGTATCCTACTTAAGGG
AATCGATTTCAAGGAGGACGGAAACATCCTCGGCCACAAGTTGGAATACAACTACAACTCCCACAACGTATAC
ATCATGGCCGACAAGCAAAAGAACGGCATCAAAGCCAACTTCAAGACCCGCCACAACATCGAAGACGGCGGCG
TGCAACTCGCTGATCATTATCAACAAAATACTCCAATTGGCGATGACCCTGTCCTTTTACCAGACAACCATTA
CCTGTCCACACAATCTGCCCTTTCGAAAGATCCCAACGAAAAGAGAGACCACATGGTCCTTCTTGAGTTTGTA
ACGGCTGCTGGGATTACACATGGCATGGATGAACTATACAAAAATCTAGAACTATAGTGAGTCGTATTACGTA
GATCCAGACATGATAAGATACATTGATGAGTTTGGACAAACCACAACTAGAATGCAGTGAAAAAAATGCTTTA
TTTGTGAAATTTGTGATGCTATTGCTTTATTTGTAACCATTATAAGCTGCAATAAACAAGTTAACAACAACAA
TTGCATTCATTTTATGTTTCAGGTTCAGGGGGAGGTGTGGGAGGTTTTTTAATTCGCGGCCGCCACCGCGGTG
GAGCTCCAGCTTTTGTTCCCTTTAGTGAGGGTTAATTGCGCGCATTACCCTGTTATCCCTACGCGCTTGGCGT
AATCATGGTCATAGCTGTTTCCTGTGTGAAATTGTTATCCGCTCACAATTCCACACAACATACGAGCCGGAAG
CATAAAGTGTAAAGCCTGGGGTGCCTAATGAGTGAGCTAACTCACATTAATTGCGTTGCGCTCACTGCCCGCT

Figure 7 (cont.)

TTCCAGTCGGGAAACCTGTCGTGCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTCGGCTGCGGCGAGCGGTATCAGC
TCACTCAAAGGCGGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGAGTCCAACCC
GGTAAGACACGACTTATCGCCACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGAACAGTATTTGGTATCTGCGCTCTGC
TGAAGCCAGTTACCTTCGGAAAAAGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCATAGTTGCCTGACTC
CCCGTCGTGTAGATAACTACGATACGGGAGGGCTTACCATCTGGCCCCAGTGCTGCAATGATACCGCGAGACC
CACGCTCACCGGCTCCAGATTTATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTATGGCTTCATTCAGCT
CCGGTTCCCAACGATCAAGGCGAGTTACATGATCCCCCATGTTGTGCAAAAAAGCGGTTAGCTCCTTCGGTCC
TCCGATCGTTGTCAGAAGTAAGTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGCCACATAGCAGAACTTTAAAAGT
GCTCATCATTGGAAAACGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACTCATACTCTTCCTTTTTCA
ATATTATTGAAGCATTTATCAGGGTTATTGTCTCATGAGCGGATACATATTTGAATGTATTTAGAAAAATAAA
CAAATAGGGGTTCCGCGCACATTTCCCCGAAAAGTGCCAC pGSH0_OshRNA_Tyr2C, SEQ ID NO:38
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC

Figure 7 (cont.)

GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTATGCGACTCAATGTCTCTCCAGAGAGCATC
TGTGAAGCAGTTGAAGGGATGCTCTCTCGAGACATCGAGCTGCCAACTGCCTTCGATGCATCTTCACGCGTAG
CTTCCCTTAATACAAGTGAGATGATGGCATACCATCTTTCGGGACTGAGTTGATGTGAAGAGTTTTTCTGTTT
TGCTGATCACTTGTATATTATGTGACTAATAGTTAAAGTGCCAAAATAAAATGTGGGAACATTGAATGTGTAT
CCTACTTAAGGGAATCGATTTCAAGGAGGACGGAAACATCCTCGGCCACAAGTTGGAATACAACTACAACTCC
CACAACGTATACATCATGGCCGACAAGCAAAAGAACGGCATCAAAGCCAACTTCAAGACCCGCCACAACATCG
AAGACGGCGGCGTGCAACTCGCTGATCATTATCAACAAAATACTCCAATTGGCGATGACCCTGTCCTTTTACC
AGACAACCATTACCTGTCCACACAATCTGCCCTTTCGAAAGATCCCAACGAAAAGAGAGACCACATGGTCCTT
CTTGAGTTTGTAACGGCTGCTGGGATTACACATGGCATGGATGAACTATACAAAAATCTAGAACTATAGTGAG
TCGTATTACGTAGATCCAGACATGATAAGATACATTGATGAGTTTGGACAAACCACAACTAGAATGCAGTGAA
AAAAATGCTTTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAATTCGCGGCC
GCCACCGCGGTGGAGCTCCAGCTTTTGTTCCCTTTAGTGAGGGTTAATTGCGCGCATTACCCTGTTATCCCTA
CGCGCTTGGCGTAATCATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC

Figure 7 (cont.)

pGSH0_OshRNA_Tyr3C, SEQ ID NO:39

CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTATGCGACTGTTCCCAGTGCAGCAGGAAGCT
GTGAAGCAGTTGAAGGGCTTCCTGCAACTGGGACCAGCTGCCAACTGCCTTCGATGCATCTTCACGCGTAGCT
TCCCTTAATACAAGTGAGATGATGGCATACCATCTTTCGGGACTGAGTTGATGTGAAGAGTTTTTCTGTTTTG
CTGATCACTTGTATATTATGTGACTAATAGTTAAAGTGCCAAAATAAAATGTGGGAACATTGAATGTGTATCC
TACTTAAGGGAATCGATTTCAAGGAGGACGGAAACATCCTCGGCCACAAGTTGGAATACAACTACAACTCCCA
CAACGTATACATCATGGCCGACAAGCAAAAGAACGGCATCAAAGCCAACTTCAAGACCCGCCACAACATCGAA
GACGGCGGCGTGCAACTCGCTGATCATTATCAACAAAATACTCCAATTGGCGATGACCCTGTCCTTTTACCAG
ACAACCATTACCTGTCCACACAATCTGCCCTTTCGAAAGATCCCAACGAAAAGAGAGACCACATGGTCCTTCT
TGAGTTTGTAACGGCTGCTGGGATTACACATGGCATGGATGAACTATACAAAAATCTAGAACTATAGTGAGTC
GTATTACGTAGATCCAGACATGATAAGATACATTGATGAGTTTGGACAAACCACAACTAGAATGCAGTGAAAA
AAATGCTTTATTTGTGAAATTTGTGATGCTATTGCTTTATTTGTAACCATTATAAGCTGCAATAAACAAGTTA
ACAACAACAATTGCATTCATTTTATGTTTCAGGTTCAGGGGGAGGTGTGGGAGGTTTTTTAATTCGCGGCCGC
CACCGCGGTGGAGCTCCAGCTTTTGTTCCCTTTAGTGAGGGTTAATTGCGCGCATTACCCTGTTATCCCTACG
CGCTTGGCGTAATCATGGTCATAGCTGTTTCCTGTGTGAAATTGTTATCCGCTCACAATTCCACACAACATAC
GAGCCGGAAGCATAAAGTGTAAAGCCTGGGGTGCCTAATGAGTGAGCTAACTCACATTAATTGCGTTGCGCTC
ACTGCCCGCTTTCCAGTCGGGAAACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGGATACCTGTCCGCCTT
TCTCCCTTCGGGAAGCGTGGCGCTTTCTCATAGCTCACGCTGTAGGTATCTCAGTTCGGTGTAGGTCGTTCGC

Figure 7 (cont.)

TCCAAGCTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAAGATCCTTTGAT
CTTTTCTACGGGGTCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCATAGT
TGCCTGACTCCCCGTCGTGTAGATAACTACGATACGGGAGGGCTTACCATCTGGCCCCAGTGCTGCAATGATA
CCGCGAGACCCACGCTCACCGGCTCCAGATTTATCAGCAATAAACCAGCCAGCCGGAAGGGCCGAGCGCAGAA
GTGGTCCTGCAACTTTATCCGCCTCCATCCAGTCTATTAATTGTTGCCGGGAAGCTAGAGTAAGTAGTTCGCC
AGTTAATAGTTTGCGCAACGTTGTTGCCATTGCTACAGGCATCGTGGTGTCACGCTCGTCGTTTGGTATGGCT
TCATTCAGCTCCGGTTCCCAACGATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACTGCA
TAATTCTCTTACTGTCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGA
GCAAAAACAGGAAGGCAAAATGCCGCAAAAAAGGGAATAAGGGCGACACGGAAATGTTGAATACTCATACTCT
TCCTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCAC pGSH0_OshRNA_Tyr4C, SEQ ID NO:40
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC

Figure 7 (cont.)

ACATCTGAGTAGGTAGAATAAAAAGCTGCATGCTGCTGACAGTATGCGACTAATCCTTCTAGGGTGTTCCTGC
TGTGAAGCAGTTGAAGGGCAGGAACACCAGAAGGAGTAGCTGCCAACTGCCTTCGATGCATCTTCACGCGTAG
CTTCCCTTAATACAAGTGAGATGATGGCATACCATCTTTCGGGACTGAGTTGATGTGAAGAGTTTTTCTGTTT
TGCTGATCACTTGTATATTATGTGACTAATAGTTAAAGTGCCAAAATAAAATGTGGGAACATTGAATGTGTAT
CCTACTTAAGGGAATCGATTTCAAGGAGGACGGAAACATCCTCGGCCACAAGTTGGAATACAACTACAACTCC
CACAACGTATACATCATGGCCGACAAGCAAAAGAACGGCATCAAAGCCAACTTCAAGACCCGCCACAACATCG
AAGACGGCGGCGTGCAACTCGCTGATCATTATCAACAAAATACTCCAATTGGCGATGACCCTGTCCTTTTACC
AGACAACCATTACCTGTCCACACAATCTGCCCTTTCGAAAGATCCCAACGAAAAGAGAGACCACATGGTCCTT
CTTGAGTTTGTAACGGCTGCTGGGATTACACATGGCATGGATGAACTATACAAAAATCTAGAACTATAGTGAG
TCGTATTACGTAGATCCAGACATGATAAGATACATTGATGAGTTTGGACAAACCACAACTAGAATGCAGTGAA
AAAAATGCTTTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAATTCGCGGCC
GCCACCGCGGTGGAGCTCCAGCTTTTGTTCCCTTTAGTGAGGGTTAATTGCGCGCATTACCCTGTTATCCCTA
CGCGCTTGGCGTAATCATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC pGSH0_OshRNA_Tyr5C, SEQ ID NO:41
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT

Figure 7 (cont.)

CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTATGCGACTAGGTGGGACCCCCTGCTCACCC
TGTGAAGCAGTTGAAGGGGGTGAGCAGAGTCCCACTTAGCTGCCAACTGCCTTCGATGCATCTTCACGCGTAG
CTTCCCTTAATACAAGTGAGATGATGGCATACCATCTTTCGGGACTGAGTTGATGTGAAGAGTTTTTCTGTTT
TGCTGATCACTTGTATATTATGTGACTAATAGTTAAAGTGCCAAAATAAAATGTGGGAACATTGAATGTGTAT
CCTACTTAAGGGAATCGATTTCAAGGAGGACGGAAACATCCTCGGCCACAAGTTGGAATACAACTACAACTCC
CACAACGTATACATCATGGCCGACAAGCAAAAGAACGGCATCAAAGCCAACTTCAAGACCCGCCACAACATCG
AAGACGGCGGCGTGCAACTCGCTGATCATTATCAACAAAATACTCCAATTGGCGATGACCCTGTCCTTTTACC
AGACAACCATTACCTGTCCACACAATCTGCCCTTTCGAAAGATCCCAACGAAAAGAGAGACCACATGGTCCTT
CTTGAGTTTGTAACGGCTGCTGGGATTACACATGGCATGGATGAACTATACAAAAATCTAGAACTATAGTGAG
TCGTATTACGTAGATCCAGACATGATAAGATACATTGATGAGTTTGGACAAACCACAACTAGAATGCAGTGAA
AAAAATGCTTTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAATTCGCGGCC
GCCACCGCGGTGGAGCTCCAGCTTTTGTTCCCTTTAGTGAGGGTTAATTGCGCGCATTACCCTGTTATCCCTA
CGCGCTTGGCGTAATCATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGA

Figure 7 (cont.)

TACCGCGAGACCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC pGSH0_OshRNA_Tyr6C, SEQ ID NO:42
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTATGCGACTTGGGAAAGTCCCAGTGGGCCGC
TGTGAAGCAGTTGAAGGGCGGCCCACTCACTTTCCTAAGCTGCCAACTGCCTTCGATGCATCTTCACGCGTAG
CTTCCCTTAATACAAGTGAGATGATGGCATACCATCTTTCGGGACTGAGTTGATGTGAAGAGTTTTTCTGTTT
TGCTGATCACTTGTATATTATGTGACTAATAGTTAAAGTGCCAAAATAAAATGTGGGAACATTGAATGTGTAT
CCTACTTAAGGGAATCGATTTCAAGGAGGACGGAAACATCCTCGGCCACAAGTTGGAATACAACTACAACTCC
CACAACGTATACATCATGGCCGACAAGCAAAAGAACGGCATCAAAGCCAACTTCAAGACCCGCCACAACATCG
AAGACGGCGGCGTGCAACTCGCTGATCATTATCAACAAAATACTCCAATTGGCGATGACCCTGTCCTTTTACC
AGACAACCATTACCTGTCCACACAATCTGCCCTTTCGAAAGATCCCAACGAAAAGAGAGACCACATGGTCCTT
CTTGAGTTTGTAACGGCTGCTGGGATTACACATGGCATGGATGAACTATACAAAAAATCTAGAACTATAGTGAG

Figure 7 (cont.)

TCGTATTACGTAGATCCAGACATGATAAGATACATTGATGAGTTTGGACAAACCACAACTAGAATGCAGTGAA
AAAAATGCTTTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAATTCGCGGCC
GCCACCGCGGTGGAGCTCCAGCTTTTGTTCCCTTTAGTGAGGGTTAATTGCGCGCATTACCCTGTTATCCCTA
CGCGCTTGGCGTAATCATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGTATTTGGTA
TCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC pGSH0_mir451shRNA_Tyr2A, SEQ ID NO:43
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG

Figure 7 (cont.)

TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCGCACTTGGGAATGGCAAGGTTAGTATACAAATTTGTTCAC
GAACAAATTTGTATACTACTCTTGCTATACCCAGAAAAATGCATCTTCACGCGTAGCTTCCCTTAATACAAGT
GAGATGATGGCATACCATCTTTCGGGACTGAGTTGATGTGAAGAGTTTTTCTGTTTTGCTGATCACTTGTATA
TTATGTGACTAATAGTTAAAGTGCCAAAATAAAATGTGGGAACATTGAATGTGTATCCTACTTAAGGGAATCG
ATTTCAAGGAGGACGGAAACATCCTCGGCCACAAGTTGGAATACAACTACAACTCCCACAACGTATACATCAT
GGCCGACAAGCAAAAGAACGGCATCAAAGCCAACTTCAAGACCCGCCACAACATCGAAGACGGCGGCGTGCAA
CTCGCTGATCATTATCAACAAAATACTCCAATTGGCGATGACCCTGTCCTTTTACCAGACAACCATTACCTGT
CCACACAATCTGCCCTTTCGAAAGATCCCAACGAAAAGAGAGACCACATGGTCCTTCTTGAGTTTGTAACGGC
TGCTGGGATTACACATGGCATGGATGAACTATACAAAAATCTAGAACTATAGTGAGTCGTATTACGTAGATCC
AGACATGATAAGATACATTGATGAGTTTGGACAAACCACAACTAGAATGCAGTGAAAAAAATGCTTTATTTGT
GAAATTTGTGATGCTATTGCTTTATTTGTAACCATTATAAGCTGCAATAAACAAGTTAACAACAACAATTGCA
TTCATTTTATGTTTCAGGTTCAGGGGGAGGTGTGGGAGGTTTTTTAATTCGCGGCCGCCACCGCGGTGGAGCT
CCAGCTTTTGTTCCCTTTAGTGAGGGTTAATTGCGCGCATTACCCTGTTATCCCTACGCGCTTGGCGTAATCA
TGGTCATAGCTGTTTCCTGTGTGAAATTGTTATCCGCTCACAATTCCACACAACATACGAGCCGGAAGCATAA
AGTGTAAAGCCTGGGGTGCCTAATGAGTGAGCTAACTCACATTAATTGCGTTGCGCTCACTGCCCGCTTTCCA
GTCGGGAAACCTGTCGTGCCAGCTGCATTAATGAATCGGCCAACGCGCGGGGAGAGGCGGTTTGCGTATTGGG
CGCTCTTCCGCTTCCTCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCACGC
TCACCGGCTCCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTCAGCTCCGGT
TCCCAACGATCAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTCTCTTACTGT
CATGCCATCCGTAAGATGCTTTTCTGTGACTGGTGAGTACTCAACCAAGTCATTCTGAGAATAGTGTATGCGG
CGACCGAGTTGCTCTTGCCCGGCGTCAATACGGGATAATACCGCGCCACATAGCAGAACTTTAAAAGTGCTCA
TCATTGGAAAACGTTCTTCGGGGCGAAAACTCTCAAGGATCTTACCGCTGTTGAGATCCAGTTCGATGTAACC
CACTCGTGCACCCAACTGATCTTCAGCATCTTTTACTTTCACCAGCGTTTCTGGGTGAGCAAAAACAGGAAGG

Figure 7 (cont.)

CAAAATGCCGCAAAAAAGGGAATAAGGGCGACACGGAAATGTTGAATACTCATACTCTTCCTTTTTCAATATT
ATTGAAGCATTTATCAGGGTTATTGTCTCATGAGCGGATACATATTTGAATGTATTTAGAAAAATAAACAAAT
AGGGGTTCCGCGCACATTTCCCCGAAAAGTGCCAC pGSH0_mir451shRNA_Tyr6C, SEQ ID NO:44
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCGCACTTGGGAATGGCAAGGTTGGGAAAGTCCCAGTGGGCC
GCCACTGGGACTTTCCCACTCTTGCTATACCCAGAAAAATGCATCTTCACGCGTAGCTTCCCTTAATACAAGT
GAGATGATGGCATACCATCTTTCGGGACTGAGTTGATGTGAAGAGTTTTTCTGTTTTGCTGATCACTTGTATA
TTATGTGACTAATAGTTAAAGTGCCAAAATAAAATGTGGGAACATTGAATGTGTATCCTACTTAAGGGAATCG
ATTTCAAGGAGGACGGAAACATCCTCGGCCACAAGTTGGAATACAACTACAACTCCCACAACGTATACATCAT
GGCCGACAAGCAAAAGAACGGCATCAAAGCCAACTTCAAGACCCGCCACAACATCGAAGACGGCGGCGTGCAA
CTCGCTGATCATTATCAACAAAATACTCCAATTGGCGATGACCCTGTCCTTTTACCAGACAACCATTACCTGT
CCACACAATCTGCCCTTTCGAAAGATCCCAACGAAAAGAGAGACCACATGGTCCTTCTTGAGTTTGTAACGGC
TGCTGGGATTACACATGGCATGGATGAACTATACAAAAATCTAGAACTATAGTGAGTCGTATTACGTAGATCC
AGACATGATAAGATACATTGATGAGTTTGGACAAACCACAACTAGAATGCAGTGAAAAAAATGCTTTATTTGT
GAAATTTGTGATGCTATTGCTTTATTTGTAACCATTATAAGCTGCAATAAACAAGTTAACAACAACAATTGCA
TTCATTTTATGTTTCAGGTTCAGGGGGAGGTGTGGGAGGTTTTTTAATTCGCGGCCGCCACCGCGGTGGAGCT
CCAGCTTTTGTTCCCTTTAGTGAGGGTTAATTGCGCGCATTACCCTGTTATCCCTACGCGCTTGGCGTAATCA
TGGTCATAGCTGTTTCCTGTGTGAAATTGTTATCCGCTCACAATTCCACACAACATACGAGCCGGAAGCATAA
AGTGTAAAGCCTGGGGTGCCTAATGAGTGAGCTAACTCACATTAATTGCGTTGCGCTCACTGCCCGCTTTCCA
GTCGGGAAACCTGTCGTGCCAGCTGCATTAATGAATCGGCCAACGCGCGGGGAGAGGCGGTTTGCGTATTGGG
CGCTCTTCCGCTTCCTCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTGAGCAAAAGGCCAGCA

Figure 7 (cont.)

AAAGGCCAGGAACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCACGC
TCACCGGCTCCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTCAGCTCCGGT
TCCCAACGATCAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTCTCTTACTGT
CATGCCATCCGTAAGATGCTTTTCTGTGACTGGTGAGTACTCAACCAAGTCATTCTGAGAATAGTGTATGCGG
CGACCGAGTTGCTCTTGCCCGGCGTCAATACGGGATAATACCGCGCCACATAGCAGAACTTTAAAAGTGCTCA
TCATTGGAAAACGTTCTTCGGGGCGAAAACTCTCAAGGATCTTACCGCTGTTGAGATCCAGTTCGATGTAACC
CACTCGTGCACCCAACTGATCTTCAGCATCTTTTACTTTCACCAGCGTTTCTGGGTGAGCAAAAACAGGAAGG
CAAAATGCCGCAAAAAAGGGAATAAGGGCGACACGGAAATGTTGAATACTCATACTCTTCCTTTTTCAATATT
ATTGAAGCATTTATCAGGGTTATTGTCTCATGAGCGGATACATATTTGAATGTATTTAGAAAAATAAACAAAT
AGGGGTTCCGCGCACATTTCCCCGAAAAGTGCCAC pGSH0_2ndGenshRNA_Tyr2A, SEQ ID NO:45
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT

Figure 7 (cont.)

GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTGAGCGCCGTGAACAAATTTGTATACTAATA
GTGAAGCCACAGATGTATTAGTATACAAATTTGTTCACGTTGCCTACTGCCTTATGCATCTTCACGCGTAGCT
TCCCTTAATACAAGTGAGATGATGGCATACCATCTTTCGGGACTGAGTTGATGTGAAGAGTTTTTCTGTTTTG
CTGATCACTTGTATATTATGTGACTAATAGTTAAAGTGCCAAAATAAAATGTGGGAACATTGAATGTGTATCC
TACTTAAGGGAATCGATTTCAAGGAGGACGGAAACATCCTCGGCCACAAGTTGGAATACAACTACAACTCCCA
CAACGTATACATCATGGCCGACAAGCAAAAGAACGGCATCAAAGCCAACTTCAAGACCCGCCACAACATCGAA
GACGGCGGCGTGCAACTCGCTGATCATTATCAACAAAATACTCCAATTGGCGATGACCCTGTCCTTTTACCAG
ACAACCATTACCTGTCCACACAATCTGCCCTTTCGAAAGATCCCAACGAAAAGAGAGACCACATGGTCCTTCT
TGAGTTTGTAACGGCTGCTGGGATTACACATGGCATGGATGAACTATACAAAAATCTAGAACTATAGTGAGTC
GTATTACGTAGATCCAGACATGATAAGATACATTGATGAGTTTGGACAAACCACAACTAGAATGCAGTGAAAA
AAATGCTTTATTTGTGAAATTTGTGATGCTATTGCTTTATTTGTAACCATTATAAGCTGCAATAAACAAGTTA
ACAACAACAATTGCATTCATTTTATGTTTCAGGTTCAGGGGGAGGTGTGGGAGGTTTTTTAATTCGCGGCCGC
CACCGCGGTGGAGCTCCAGCTTTTGTTCCCTTTAGTGAGGGTTAATTGCGCGCATTACCCTGTTATCCCTACG
CGCTTGGCGTAATCATGGTCATAGCTGTTTCCTGTGTGAAATTGTTATCCGCTCACAATTCCACACAACATAC
GAGCCGGAAGCATAAAGTGTAAAGCCTGGGGTGCCTAATGAGTGAGCTAACTCACATTAATTGCGTTGCGCTC
ACTGCCCGCTTTCCAGTCGGGAAACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGGATACCTGTCCGCCTT
TCTCCCTTCGGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAAGATCCTTTGAT
CTTTTCTACGGGGTCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCATAGT
TGCCTGACTCCCCGTCGTGTAGATAACTACGATACGGGAGGGCTTACCATCTGGCCCCAGTGCTGCAATGATA
CCGCGAGACCCACGCTCACCGGCTCCAGATTTATCAGCAATAAACCAGCCAGCCGGAAGGGCCGAGCGCAGAA
GTGGTCCTGCAACTTTATCCGCCTCCATCCAGTCTATTAATTGTTGCCGGGAAGCTAGAGTAAGTAGTTCGCC
AGTTAATAGTTTGCGCAACGTTGTTGCCATTGCTACAGGCATCGTGGTGTCACGCTCGTCGTTTGGTATGGCT
TCATTCAGCTCCGGTTCCCAACGATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACTGCA
TAATTCTCTTACTGTCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGA
GCAAAAACAGGAAGGCAAAATGCCGCAAAAAAGGGAATAAGGGCGACACGGAAATGTTGAATACTCATACTCT
TCCTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCAC pGSH0_2ndGenshRNA_Tyr6C, SEQ ID NO:46

CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT

Figure 7 (cont.)

AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCTGCTGACAGTGAGCGCCGGCCCACTGGGACTTTCCCAATA
GTGAAGCCACAGATGTATTGGGAAAGTCCCAGTGGGCCGTTGCCTACTGCCTTATGCATCTTCACGCGTAGCT
TCCCTTAATACAAGTGAGATGATGGCATACCATCTTTCGGGACTGAGTTGATGTGAAGAGTTTTTCTGTTTTG
CTGATCACTTGTATATTATGTGACTAATAGTTAAAGTGCCAAAATAAAATGTGGGAACATTGAATGTGTATCC
TACTTAAGGGAATCGATTTCAAGGAGGACGGAAACATCCTCGGCCACAAGTTGGAATACAACTACAACTCCCA
CAACGTATACATCATGGCCGACAAGCAAAAGAACGGCATCAAAGCCAACTTCAAGACCCGCCACAACATCGAA
GACGGCGGCGTGCAACTCGCTGATCATTATCAACAAAATACTCCAATTGGCGATGACCCTGTCCTTTTACCAG
ACAACCATTACCTGTCCACACAATCTGCCCTTTCGAAAGATCCCAACGAAAAGAGAGACCACATGGTCCTTCT
TGAGTTTGTAACGGCTGCTGGGATTACACATGGCATGGATGAACTATACAAAAATCTAGAACTATAGTGAGTC
GTATTACGTAGATCCAGACATGATAAGATACATTGATGAGTTTGGACAAACCACAACTAGAATGCAGTGAAAA
AAATGCTTTATTTGTGAAATTTGTGATGCTATTGCTTTATTTGTAACCATTATAAGCTGCAATAAACAAGTTA
ACAACAACAATTGCATTCATTTTATGTTTCAGGTTCAGGGGGAGGTGTGGGAGGTTTTTTAATTCGCGGCCGC
CACCGCGGTGGAGCTCCAGCTTTTGTTCCCTTTAGTGAGGGTTAATTGCGCGCATTACCCTGTTATCCCTACG
CGCTTGGCGTAATCATGGTCATAGCTGTTTCCTGTGTGAAATTGTTATCCGCTCACAATTCCACACAACATAC
GAGCCGGAAGCATAAAGTGTAAAGCCTGGGGTGCCTAATGAGTGAGCTAACTCACATTAATTGCGTTGCGCTC
ACTGCCCGCTTTCCAGTCGGGAAACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGGATACCTGTCCGCCTT
TCTCCCTTCGGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAAGATCCTTTGAT

Figure 7 (cont.)

CTTTTCTACGGGGTCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCATAGT
TGCCTGACTCCCCGTCGTGTAGATAACTACGATACGGGAGGGCTTACCATCTGGCCCCAGTGCTGCAATGATA
CCGCGAGACCCACGCTCACCGGCTCCAGATTTATCAGCAATAAACCAGCCAGCCGGAAGGGCCGAGCGCAGAA
GTGGTCCTGCAACTTTATCCGCCTCCATCCAGTCTATTAATTGTTGCCGGGAAGCTAGAGTAAGTAGTTCGCC
AGTTAATAGTTTGCGCAACGTTGTTGCCATTGCTACAGGCATCGTGGTGTCACGCTCGTCGTTTGGTATGGCT
TCATTCAGCTCCGGTTCCCAACGATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACTGCA
TAATTCTCTTACTGTCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGA
GCAAAAACAGGAAGGCAAAATGCCGCAAAAAAGGGAATAAGGGCGACACGGAAATGTTGAATACTCATACTCT
TCCTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCAC

GSH0_Nek2 OshR1, SEQ ID NO:47

CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCCTTCGTCGACCGTTGACAGTGAGCGACTTCTTCCACTGAA
GGTCGATGGCCGTGAAGCCACAAATGGGCCATCGACCTAGTGGATGAAGCTGCCTACTGCCTAATGCATCTTC
ACGCGTAGCTTCCCTTAATACAAGTGAGATGATGGCATACCATCTTTCGGGACTGAGTTGATGTGAAGAGTTT
TTCTGTTTTGCTGATCACTTGTATATTATGTGACTAATAGTTAAAGTGCCAAAATAAAATGTGGGAACATTGA
ATGTGTATCCTACTTAAGGGAATCGATTTCAAGGAGGACGGAAACATCCTCGGCCACAAGTTGGAATACAACT

Figure 7 (cont.)

ACAACTCCCACAACGTATACATCATGGCCGACAAGCAAAAGAACGGCATCAAAGCCAACTTCAAGACCCGCCA
CAACATCGAAGACGGCGGCGTGCAACTCGCTGATCATTATCAACAAAATACTCCAATTGGCGATGACCCTGTC
CTTTTACCAGACAACCATTACCTGTCCACACAATCTGCCCTTTCGAAAGATCCCAACGAAAAGAGAGACCACA
TGGTCCTTCTTGAGTTTGTAACGGCTGCTGGGATTACACATGGCATGGATGAACTATACAAAAATCTAGAACT
ATAGTGAGTCGTATTACGTAGATCCAGACATGATAAGATACATTGATGAGTTTGGACAAACCACAACTAGAAT
GCAGTGAAAAAAATGCTTTATTTGTGAAATTTGTGATGCTATTGCTTTATTTGTAACCATTATAAGCTGCAAT
AAACAAGTTAACAACAACAATTGCATTCATTTTATGTTTCAGGTTCAGGGGGAGGTGTGGGAGGTTTTTTAAT
TCGCGGCCGCCACCGCGGTGGAGCTCCAGCTTTTGTTCCCTTTAGTGAGGGTTAATTGCGCGCATTACCCTGT
TATCCCTACGCGCTTGGCGTAATCATGGTCATAGCTGTTTCCTGTGTGAAATTGTTATCCGCTCACAATTCCA
CACAACATACGAGCCGGAAGCATAAAGTGTAAAGCCTGGGGTGCCTAATGAGTGAGCTAACTCACATTAATTG
CGTTGCGCTCACTGCCCGCTTTCCAGTCGGGAAACCTGTCGTGCCAGCTGCATTAATGAATCGGCCAACGCGC
GGGGAGAGGCGGTTTGCGTATTGGGCGCTCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGGCGTTTTTCCATAG
GCTCCGCCCCCCTGACGAGCATCACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCGACCCTGCCGCTTACCGGATACC
TGTCCGCCTTTCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTTATCCGGTAAC
TATCGTCTTGAGTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTAGAAGAACAGT
ATTTGGTATCTGCGCTCTGCTGAAGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCC
GAGCGCAGAAGTGGTCCTGCAACTTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGAAAACTCTCAAGGATCTTACCGC
TGTTGAGATCCAGTTCGATGTAACCCACTCGTGCACCCAACTGATCTTCAGCATCTTTTACTTTCACCAGCGT
TTCTGGGTGAGCAAAAACAGGAAGGCAAAATGCCGCAAAAAAGGGAATAAGGGCGACACGGAAATGTTGAATA
CTCATACTCTTCCTTTTTCAATATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCAC

GSH0_Nek2 OshR2, SEQ ID NO:48
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC

Figure 7 (cont.)

CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCCTTCGTCGACCGTTGACAGTGAGCGACTTGTCCTCTGCAA
GTCTCTCTCCCGTGAAGCCACAAATGGGGAGAGAGACTAAGAGGTCAAGCTGCCTACTGCCTAATGCATCTTC
ACGCGTAGCTTCCCTTAATACAAGTGAGATGATGGCATACCATCTTTCGGGACTGAGTTGATGTGAAGAGTTT
TTCTGTTTTGCTGATCACTTGTATATTATGTGACTAATAGTTAAAGTGCCAAAATAAAATGTGGGAACATTGA
ATGTGTATCCTACTTAAGGGAATCGATTTCAAGGAGGACGGAAACATCCTCGGCCACAAGTTGGAATACAACT
ACAACTCCCACAACGTATACATCATGGCCGACAAGCAAAAGAACGGCATCAAAGCCAACTTCAAGACCCGCCA
CAACATCGAAGACGGCGGCGTGCAACTCGCTGATCATTATCAACAAAATACTCCAATTGGCGATGACCCTGTC
CTTTTACCAGACAACCATTACCTGTCCACACAATCTGCCCTTTCGAAAGATCCCAACGAAAAGAGAGACCACA
TGGTCCTTCTTGAGTTTGTAACGGCTGCTGGGATTACACATGGCATGGATGAACTATACAAAAATCTAGAACT
ATAGTGAGTCGTATTACGTAGATCCAGACATGATAAGATACATTGATGAGTTTGGACAAACCACAACTAGAAT
GCAGTGAAAAAAATGCTTTATTTGTGAAATTTGTGATGCTATTGCTTTATTTGTAACCATTATAAGCTGCAAT
AAACAAGTTAACAACAACAATTGCATTCATTTTATGTTTCAGGTTCAGGGGGAGGTGTGGGAGGTTTTTTAAT
TCGCGGCCGCCACCGCGGTGGAGCTCCAGCTTTTGTTCCCTTTAGTGAGGGTTAATTGCGCGCATTACCCTGT
TATCCCTACGCGCTTGGCGTAATCATGGTCATAGCTGTTTCCTGTGTGAAATTGTTATCCGCTCACAATTCCA
CACAACATACGAGCCGGAAGCATAAAGTGTAAAGCCTGGGGTGCCTAATGAGTGAGCTAACTCACATTAATTG
CGTTGCGCTCACTGCCCGCTTTCCAGTCGGGAAACCTGTCGTGCCAGCTGCATTAATGAATCGGCCAACGCGC
GGGGAGAGGCGGTTTGCGTATTGGGCGCTCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGGCGTTTTTCCATAG
GCTCCGCCCCCCTGACGAGCATCACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCGACCCTGCCGCTTACCGGATACC
TGTCCGCCTTTCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTTATCCGGTAAC
TATCGTCTTGAGTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTAGAAGAACAGT
ATTTGGTATCTGCGCTCTGCTGAAGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCC
GAGCGCAGAAGTGGTCCTGCAACTTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAGTGTTATCACTCATGGTTATGG

Figure 7 (cont.)

CAGCACTGCATAATTCTCTTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGAAAACTCTCAAGGATCTTACCGC
TGTTGAGATCCAGTTCGATGTAACCCACTCGTGCACCCAACTGATCTTCAGCATCTTTTACTTTCACCAGCGT
TTCTGGGTGAGCAAAAACAGGAAGGCAAAATGCCGCAAAAAAGGGAATAAGGGCGACACGGAAATGTTGAATA
CTCATACTCTTCCTTTTTCAATATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCAC

GSH0_Nek2 OshR3, SEQ ID NO:49

CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGTAGGGATAACAGGGTAATGCGCGCGTAATACGAC
TCACTATAGGGCGAATTGGGTACCGGGCCCCCCCTCGACCATAGCCAATTCAATATGGCGTATATGGACTCAT
GCCAATTCAATATGGTGGATCTGGACCTGTGCCAATTCAATATGGCGTATATGGACTCGTGCCAATTCAATAT
GGTGGATCTGGACCCCAGCCAATTCAATATGGCGGACTTGGCACCATGCCAATTCAATATGGCGGACTTGGCA
CTGTGCCAACTGGGGAGGGGTCTACTTGGCACGGTGCCAAGTTTGAGGAGGGGTCTTGGCCCTGTGCCAAGTC
CGCCATATTGAATTGGCATGGTGCCAATAATGGCGGCCATATTGGCTATATGCCAGGATCAATATATAGGCAA
TATCCAATATGGCCCTATGCCAATATGGCTATTGGCCAGGTTCAATACTATGTATTGGCCCTATGCCATATAG
TATTCCATATATGGGTTTTCCTATTGACGTAGATAGCCCCTCCCAATGGGCGGTCCCATATACCATATATGGG
GCTTCCTAATACCGCCCATAGCCACTCCCCCATTGACGTCAATGGTCTCTATATATGGTCTTTCCTATTGACG
TCATATGGGCGGTCCTATTGACGTATATGGCGCCTCCCCCATTGACGTCAATTACGGTAAATGGCCCGCCTGG
CTCAATGCCCATTGACGTCAATAGGACCACCCACCATTGACGTCAATGGGATGGCTCATTGCCCATTCATATC
CGTTCTCACGCCCCCTATTGACGTCAATGACGGTAAATGGCCCACTTGGCAGTACATCAATATCTATTAATAG
TAACTTGGCAAGTACATTACTATTGGAAGTACGCCAGGGTACATTGGCAGTACTCCCATTGACGTCAATGGCG
GTAAATGGCCCGCGATGGCTGCCAAGTACATCCCCATTGACGTCAATGGGGAGGGGCAATGACGCAAATGGGC
GTTCCATTGACGTAAATGGGCGGTAGGCGTGCCTAATGGGAGGTCTATATAAGCAATGCTCGTTTAGGGAACC
GCCATTCTGCCTGGGGACGTCGGAGCAAGCTAGCTTGCTTGTTCTTTTTGCAGAAGCTCAGAATAAACGCTCA
ACTTTGGCAGATCTGAATTCCTGCAGCCCGGGGGATCCACAGCCACCATGAGTAAAGGAGAAGAACTTTTCAC
TGGAGTTGTCCCAATTCTTGTTGAATTAGATGGTGATGTTAATGGGTACAAATTTTCTGTCAGTGGAGAGGGT
GAAGGTGATGCAACATACGGAAAACTTACCCTTAAATTTATTTGCACTACTGGAAAACTACCTGTTCCATGGC
CAACACTTGTCACTACTCTCACTTATGGTGTTCAATGCTTTTCAAGATATCCAGATCATATGAAGCGGCACGA
CTTCTTCAAGAGCGCCATGCCTGAGGGATACGTGCAGGAGAGGACCATCTTCTTCAAGGACGACGGGAACTAC
AAGACACGTGCTGAAGTCAAGTTTGAGGGAGACACCCTCGTCAACAGGATCGAGCTTAAGGTAAGAAAAGTTC
ACATCTGAGTAGGTAGAATAAAAAGCTGCATGCCTTCGTCGACCGTTGACAGTGAGCGACTTCTTCAGGTCCC
TGCACTTGGCCGTGAAGCCACAAATGGGCCAAGTGCAGCCCTGATGAAGCTGCCTACTGCCTAATGCATCTTC
ACGCGTAGCTTCCCTTAATACAAGTGAGATGATGGCATACCATCTTTCGGGACTGAGTTGATGTGAAGAGTTT
TTCTGTTTTGCTGATCACTTGTATATTATGTGACTAATAGTTAAAGTGCCAAAATAAAATGTGGGAACATTGA
ATGTGTATCCTACTTAAGGGAATCGATTTCAAGGAGGACGGAAACATCCTCGGCCACAAGTTGGAATACAACT
ACAACTCCCACAACGTATACATCATGGCCGACAAGCAAAAGAACGGCATCAAAGCCAACTTCAAGACCCGCCA
CAACATCGAAGACGGCGGCGTGCAACTCGCTGATCATTATCAACAAAATACTCCAATTGGCGATGACCCTGTC
CTTTTACCAGACAACCATTACCTGTCCACACAATCTGCCCTTTCGAAAGATCCCAACGAAAAGAGAGACCACA
TGGTCCTTCTTGAGTTTGTAACGGCTGCTGGGATTACACATGGCATGGATGAACTATACAAAAATCTAGAACT
ATAGTGAGTCGTATTACGTAGATCCAGACATGATAAGATACATTGATGAGTTTGGACAAACCACAACTAGAAT
GCAGTGAAAAAAATGCTTTATTTGTGAAATTTGTGATGCTATTGCTTTATTTGTAACCATTATAAGCTGCAAT
AAACAAGTTAACAACAACAATTGCATTCATTTTATGTTTCAGGTTCAGGGGGAGGTGTGGGAGGTTTTTTAAT
TCGCGGCCGCCACCGCGGTGGAGCTCCAGCTTTTGTTCCCTTTAGTGAGGGTTAATTGCGCGCATTACCCTGT
TATCCCTACGCGCTTGGCGTAATCATGGTCATAGCTGTTTCCTGTGTGAAATTGTTATCCGCTCACAATTCCA

Figure 7 (cont.)

CACAACATACGAGCCGGAAGCATAAAGTGTAAAGCCTGGGGTGCCTAATGAGTGAGCTAACTCACATTAATTG
CGTTGCGCTCACTGCCCGCTTTCCAGTCGGGAAACCTGTCGTGCCAGCTGCATTAATGAATCGGCCAACGCGC
GGGGAGAGGCGGTTTGCGTATTGGGCGCTCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGGCGTTTTTCCATAG
GCTCCGCCCCCCTGACGAGCATCACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCGACCCTGCCGCTTACCGGATACC
TGTCCGCCTTTCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTTATCCGGTAAC
TATCGTCTTGAGTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTAGAAGAACAGT
ATTTGGTATCTGCGCTCTGCTGAAGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCC
GAGCGCAGAAGTGGTCCTGCAACTTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGAAAACTCTCAAGGATCTTACCGC
TGTTGAGATCCAGTTCGATGTAACCCACTCGTGCACCCAACTGATCTTCAGCATCTTTTACTTTCACCAGCGT
TTCTGGGTGAGCAAAAACAGGAAGGCAAAATGCCGCAAAAAAGGGAATAAGGGCGACACGGAAATGTTGAATA
CTCATACTCTTCCTTTTTCAATATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCAC

NEK2 wild type ORF with myc epitope SEQ ID NO:50
ATGGCATCAATGCAGAAGCTGATCTCAGAGGAGGACCTGCTTATGGCCATGGAGGCCCGAATTCGGTCGACCG
AGATCTCTCGAAGCGGCGCGGTGGTGTGGTTGCCAGGGTGGCCGCTCGCCATGCCGTCCCGGGTGGAGGACTA
CGAGGTGCTGCACAGCATCGGCACCGGCTCCTACGGCCGCTGTCAGAAGATTCGGAGGAAGAGCGACGGCAAG
ATCCTGGTGTGGAAAGAGCTTGACTATGGCTCCATGACGGAGGTGGAGAAGCAGATGCTTGTGTCTGAAGTGA
ACTTGCTTCGGGAGCTGAAACATCCAAACATCGTCCGTTACTATGATCGCATTATTGACCGAACCAACACAAC
CCTGTACATCGTAATGGAATACTGTGAGGGAGGGGACCTGGCTAGTGTCATTTCAAAGGGGACCAAGGATAGA
CAGTACTTGGAAGAAGAGTTTGTCCTTCGAGTGATGACTCAGTTGACGCTGGCCCTGAAAGAGTGTCACAGAA
GGAGCGATGGTGGCCACACTGTGCTTCACCGGGACCTGAAGCCAGCCAATGTCTTCCTGGACAGCAAACACAA
TGTCAAGCTGGGGGACTTTGGACTAGCTAGAATATTAAATCACGACACGAGTTTTGCAAAAACGTTTGTTGGC
ACACCCTATTACATGTCTCCTGAACAGATGAGCTGCTTATCCTACAACGAGAAGTCGGACATCTGGTCCTTGG
GCTGCCTGCTGTATGAGCTGTGTGCACTAATGCCTCCCTTTACAGCTTTCAACCAAAAAGAGCTAGCTGGGAA
AATCAGGGAAGGGAGGTTCAGGCGCATCCCCTACCGCTACTCTGATGGCTTGAATGACCTCATCACTCGGATG
CTGAATTTAAAGGACTACCATCGACCTTCAGTGGAAGAAATTCTGGAGAGCCCTTTGATAGCAGACATGGTTG
CAGAAGAGCAAAGGAGAAATCTGGAGAGGAGAGGACGGCGCTCAGGCGAGCCTTCGAAGCTGCCGGACTCCAG
CCCTGTGCTGAGCGAGCTCAAGTTGAAGGAAAGGCAACTGCAGGATCGAGAGCAAGCACTCAGAGCTCGGGAG
GACATTCTGGAGCAGAAGGAACGTGAACTTTGTATTCGAGAGAGACTTGCAGAGGACAAACTGGCCAGAGCCG
AGAGCCTGATGAAGAACTACAGCCTGCTGAAGGAGCACAGGCTCCTATGTCTGGCTGGTGGCCCAGAACTTGA
TCTTCCATCCTCAGCCATGAAGAAGAAGGTTCATTTCCACGGGGAAAGCAAAGAGAACACCGCAAGGAGTGAG
AATTCTGAGAGCTACCTTGCCAAGTCCAAGTGCAGGGACCTGAAGAAGAGGCTTCATGCTGCCCAGCTGCGGG
CTCAAGCCCTGGCTGATATTGAAAAAAACTACCAGCTAAAGAGCAGGCAGATCCTGGGCATGCGC

Figure 7 (cont.)

NEK2 OshR1 SDM, SEQ ID NO:51

ATGGCATCAATGCAGAAGCTGATCTCAGAGGAGGACCTGCTTATGGCCATGGAGGCCCGAATTCGGTCGACCG
AGATCTCTCGAAGCGGCGCGGTGGTGTGGTTGCCAGGGTGGCCGCTCGCCATGCCGTCCCGGGTGGAGGACTA
CGAGGTGCTGCACAGCATCGGCACCGGCTCCTACGGCCGCTGTCAGAAGATTCGGAGGAAGAGCGACGGCAAG
ATCCTGGTGTGGAAAGAGCTTGACTATGGCTCCATGACGGAGGTGGAGAAGCAGATGCTTGTGTCTGAAGTGA
ACTTGCTTCGGGAGCTGAAACATCCAAACATCGTCCGTTACTATGATCGCATTATTGACCGAACCAACACAAC
CCTGTACATCGTAATGGAATACTGTGAGGGAGGGGACCTGGCTAGTGTCATTTCAAAGGGGACCAAGGATAGA
CAGTACTTGGAAGAAGAGTTTGTCCTTCGAGTGATGACTCAGTTGACGCTGGCCCTGAAAGAGTGTCACAGAA
GGAGCGATGGTGGCCACACTGTGCTTCACCGGGACCTGAAGCCAGCCAATGTCTTCCTGGACAGCAAACACAA
TGTCAAGCTGGGGGACTTTGGACTAGCTAGAATATTAAATCACGACACGAGTTTTGCAAAAACGTTTGTTGGC
ACACCCTATTACATGTCTCCTGAACAGATGAGCTGCTTATCCTACAACGAGAAGTCGGACATCTGGTCCTTGG
GCTGCCTGCTGTATGAGCTGTGTGCACTAATGCCTCCCTTTACAGCTTTCAACCAAAAAGAGCTAGCTGGGAA
AATCAGGGAAGGGAGGTTCAGGCGCATCCCCTACCGCTACTCTGATGGCTTGAATGACCTCATCACTCGGATG
CTGAATTTAAAGGACTACCATCGACCTTCAGTGGAGGAAATTCTGGAGAGCCCTTTGATAGCAGACATGGTTG
CAGAAGAGCAAAGGAGAAATCTGGAGAGGAGAGGACGGCGCTCAGGCGAGCCTTCGAAGCTGCCGGACTCCAG
CCCTGTGCTGAGCGAGCTCAAGTTGAAGGAAAGGCAACTGCAGGATCGAGAGCAAGCACTCAGAGCTCGGGAG
GACATTCTGGAGCAGAAGGAACGTGAACTTTGTATTCGAGAGAGACTTGCAGAGGACAAACTGGCCAGAGCCG
AGAGCCTGATGAAGAACTACAGCCTGCTGAAGGAGCACAGGCTCCTATGTCTGGCTGGTGGCCCAGAACTTGA
TCTTCCATCCTCAGCCATGAAGAAGAAGGTTCATTTCCACGGGGAAAGCAAAGAGAACACCGCAAGGAGTGAG
AATTCTGAGAGCTACCTTGCCAAGTCCAAGTGCAGGGACCTGAAGAAGAGGCTTCATGCTGCCCAGCTGCGGG
CTCAAGCCCTGGCTGATATTGAAAAAAACTACCAGCTAAAGAGCAGGCAGATCCTGGGCATGCGC

NEK2 OshR2 SDM, SEQ ID NO:52

ATGGCATCAATGCAGAAGCTGATCTCAGAGGAGGACCTGCTTATGGCCATGGAGGCCCGAATTCGGTCGACCG
AGATCTCTCGAAGCGGCGCGGTGGTGTGGTTGCCAGGGTGGCCGCTCGCCATGCCGTCCCGGGTGGAGGACTA
CGAGGTGCTGCACAGCATCGGCACCGGCTCCTACGGCCGCTGTCAGAAGATTCGGAGGAAGAGCGACGGCAAG
ATCCTGGTGTGGAAAGAGCTTGACTATGGCTCCATGACGGAGGTGGAGAAGCAGATGCTTGTGTCTGAAGTGA
ACTTGCTTCGGGAGCTGAAACATCCAAACATCGTCCGTTACTATGATCGCATTATTGACCGAACCAACACAAC
CCTGTACATCGTAATGGAATACTGTGAGGGAGGGGACCTGGCTAGTGTCATTTCAAAGGGGACCAAGGATAGA
CAGTACTTGGAAGAAGAGTTTGTCCTTCGAGTGATGACTCAGTTGACGCTGGCCCTGAAAGAGTGTCACAGAA
GGAGCGATGGTGGCCACACTGTGCTTCACCGGGACCTGAAGCCAGCCAATGTCTTCCTGGACAGCAAACACAA
TGTCAAGCTGGGGGACTTTGGACTAGCTAGAATATTAAATCACGACACGAGTTTTGCAAAAACGTTTGTTGGC
ACACCCTATTACATGTCTCCTGAACAGATGAGCTGCTTATCCTACAACGAGAAGTCGGACATCTGGTCCTTGG
GCTGCCTGCTGTATGAGCTGTGTGCACTAATGCCTCCCTTTACAGCTTTCAACCAAAAAGAGCTAGCTGGGAA
AATCAGGGAAGGGAGGTTCAGGCGCATCCCCTACCGCTACTCTGATGGCTTGAATGACCTCATCACTCGGATG
CTGAATTTAAAGGACTACCATCGACCTTCAGTGGAAGAAATTCTGGAGAGCCCTTTGATAGCAGACATGGTTG
CAGAAGAGCAAAGGAGAAATCTGGAGAGGAGAGGACGGCGCTCAGGCGAGCCTTCGAAGCTGCCGGACTCCAG
CCCTGTGCTGAGCGAGCTCAAGTTGAAGGAAAGGCAACTGCAGGATCGAGAGCAAGCACTCAGAGCTCGGGAG
GACATTCTGGAGCAGAAGGAACGTGAACTTTGTATTCGAGAGAGACTTGCCGAGGACAAACTGGCCAGAGCCG
AGAGCCTGATGAAGAACTACAGCCTGCTGAAGGAGCACAGGCTCCTATGTCTGGCTGGTGGCCCAGAACTTGA
TCTTCCATCCTCAGCCATGAAGAAGAAGGTTCATTTCCACGGGGAAAGCAAAGAGAACACCGCAAGGAGTGAG
AATTCTGAGAGCTACCTTGCCAAGTCCAAGTGCAGGGACCTGAAGAAGAGGCTTCATGCTGCCCAGCTGCGGG
CTCAAGCCCTGGCTGATATTGAAAAAAACTACCAGCTAAAGAGCAGGCAGATCCTGGGCATGCGC

NEK2 OshR3 SDM, SEQ ID NO:53

ATGGCATCAATGCAGAAGCTGATCTCAGAGGAGGACCTGCTTATGGCCATGGAGGCCCGAATTCGGTCGACCG
AGATCTCTCGAAGCGGCGCGGTGGTGTGGTTGCCAGGGTGGCCGCTCGCCATGCCGTCCCGGGTGGAGGACTA
CGAGGTGCTGCACAGCATCGGCACCGGCTCCTACGGCCGCTGTCAGAAGATTCGGAGGAAGAGCGACGGCAAG
ATCCTGGTGTGGAAAGAGCTTGACTATGGCTCCATGACGGAGGTGGAGAAGCAGATGCTTCTGTCTGAAGTGA
ACTTGCTTCGGGAGCTGAAACATCCAAACATCGTCCGTTACTATGATCGCATTATTGACCGAACCAACACAAC
CCTGTACATCGTAATGGAATACTGTGAGGGAGGGGACCTGGCTAGTGTCATTTCAAAGGGGACCAAGGATAGA
CAGTACTTGGAAGAAGAGTTTGTCCTTCGAGTGATGACTCAGTTGACGCTGGCCCTGAAAGAGTGTCACAGAA

Figure 7 (cont.)

GGAGCGATGGTGGCCACACTGTGCTTCACCGGGACCTGAAGCCAGCCAATGTCTTCCTGGACAGCAAACACAA
TGTCAAGCTGGGGGACTTTGGACTAGCTAGAATATTAAATCACGACACGAGTTTTGCAAAAACGTTTGTTGGC
ACACCCTATTACATGTCTCCTGAACAGATGAGCTGCTTATCCTACAACGAGAAGTCGGACATCTGGTCCTTGG
GCTGCCTGCTGTATGAGCTGTGTGCACTAATGCCTCCCTTTACAGCTTTCAACCAAAAAGAGCTAGCTGGGAA
AATCAGGGAAGGGAGGTTCAGGCGCATCCCCTACCGCTACTCTGATGGCTTGAATGACCTCATCACTCGGATG
CTGAATTTAAAGGACTACCATCGACCTTCAGTGGAAGAAATTCTGGAGAGCCCTTTGATAGCAGACATGGTTG
CAGAAGAGCAAAGGAGAAATCTGGAGAGGAGAGGACGGCGCTCAGGCGAGCCTTCGAAGCTGCCGGACTCCAG
CCCTGTGCTGAGCGAGCTCAAGTTGAAGGAAAGGCAACTGCAGGATCGAGAGCAAGCACTCAGAGCTCGGGAG
GACATTCTGGAGCAGAAGGAACGTGAACTTTGTATTCGAGAGAGACTTGCAGAGGACAAACTGGCCAGAGCCG
AGAGCCTGATGAAGAACTACAGCCTGCTGAAGGAGCACAGGCTCCTATGTCTGGCTGGTGGCCCAGAACTTGA
TCTTCCATCCTCAGCCATGAAGAAGAAGGTTCATTTCCACGGGGAAAGCAAAGAGAACACCGCAAGGAGTGAG
AATTCTGAGAGCTACCTTGCCAAATCCAAGTGCAGGGACCTCAAGAAGAGGCTTCATGCTGCCCAGCTGCGGG
CTCAAGCCCTGGCTGATATTGAAAAAAACTACCAGCTAAAGAGCAGGCAGATCCTGGGCATGCGC

Figure 7 (cont.)

ORGANIC SMALL HAIRPIN RNAS

This application is a national stage application under 35 U.S.C. §371 of PCT Application No. PCT/US2014/013640, filed Jan. 29, 2014, which claims the priority benefit of U.S. Provisional Patent Application No. 61/829,621, filed May 31, 2013, which is incorporated by reference in its entirety.

This invention was made with Government support under National Institute of Health grant numbers R00HD057298 and R21DA026977. The Government has certain rights in the invention.

FIELD OF THE INVENTION

This invention is directed generally to organic short hairpin RNA and uses thereof.

BACKGROUND OF THE INVENTION

RNA interference (RNAi) is a natural and robust gene silencing process in animal cells that investigators can harness to silence the expression of practically any gene of interest. The power and versatility of RNAi stems from the relative ease of synthesizing and introducing into cells small RNAs with an enormous range of sequences that efficiently incorporate into the RNA Induced Silencing Complex (RISC) as Guide strands. Guide strands direct the RISC to specific complementary transcripts, and RISC then triggers catalytic inhibition of translation or degradation of the complementary transcripts. The RNAi methodology has revolutionized many areas of biology because it has enabled highly specific reverse genetics analyses in cultured animal cells, and become an essential tool in studying diseases from cancer to diabetes to neurological disorders.

In vertebrate cells, the biological function of the RNAi pathway is to regulate the expression of the transcriptome through microRNAs (miRNAs). Genome-encoded miRNA genes are transcribed by RNA-Polymerase (Pol) II as a long primary transcript (pri-miRNA) which is processed into a small hairpin-shaped precursor (pre-miRNA) by the Drosha enzyme, and then further processed by the Dicer enzyme into a small duplexed RNA. The resulting small RNA duplex is then sampled on both ends of the duplex for ease in unwinding the RNA ends according to the thermodynamics of RNA base-pairing. Thus, a single-stranded guide RNA, such as a mature miRNA sequence, becomes incorporated into an Argonaute protein that is the core effector protein of the RISC. The RISC can then bind transcripts, with as few as 7-8 nt of complementarity with the 'seed' sequence in the 5' end of the guide RNA, to trigger inhibition of translation and promote mRNA destabilization. However, complete complementarity through the entire length of the guide RNA can trigger catalytic cleavage of the mRNA and lead to more robust gene silencing.

Investigators harness RNAi by programming the RISC with two types of triggers: chemically synthesized small interfering RNA (siRNA) or vector-driven transgenes that express a short hairpin RNA (shRNA). Although still extensively used, siRNAs have the restrictions of higher cost and shorter-lived gene knockdown effects because the siRNA is diluted by cell division and RNA turnover. shRNAs were originally used by transfecting cells with a plasmid that expressed a short transcript driven by RNA Pol III type of promoters to make a small fold back structure which would be short enough not to trigger undesired innate immunity response.

Currently, due to unpredictability with respect to silencing efficacies and potential off-targeting effects from each individual shRNA, researchers targeting individual genes with shRNAs must obtain a panel of multiple shRNA constructs. In some instances an entire panel of shRNAs may fail. Failure is likely due to competition with the endogenous miRNA pathway, unpredictable guide versus passenger strand production, secondary structures and/or RNA binding proteins that occlude the RNAi machinery from accessing the mRNA. Thus, there is a continuing need for improved shRNAs with increased efficacy and reliability.

SUMMARY OF THE INVENTION

Provided herein are improved shRNA molecules, termed "organic shRNA" (OshRNA), incorporating certain structural features that increase the likelihood that the desired guide strand is produced while simultaneously reducing accumulation of passenger strands that can contribute to off-target effects. Also provided herein are nucleic acids encoding OshRNAs, kits, cells, and transgenic animals comprising such nucleic acids, as well as methods of making and using OshRNAs and/or nucleic acids encoding OshRNAs.

In certain embodiments, provided herein is a nucleic acid molecule (e.g., an isolated nucleic acid molecule) containing a nucleic acid sequence encoding an OshRNA sequence. In some embodiments, the OshRNA sequence includes, in 5' to 3' order, a 5' constant stem sequence, a guide sequence, a constant stem loop, a passenger sequence, and a 3' constant stem sequence. In certain embodiments, the 5' constant stem sequence is immediately 5' of the guide sequence. In some embodiments, the guide sequence is immediately 5' of the constant stem loop. In some embodiments, the constant step loop is immediately 5' of the passenger sequence. In some embodiments, the passenger sequence is immediately 5' of the 3' constant stem sequence.

In some embodiments, the guide sequence is a nucleic acid sequence of 19-29 nucleotides in length. In some embodiments, the guide sequence is 22 nucleotides in length. In some embodiments, the guide sequence contains an A/T/U rich region at its 5' end. In some embodiments, at least 3 of the 4 nucleotides at the 5' end of the guide sequence are A, T, or U. In some embodiments, the two nucleotides at the 5' end of the guide sequence are A, T, or U. In some embodiments, the two nucleotides at the 5' end of the guide sequence are TT. In some embodiments, the guide sequence contains a C/G rich region at its 3' end. In some embodiments, at least 3 of the 4 nucleotides at the 3' end of the guide sequence are C or G. In some embodiments, the two nucleotides at the 3' end of the guide sequence are C or G.

In some embodiments, the guide sequence is the reverse complement of a target nucleic acid sequence. In some embodiments, at least 18, 19, 20, 21, or 22 of the nucleotides of the guide sequence are the reverse complement of the target nucleic acid sequence. In some embodiments, the target nucleic acid sequence is encoded by a target gene. In some embodiments, the target gene is a human gene. In some embodiments, the nucleotide sequence at positions 12-21 are the reverse complement of a target nucleic acid sequence. In some embodiments, the nucleotide sequence at positions 12-21 do not complement a sequence encoded by any non-target gene expressed by the species that expresses the target gene (e.g., humans). In some embodiments, the target nucleic acid is in a 3' untranslated region or an open reading frame of a target mRNA.

In some embodiments, the passenger sequence is the reverse complement of the guide sequence, but with a non-complementing nucleotide at position 19 and with the nucleotides at positions 10 and 11, 11 and 12, or 12 and 13 absent.

In some embodiments, the 5' constant stem sequence is a miR-30a 5' constant stem sequence (e.g., a human, mouse, or *Xenopus* miR-30a 5' constant stem sequence). In some embodiments, the constant stem loop is a miR-30a constant stem loop (e.g., a human, mouse, or *Xenopus* miR-30a constant stem loop). In some embodiments, the 3' constant stem sequence is a miR-30a 3' constant stem sequence (e.g., a human, mouse, or *Xenopus* miR-30a 3' constant stem sequence).

In some embodiments, the nucleic acid molecule is a single-stranded RNA molecule (e.g., a single-stranded RNA molecule containing a hairpin secondary structure encoded by the OshRNA sequence). In some embodiments, the nucleic acid molecule is part of an RNA vector (e.g., a lentiviral vector or a retroviral vector).

In some embodiments, the nucleic acid molecule is a double-stranded DNA molecule. In some embodiments, the nucleic acid molecule is a part of a DNA vector (e.g., a plasmid or a viral vector). In some embodiments, the nucleic acid molecule is an expression vector. In some embodiments, the expression vector expresses an RNA molecule that includes the OshRNA sequence. In certain embodiments the RNA molecule is an mRNA molecule. In some embodiments, the OshRNA sequence is located in an intron or a 3' untranslated region of the mRNA molecule.

Also provided herein is a cell containing a nucleic acid molecule described herein. In some embodiments, the nucleic acid molecule is integrated into the genomic DNA of the cell. In some embodiments, the cell is a vertebrate cell. In some embodiments, the cell is a mammalian cell. In some embodiments, the cell is a human cell.

In some embodiments provided herein is a transgenic non-human animal containing a nucleic acid molecule described herein. In some embodiments, the nucleic acid molecule is integrated into the genomic DNA of the animal. In some embodiments, the animal is a vertebrate. In some embodiments, the animal is a mammal. In some embodiments, the animal is a mouse.

In certain embodiments, provided herein is a method of inhibiting expression of a target nucleic acid in a cell comprising contacting the cell with a nucleic acid molecule described herein. In some embodiments, the cell is a vertebrate cell. In some embodiments, the cell is a mammalian cell. In some embodiments, the cell is a human cell. In some embodiments, the method is performed in vitro. In some embodiments, the method is performed in vivo.

In certain embodiments, provided herein is a method of inhibiting expression of a target nucleic acid in a subject comprising contacting the subject with a nucleic acid molecule described herein. In some embodiments, the subject is a vertebrate. In some embodiments, the subject is a mammal. In some embodiments, the subject is a human.

In some embodiments, provided herein is a kit containing a nucleic acid molecule described herein. In some embodiments, the kit contains a plurality of different nucleic acid molecules described herein. In some embodiments, the kit contains a library of different nucleic acid molecules described herein (e.g., at least 10, 20, 30, 40, 50, 60, 70, 80, 90, or 100 different nucleic acid molecules).

In some embodiments, provided herein is an OshRNA library of nucleic acid molecules described herein (e.g., at least 10, 20, 30, 40, 50, 60, 70, 80, 90, or 100 different nucleic acid molecules).

In some embodiments, provided herein are methods of generating a nucleic acid molecule described herein. In some embodiments, provided herein is a method of designing an OshRNA molecule. In some embodiments, the method of designing an OshRNA molecule is an automated method.

BRIEF DESCRIPTION OF THE DRAWINGS

FIG. 1(A) is a schematic of the biogenesis pathway for miRNAs. (B) shows the secondary structure for the pri- and pre-miRNA-30 from mouse (SEQ ID NO:1), top; and *Xenopus* (SEQ ID NO:2), bottom.

FIG. 2 shows the design and decision workflow of the OshR platform. (A) Flowchart depicting an exemplary method for identifying a target sequence and designing OshRNAs. (B) Diagram of an exemplary OshRNA expression vector. According to this embodiment, the OshRNA is cloned into the intron of GFP and is generated after splicing and Drosha processing. (C) Diagram of an example OshR passenger strand sequence (SEQ ID NO:3) in relation to the guide strand sequence (SEQ ID NO:4), with base positions numbered above and below the sequences. Arrowheads note the deletion of bases at positions "11, 12" and arrow notes the mismatch at position "19" of the Passenger strand.

FIG. 3 shows that the OshR platform ensures proper Guide strand production. (A) Current shRNA designs display variability that results in accumulation of both the guide strand and passenger strand. (B) The Organic shRNA design builds in mismatches to direct specific Drosha and Dicer cleavage sites. (C) Secondary structures of the OshR 2A (SEQ ID NO:5) and 6C (SEQ ID NO:6) against the *X. tropicalis* Tyrosinase (Tyr) mRNA. Intentionally mismatched bases are underlined and uppercase. (D) Northern blots indicate OshR designs yield predominant accumulation of the guide Strand over passenger strand. Mock is a mock transfection; OshR is the OshRNA expression vector transfection; P. ctrl: synthetic Passenger strand mimic; G. ctrl: synthetic Guide strand mimic. Dashed rectangles mark lanes of shRNA production.

FIG. 4 shows gene silencing efficacy of various OshRNAs. (A) Diagram of OshR target sites against mouse NEK-2 (top) and western blots showing knockdown of Myc-tagged NEK2 (myc-NEK2) by all three OshRNAs (bottom). β-Actin is a loading control. Myc-NEK2 rescue constructs with mismatched bases to the OshRNAs are resistant to knockdown. (B) Diagram of OshR target sites against *Xenopus* Tyr (top) and western blots showing knockdown of FLAG-tagged Tyr by OshRs marked by dashed rectangles (bottom). β-Tubulin is a loading control and GFP indicates proper expression of the OshR vector. Untrn.: untransfected cells, Mock: is the empty vector.

FIG. 5 shows a comparison of the OshR platform to the second generation and miR-451 backbone platforms. Secondary structures of shTyr-2A in the second generation (A) (SEQ ID NO:7) and the miR-451 backbone (B) (SEQ ID NO:8). GFP expression of the shRNAs in the second generation (C) and miR-451 backbone (D) directly compared with the analogous sequence in the OshR platform. Northern blots detecting shRNA production in the second generation (E) and miR-451 backbone (F) directly compared with the analogous sequence in the OshR platform. Passenger strands were not assayed in (F) and 5S rRNA is a loading control. Western blots testing the knockdown of FLAG-tagged Tyr by shRNAs in the second generation (C) and miR-451 backbone (H) directly compared with the analogous sequence in the OshR platform. β-Tubulin is a loading control and GFP indicates proper expression of the shRNA vector.

FIG. 6 shows the design of an OshRNA that targets the *X. tropicalis* Tyrosinase using the design process depicted in FIG. 2. The following sequences are shown. 5RES-SphI (SEQ ID NO:9), 5RES-SalI (SEQ ID NO:10), 5RES-NsiI (SEQ ID NO:11), 3RES-SalI (SEQ ID NO:12), 3RES-NsiI (SEQ ID NO:13), 3RES-MluI (SEQ ID NO:14), Guide strand (SEQ ID NO:15), Pass. Strand Reversed (SEQ ID NO:16), Passenger strand (SEQ ID NO:17), 5Constant Stem (SEQ ID NO:18), Constant Stem Loop (SEQ ID NO:19), 3Constant Stem (SEQ NO:20), shRNA template oligo (SEQ ID NO:21), SphI-SalI shRNA final (SEQ ID NO:22), SphI-NsiI shRNA final (SEQ ID NO:23), SphI-MluI shRNA final (SEQ ID NO:24), SalI-NsiI shRNA final (SEQ ID NO:25), SalI-MluI shRNA final (SEQ ID NO:26), NsiI-MluI shRNA final (SEQ ID NO:27), pGSH0_FW3 (SEQ ID NO:28), pGSH0_RV2 (SEQ ID NO:29).

FIG. 7 provides the nucleic acid sequences for certain plasmids used in the experiments described in the exemplification. The following sequences are shown. Xt_Tyr_NM001103048_3×Flag (SEQ ID NO:30), pGSH0 (SEQ ID NO:31), pGSH0_OshRNA_Tyr1A (SEQ ID NO:32), pGSH0_OshRNA_Tyr2A (SEQ ID NO:33), pGSH0_OshRNA_Tyr1B (SEQ ID NO:34), pGSH0_OshRNA_Tyr2B (SEQ ID NO:35), pGSH0_OshRNA_Tyr3B (SEQ ID NO:36), pGSH0_OshRNA_Tyr1C (SEQ ID NO:37), pGSH0_OshRNA_Tyr2C (SEQ ID NO:38), pGSH0_OshRNA_Tyr3C (SEQ ID NO:39), pGSH0_OshRNA_Tyr4C (SEQ ID NO:40), pGSH0_OshRNA_Tyr5C (SEQ ID NO:41), pGSH0_OshRNA_Tyr6C (SEQ ID NO:42), pGSH0_mir451shRNA_Tyr2A (SEQ ID NO:43), pGSH0_mir451shRNA_Tyr6C (SEQ ID NO:44), pGSH0_2ndGenshRNA_Tyr2A (SEQ ID NO:45), pGSH0_2ndGenshRNA_Tyr6C (SEQ ID NO:46), GSH0_Nek2 OshR1 (SEQ ID NO:47), GSH0_Nek2 OshR2 (SEQ ID NO:48), GSH0_Nek2 OshR3 (SEQ ID NO:49), NEK2 wild type ORF with myc epitope (SEQ ID NO:50), NEK2 OshR1 SDM (SEQ ID NO:51), NEK2 OshR2 SDM (SEQ ID NO:52), NEK2 OshR3 SDM (SEQ ID NO:53).

DETAILED DESCRIPTION OF THE INVENTION

General

Provided herein are "organic shRNA" (OshRNA) that incorporate certain structural features that increase the likelihood that the desired guide strand is produced while reducing accumulation of passenger strands that might contribute to off-target effects. Also provided herein are nucleic acids encoding OshRNAs, kits, cells, and transgenic animals comprising such nucleic acids, as well as methods of making and using OshRNAs and/or nucleic acids encoding OshRNAs.

Although there are many web-based portals for shRNA design as well as multiple genome-wide repositories for purchasing sets of pre-designed shRNAs against a gene of interest, often an investigator may find that an entire panel of shRNAs purchased from these commercial sources fails to exhibit gene silencing even after controlling for transfection or transduction efficiency. To address this need for an effective alternative to currently available shRNAs, described herein are OshRNAs that are designed such that they incorporate certain structural features (e.g., a 2 nucleotide deletion at positions 11 and 12 of the passenger strand and a mismatch at position 19 of the passenger strand) such that they more closely mimic the structure of natural microRNAs, resulting in improved shRNA performance. A flowchart depicting an exemplary protocol for the design of OshRNAs is provided in FIG. 2, which can be used in combination with the worksheet provided in FIG. 6.

As described herein, OshRNAs perform well in specifying the production of the desired Guide strand because the structural features incorporated into their design more consistently suppress passenger strand accumulation. Furthermore OshRNAs are effective at targeting both the Open Reading Frame (ORF) and the 3' UnTranslated Region (3'UTR) of targeted vertebrate genes. Comparison of OshRNAs with current $2^{nd}$ generation shRNAs and miR-451-backbone shRNAs demonstrate the superior performance of OshRNAs compared to current shRNA designs. The OshRNAs described herein therefore provide an effective alternative to current shRNA designs.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, two nucleic acid sequences "complement" one another or are "complementary" to one another if they base pair one another at each position. Thus, the "reverse complement" of a specific nucleic acid sequence has a nucleic acid sequence that is able to form a Watson/Crick base pair with the specific nucleic acid sequence.

A "3' constant stem sequence" is the nucleic acid sequence immediately 3' of the passenger strand of a microRNA molecule. In certain embodiments, the 3' constant stem sequence is a miR-30a 3' constant stem sequence. Examples of miR-30a 3' constant stem sequences include those derived from mouse and human miR-30a (GCTGCCTACTGCCTCC, SEQ ID NO:54), and *Xenopus* miR-30a (GCTGCCAACTGCCTT, SEQ ID NO:55).

A "5' constant stem sequence" is the nucleic acid sequence immediately 5' of the guide strand of a microRNA molecule. In certain embodiments, the 5' constant stem sequence is a miR-30a 5' constant stem sequence. Examples of miR-30a 5' constant stem sequences include those derived from mouse and human miR-30a (GTTGACAGTGAGCGA, SEQ ID NO:56), and *Xenopus* miR-30a (CTGACAGTATGCGAC, SEQ ID NO:57).

A "constant stem loop sequence" is the loop-forming nucleic acid sequence immediately 3' of the guide strand and immediately 5' of the passenger strand of a microRNA molecule. In certain embodiments, the constant loop sequence is a miR-30a constant loop sequence. Examples of mi-30 constant loop sequences include those derived from mouse and human miR-30a (CCGTGAAGCCACAAATGGG, SEQ ID NO:58), and the *Xenopus* miR-30a (CCGTGAAGCAGTTGAAGGG, SEQ ID NO:59).

An "expression vector" is a vector which is capable of promoting expression of a nucleic acid incorporated therein. Typically, the nucleic acid to be expressed is "operably linked" to a transcriptional control element, such as a promoter and/or an enhancer, and is therefore subject to transcription regulatory control by the transcriptional control element.

The term "gene" is used broadly to refer to any nucleic acid associated with a biological function. The term "gene" applies to a specific genomic sequence, as well as to a cDNA or an mRNA encoded by that genomic sequence.

A nucleic acid sequence, domain or region is "immediately 5'" or "immediately 3'" to another sequence if the two sequences are part of the same nucleic acid molecule and if no bases separate the two sequences.

The term "isolated nucleic acid" refers to a polynucleotide of natural or synthetic origin or some combination thereof, which (1) is not associated with the cell in which the "isolated nucleic acid" is found in nature, and/or (2) is operably linked to a polynucleotide to which it is not linked in nature.

The terms "polynucleotide" and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

As used herein, the term "subject" refers to a human or a non-human animal, such as a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee).

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that may or may not be able to replicate autonomously or integrate into a chromosome of a host cell.

Organic Small Hairpin RNAs

In certain embodiments, provided herein are OshRNAs and nucleic acid molecules (e.g., single-stranded or double-stranded RNA or DNA molecules or a combination thereof) encoding OshRNAs (e.g., isolated nucleic acid molecules). Also provided herein are kits, cells, and transgenic animals comprising OshRNAs and nucleic acid molecules encoding OshRNAs.

In some embodiments, the OshRNA molecules provided herein include, in 5' to 3' order, a 5' constant stem sequence, a guide sequence, a constant stem loop, a passenger sequence and a 3' constant stem sequence. In certain embodiments, the 5' constant stem sequence, the guide sequence, the constant stem loop, the passenger sequence, and the 3' constant stem sequence are immediately adjacent to one another in the OshRNA molecule.

In some embodiments, the 5' constant stem sequence can be derived from any microRNA molecule. In certain embodiments, the 5' constant stem sequence includes the 15, 14, 13, 12, 11, or 10 nucleotides immediately 5' of the guide sequence of a microRNA molecule. In some embodiments, the 5' constant stem sequence is derived from a miR-30a 5' constant stem sequence (e.g., vertebrate miR-30a 5' constant stem sequence, such as a human, mouse, or *Xenopus* miR-30a 5' constant stem sequence). In some embodiments, the 5' constant stem sequence includes 1, 2, 3, 4, or 5 nucleotide differences compared to the 5' constant stem sequence from which it is derived.

The guide strand is the part of the OshRNA that targets the RNA-induced Silencing Complex (RISC) to a target nucleic acid sequence. In some embodiments, the guide sequence is a nucleic acid sequence of 19-29 nucleotides in length. In some embodiments, the guide sequence is at least 19, 20, 21, or 22 nucleotides in length. In some embodiments, the guide sequence is no more than 29, 28, 27, 26, 25, 24, 23, or 22 nucleotides in length. In some embodiments, the guide sequence is 22 nucleotides in length.

In certain embodiments, the OshRNA is designed to have thermodynamic properties that increase the likelihood that the guide strand becomes incorporated into the RISC complex. In some embodiments, the guide sequence contains an A/T/U rich region at its 5' end. In some embodiments, at least 2 of the 3, 3 of the 4, 3 of the 5, and/or 5 of the 6 nucleotides at the 5' end of the guide sequence are A, T, or U. In some embodiments, the two nucleotides at the 5' end of the guide sequence are A, T, or U. In some embodiments, the two nucleotides at the 5' end of the guide sequence are TT. In some embodiments, the guide sequence contains a C/G rich region at its 3' end. In some embodiments, at least 2 of the 3, 3 of the 4, 3 of the 5, and/or 5 of the 6 nucleotides at the 3' end of the guide sequence are C or G. In some embodiments, the two nucleotides at the 3' end of the guide sequence are C or G. In some embodiments, at least than 30%, 35%, 40%, or 45% of all the nucleotides in the guide strand are G or C.

In certain embodiments, the guide sequence is the reverse complement of a target nucleic acid sequence. In some embodiments, at least 18, 19, 20, 21, or 22 of the nucleotides of the guide sequence are the reverse complement the target nucleic acid sequence. In some embodiments, the target nucleic acid sequence is encoded by a target gene. In some embodiments, the target gene is a vertebrate gene (e.g., a human gene, a mouse gene, a *Xenopus* gene, a cow gene, a pig gene, a horse gene, a donkey gene, a goat gene, a camel gene, a cat gene, a dog gene, a guinea pig gene, a rat gene, a sheep gene, a monkey gene, a gorilla gene, or a chimpanzee gene). In some embodiments, the nucleotide sequence at positions 12-21 are the reverse complement of a target nucleic acid sequence.

In some embodiments, the nucleotide sequence at positions 12-21 do not complement a sequence encoded by any non-target gene expressed by the species that expresses the target gene. In some embodiments, the target nucleic acid is in a 3' untranslated region or an open reading frame of a target mRNA. Whether the guide sequence complements a sequence encoded by a non-target gene expressed by the species that expresses the target gene can be determined by querying the guide sequence against a nucleic acid sequence database (e.g., the RefSeq RNA database of the target animal) using standard sequence comparison tools (e.g., BLAST-N).

In some embodiments, the constant stem loop can be derived from any miRNA molecule. In some embodiments, the constant stem loop is a miR-30a constant stem loop (e.g., vertebrate miR-30a constant stem loop, such as a human, mouse, or *Xenopus* miR-30a constant stem loop). In some embodiments, the constant stem loop sequence includes 1, 2, 3, 4, or 5 nucleotide differences compared to the 5' constant stem loop sequence from which it is derived.

The passenger sequence of the OshRNA molecule has partial complementarity to the guide strand such that the OshRNA forms the secondary structure necessary to enter the cellular RNAi process, but incorporates certain structural features that reduce the likelihood of the passenger strand becoming incorporated into the RISC complex. In some embodiments, the passenger sequence is the reverse complement of the guide sequence except for two missing nucleotides and a single non-complementing nucleotide. In some embodiments, the missing nucleotides are at positions 10 and 11, 11 and 12, or 12 and 13 of the passenger strand. In some embodiments, the non-complementing nucleotide is at position 19 of the passenger strand (the position that would complement position 4 of the guide strand if it were complementary). The nucleotide positions provided herein are counted in a 5' to 3' direction and positions in which nucleotides are missing are included in the count, as depicted, for example, in FIG. 3C.

In some embodiments, the 3' constant stem sequence can be derived from any microRNA molecule. In certain embodiments, the 3' constant stem sequence includes the 15, 14, 13, 12, 11, or 10 nucleotides immediately 3' of the passenger sequence of a microRNA molecule. In some embodiments, the 3' constant stem sequence is derived from a miR-30a 3' constant stem sequence (e.g., vertebrate miR-30a 3' constant stem sequence, such as a human, mouse, or *Xenopus* miR-30a 3' constant stem sequence). In some embodiments, the 3' constant stem sequence includes 1, 2, 3, 4, or 5 nucleotide differences compared to the 3' constant stem sequence from which it is derived.

In some embodiments, the OshRNA is encoded by a nucleic acid molecule (e.g., an RNA molecule, a DNA molecule, or a nucleic acid molecule that includes both RNA and DNA).

For example, in some embodiments, the OshRNA is encoded by a single-stranded RNA molecule (e.g., a single-stranded RNA molecule containing a hairpin secondary structure encoded by the OshRNA sequence). Such a single-stranded RNA molecule can be, for example, an mRNA molecule. In some embodiments, the OshRNA sequence is located in an intron or a 3' untranslated region of an mRNA molecule. In some embodiments, the nucleic acid molecule is part of an RNA vector (e.g., a lentiviral vector or a retroviral vector).

In some embodiments, the nucleic acid molecule is a double-stranded DNA molecule. Such a double-stranded DNA molecule can be, for example, isolated, integrated into the genome of a cell, or extra-chromosomal. In some embodiments, the nucleic acid molecule is a part of a DNA vector (e.g., a plasmid or a viral vector). In some embodiments, the nucleic acid molecule is an expression vector. In some embodiments, the expression vector expresses an RNA molecule that includes the OshRNA sequence. In certain embodiments the RNA molecule is an mRNA molecule. In some embodiments, the OshRNA sequence is located in an intron or a 3' untranslated region of the mRNA molecule.

In some embodiments, the nucleic acid encoding the OshRNA is present in a cell. The cell can be, for example, a human cell or a non-human cell. In some embodiments, the nucleic acid encoding the OshRNA is present in a vertebrate cell, such as a mammalian cell including non-primate cells (e.g., cells from a cow, pig, horse, donkey, goat, camel, cat, dog, guinea pig, rat, mouse, sheep) and primate cells (e.g., a cell from a monkey, gorilla, chimpanzee). The cell containing the OshRNA can be a cell in an organism, primary cell outside of an organism, or a cell line. Examples of cell lines in which the nucleic acids described herein can be present include, but are not limited to, P19 cells, HUVAC cells, 293-T cells, 3T3 cells, 721 cells, 9L cells, A2780 cells, A172 cells, A253 cells, A431 cells, CHO cells, COS-7 cells, HCA2 cells, HeLa cells, Jurkat cells, NIH-3T3 cells, and Vero cells.

Methods of introducing a nucleic acid into a cell are well known in the art. For example, nucleic acids can be delivered to cells in culture, ex vivo, and in vivo. The delivery of nucleic acids can be by any technique known in the art including viral mediated gene transfer, liposome mediated gene transfer, direct injection into a target tissue, organ, or tumor, and injection into vasculature which supplies a target tissue or organ. Polynucleotides can be contacted to cells in any suitable formulations known in the art. These can be as virus particles, as naked DNA, in liposomes, in complexes with polymeric carriers, etc. Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

In some embodiments, the nucleic acid encoding the OshRNA is present a non-human animal. The animal can be, for example, a mammal, including non-primates (e.g., a cow, pig, horse, donkey, goat, camel, cat, dog, guinea pig, rat, mouse, sheep) and primates (e.g., a monkey, gorilla, chimpanzee). In certain embodiments the animal is a mouse. In some embodiments, the nucleic acid is integrated into the genomic DNA of the animal. In some embodiments, the nucleic acid encoding the OshRNA is present as part of a transgene. Any appropriate method known in the art can be used to generate the non-human animal containing the nucleic acid encoding the OshRNA (e.g., pronuclear injection of the nucleic acid into mouse embryonic cells and/or incorporation of the nucleic acid into the genomic DNA of an embryonic stem cell using homologous recombination). In some embodiments, the nucleic acid is extra-chromosomal.

In some embodiments, the nucleic acid encoding the OshRNA is a component in a kit for silencing a target gene. Such a kit may include, for example, one or more OshRNAs, reagents for transfecting the OshRNAs into cells and/or instructions for use. In some embodiments, the kit includes multiple OshRNAs that target different sequences on the same target gene. In some embodiments, the kit contains a plurality of different OshRNAs that target different genes (e.g., multiple genes in a pathway or genes in related pathways).

In some embodiments, the OshRNA is encoded by a library of nucleic acid molecules encoding a plurality of different OshRNA molecules specific for different targets. For example, in some embodiments such a library contains nucleic acid molecules encoding at least 10, 20, 30, 40, 50, 60, 70, 80, 90, or 100 different OshRNAs specific for at least 10, 20, 30, 40, 50, 60, 70, 80, 90, or 100 different targets. In some embodiments, the different OshRNAs encoded by the library are specific for target genes in a single cellular pathway. In some embodiments, the different OshRNAs encoded by the library are specific for target genes in related cellular pathways. Such libraries can be useful, for example, in screening assays to identify potential therapeutic targets.

Inhibition of Target Genes using Organic Small Hairpin RNAs

In certain embodiments, provided herein is a method of inhibiting expression of a target nucleic acid in a cell comprising contacting the cell with a nucleic acid molecule described herein. In some embodiments, the cell is a vertebrate cell, such as a mammalian cell including non-primate cells (e.g., cells from a cow, pig, horse, donkey, goat, camel, cat, dog, guinea pig, rat, mouse, sheep) and primate cells (e.g., a cell from a monkey, gorilla, chimpanzee). In some embodiments, the cell is present in an organism, is a primary cell outside of an organism, or is a cell line. Examples of cell lines in which the nucleic acids described herein can be present include, but are not limited to, P19 cells, HUVAC cells, 293-T cells, 3T3 cells, 721 cells, 9L cells, A2780 cells, A172 cells, A253 cells, A431 cells, CHO cells, COS-7 cells, HCA2 cells, HeLa cells, Jurkat cells, NIH-3T3 cells, and Vero cells. The nucleic acids described herein can be delivered to cells in vivo, ex vivo, or in vitro.

In certain embodiments, provided herein is a method of inhibiting expression of a target nucleic acid in a subject comprising administering to the subject a nucleic acid molecule described herein. In some embodiments, the subject is a vertebrate. In some embodiments, the subject is a mammal. In some embodiments, the subject is a human.

In the present methods, an OshRNA can be administered to the subject or cell, for example, as naked RNA, in combination with a delivery reagent, and/or as a nucleic acid comprising sequences that encode the OshRNA. In some embodiments, the nucleic acid comprising sequences that encode OshRNA are delivered within vectors, e.g., plasmid, viral, and bacterial vectors. Any nucleic acid delivery method known in the art can be used in the methods described herein. Suitable delivery reagents include, but are not limited to, e.g., the Mirus Transit TKO lipophilic reagent, lipofectin, lipofectamine, cellfectin, polycations (e.g., polylysine), atelocollagen, nanoplexes, and liposomes. The use of atelocollagen as a delivery vehicle for nucleic acid molecules is described in Minakuchi et al. Nucleic Acids Res., 32(13):e109 (2004); Hanai et al. Ann NY Acad Sci., 1082:9-17 (2006); and Kawata et al. Mol Cancer Ther., 7(9):2904-12 (2008); each of which is incorporated herein in their entirety.

In some embodiments of the methods described herein, liposomes are used to deliver an OshRNA to a subject or cell. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann Rev. Biophys. Bioeng. 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives, e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

When administered to a subject, the nucleic acid encoding an OshRNA can be part of a pharmaceutical composition. Pharmaceutical compositions described herein include a nucleic acid encoding an OshRNA, a pharmaceutically acceptable salt thereof, and/or a pharmaceutically acceptable carrier or vehicle. The pharmaceutical compositions may further include additional therapeutic agents.

All publications, including patents, applications, and GenBank Accession numbers mentioned herein are hereby incorporated by reference in their entirety as if each individual publication or patent was specifically and individually indicated to be incorporated by reference. In case of conflict, the present application, including any definitions herein, will control.

The invention now being generally described, it will be more readily understood by reference to the following examples, which are included merely for purposes of illustration of certain aspects and embodiments of the present invention, and are not intended to limit the invention.

EXEMPLIFICATION

Example 1

Design of OshRNAs

An exemplary method for designing OshRNAs is provided in FIG. 2. Design of the OshRNA begins by taking the complete mRNA sequence of the gene of interest and determining if the mRNA has a stable and extensive 3'UTR that most metazoan genes possess. Targeting a gene's 3'UTR increases the probability that an shRNA will not encounter refractory mRNA sequences, however ORFs are the next logical sequence to examine should a 3'UTR sequence be unavailable or too short (<50 bp). Next, a sequence-gazing method is conducted to pick an optimal sequence base composition (FIG. 2A, Step 3-4), and a BLAST-query approach is used to minimize off-target sequences (Step 5-7). An iterative procedure is followed to find optimal candidate GUIDE strand sequences of 22nt long. A PASSENGER strand sequence is then designed by taking the reverse complement of the Guide strand, deleting bases 11 and 12, and then mutating base 19 of Passenger strand so it is mismatched with Guide strand. These GUIDE and PASSENGER strand sequences are typed into a spreadsheet that concatenates the sequences into a ~90 bp single-stranded DNA template that is ordered from an oligonucleotide vendor (see FIG. 6).

A set of primers that contain restriction enzyme (RE) sites are used to carry out a PCR reaction to generate an amplicon that can be cloned directionally into an animal expression vector. The OshRNA sequence is cloned into a multiple cloning site of an intron that bisects GFP driven by a strong CMV promoter (FIG. 2B). This format allows the maturation of the shRNA to occur independently of GFP expression, and further mimics the natural occurrence of many mammalian miRNAs that reside in the introns of host genes. The OshRNA construct will also function in other expression vectors into which the OshRNAs is inserted into the 3'UTR. Proper construction of the expression vector is verified by sequencing all plasmids and transfection-grade quality plasmids are prepared by ion exchange columns such as commercial midiprep kit. Plasmids are then introduced into cells using standard transfection protocols.

Example 2

The OshR Platform Enhances Guide Strand Accumulation Over the Passenger Strand

Current shRNA lack internal bulges and instead utilize a complete duplex that places the guide strand on the 3' arm of the hairpin. In contrast, the OshRNAs described herein include features similar to those in naturally occurring microRNAs that direct major accumulation of the guide strand instead of the passenger strand (FIG. 1). The OshR scheme places a programmable Guide strand on the 5' arm of the hairpin, and certain mismatched bases are present within the stem and the loop (FIG. 3B). Next, the Passenger strand was placed on the 3' arm of the hairpin, but instead of a perfect duplex, a mismatched base at the 3' end of the Passenger strand and two bases deleted in the middle were engineered.

To test whether the OshR platform would encourage Guide strand production while suppressing passenger accumulation, 10 OshRNAs against the *X. tropicalis* Tyr gene were constructed and each plasmid transfected into HEK293T cells. Equivalent, highly efficient transfection occurred for all plasmids as judged by >90% of the cells brightly fluorescing green (data not shown). By Northern blotting with probes that either detected the Guide strand or the Passenger strand, strong accumulation of the Guide strand sequence and very low or negligible production of the passenger strand was consistently detected (FIG. 3D). The size of the shRNA signal is consistent with mature small RNAs that would be incorporated into the RISC (21-23 nt long). These data support the conclusion that the OshRNA design enforces predominant Guide strand production while significantly preventing passenger strands from accumulating and causing off-target effects.

Example 3

Targeting the 3' UTR of a Transcript Increases the Probability of shRNA Efficiency Any Guide strand with perfect complementarity to a target transcript should direct RISC to degrade the target mRNA. However, certain mRNA sites can be refractory to RNAi in the cell because the mRNA secondary structure, stalled ribosomes, and other RNA binding proteins can block the RISC. These factors can be difficult to predict. To test the gene silencing efficacy of three OshRNAs targeting the ORF of the mouse NIMA related protein kinase 2 (NEK2) gene, the OshRNA encoding plasmids were transfected along with a myc-tagged NEK2 into HEK293T cells (FIG. 4A). All three of the OshRs against NEK2 exhibited strong knockdown of the myc-tagged NEK2 transgene, and this knockdown could be circumvented with rescue constructs of NEK2 which had neutral mutations that altered the mRNA from base pairing perfectly with the shRNA. By validating these OshRNAs with epitope-tagged wild-type and rescue mutant transgenes (because antibodies are not always available for endogenous genes), a bank of tools have been established that enable knocking down endogenous wild-type NEK2, testing for function, and then rescuing the function with shRNA-resistant transgenes. Thus, all the target sites tested for NEK2 yielded effective gene knockdown by the organic shRNAs.

However, only 2 out of 7 OshRNAs targeting the ORF of Tyr were able to elicit strong gene silencing despite the confirmation that sufficient guide strand was being produced (FIG. 3D), and these two ORF-targeting OshRNAs targeted the same general locale of the Tyr mRNA. Strikingly, 3 out of 4 shRNAs targeting the 3'UTR significantly downregulated Tyr protein expression. In every transfection experiment, nearly equal expression of each of the OshRNA constructs in the HEK293T cells was confirmed as judged by GFP fluorescence (data not shown) and western blot signal (FIG. 4B). Although it was unknown if the region in the ORF targeted by Tyr OshRNAs 1C and 2C is less likely to form secondary structures, the fact that the majority of OshRNAs targeting the 3'UTR were highly effective at gene silencing is consistent with the natural targeting proficiency of miRNAs against the 3'UTR of their targets.

Example 4

Comparison of the OshR Platform to Second Generation and miR-451 Backbone shRNA Designs To directly compare specific Guide strand production and targeting efficacy between the OshRNA platform and other shRNA formats, two OshRNAs (2A and 6C, FIG. 3C) were remade as $2^{nd}$ generation shRNAs. This was done by first placing the Guide strands of 2A and 6C onto the 3' arm and setting the duplex to be completely complementary (FIG. 5). These $2^{nd}$ generation shRNAs were cloned into the intron cloning site of the GFP expressing vector, the shRNA vectors were co-transfected along with the 3×FLAG tagged Tyr transgene into HEK293T cells. Both $2^{nd}$ generation shRNAs generated the Guide strand comparably to OshR- NAs (FIG. 5E); but both Guide strands from the second generation format were mainly 22nt long and about Int shorter than OshR Guide strands. Nearly all Guide strands generated by the OshR platform that were tested by Northern blots accumulate as a 23-24nt long (FIG. 3D), which is also the most abundant length of natural miR-30a.

Western blots indicated that the shTyr2A was equally robust at silencing the 3×FLAG-Tyr transgene regardless of whether it was in a $2^{nd}$ generation or OshRNA format. However, the shTyr6C was more effective at gene silencing when expressed from the OshRNA format compared to the second generation shRNA (FIG. 5G), despite the fact that there was nearly equal Northern blot signal from the OshRNA and $2^{nd}$ generation shTyr6C Guide strands (FIG. 5E). Between sequences, shTyr2A was consistently more effective at silencing the transgene to nearly undetectable levels, which may be attributed to the sequence of shTyr2A being less G/C rich than shTyr6C. It is likely that underlying base compositions within siRNAs and miRNAs influence the multiple-turnover activity of Ago proteins, and if a particular shRNA is so effective at silencing (like shTyr2A), it does not matter whether it is expressed from a $2^{nd}$ generation shRNA backbone or the more organic OshRNA backbone. However, with shRNAs with lower targeting efficiency (like shTyr6C), the OshRNA enhances targeting efficacy because the longer length of the major Guide strand contributes to stronger gene silencing.

Next, the OshRNA platform was compared to a newly emerging shRNA platform that uses the exemplary backbone of miR-451, a vertebrate-specific miRNA with a non-canonical stem loop that skips Dicer processing and instead matures through the Slicer activity of Ago2. The short stem of miR-451 directs only the 5' arm to be incorporated into RISC as the guide strand.

A miR-451-backbone shRNAs were created for the Tyr-targeting sequences 2A and 6C by maintaining necessary lower stem sequences and secondary structure features of miR-451 (FIG. 5E). There was more readily detected signal for the shTyr-6C mature shRNA compared to the shTyr-2A when inserted in the miR451 backbone constructs as well as the OshRNA backbone. However, the OshRNA backbone consistently yielded an order of magnitude greater accumulation of the mature guide strand than the miR-451 backbone (FIG. 5G), despite the fact that fluorescence and western blotting signals of GFP from miR-451 backbone vectors were greater than the OshRNA vectors (FIG. 5F). This suggested that the poor accumulation of Guide strands from the miR-451-backbone is more likely explained by issues with incorporation into RISC rather than the miR-451 backbone effects on the precursor RNA, which contributes effectively to GFP expression.

The knockdown capacities of the organic shRNAs were compared with those of the miR-451 backbone via co-transfection of the shRNA plasmid and the 3×FLAG tagged Tyr into HEK293T cells. Although some shRNAs like OshR-2C accumulate poorly but can efficiently trigger gene silencing (see FIGS. 3D and 4B), appreciable gene silencing was not observed by shTyr-2A and -6C in the miR-451 backbone (FIGS. 5G and 5H). These results suggest that the OshRNA platform is more flexible for shRNA design compared to the miR-451-based platform because it does not constrain the shRNA to only enter Ago2, but rather may allow for the shRNA to accumulate to more significant levels in the other Argonaute proteins.

We claim:

1. An isolated nucleic acid molecule, comprising a nucleic acid sequence encoding an organic shRNA (OshRNA) sequence comprising, in 5' to 3' order, a 5' constant stem sequence, a guide sequence, a constant stem loop, a passenger sequence, and a 3' constant stem sequence; wherein:

the guide sequence is a nucleic acid sequence of 22 nucleotides in length that is the reverse complement of a target nucleic acid sequence; and the passenger sequence is a nucleic acid sequence that is the reverse complement of the guide sequence but wherein the complementary nucleotides at positions 11 and 12 are absent and wherein a non-complementing nucleotide is at position 19.

2. The isolated nucleic acid molecule of claim 1, wherein the 5' constant stem sequence, the constant stem loop, and the 3' constant stem sequence are a miR-30a 5' constant stem sequence, a miR-30a constant stem loop, and a miR-30a 3' constant stem sequence, respectively.

3. The isolated nucleic acid molecule of claim 2, wherein the miR-30a 5' constant stem sequence, the miR-30a constant stem loop, and the miR-30a 3' constant stem sequence are from human miR-30a , mouse miR-30a, or Xenopus miR-30a.

4. The isolated nucleic acid molecule of claim 1, wherein at least 3 of the 4 nucleotides at the 5' end of the guide sequence are A, T, or U.

5. The isolated nucleic acid molecule of claim 1, wherein at least 3 of the 4 nucleotides at the 3' end of the guide sequence are G or C.

6. The isolated nucleic acid molecule of claim 1, wherein the target nucleic acid sequence is in a 3' untranslated region of a target mRNA.

7. The isolated nucleic acid molecule of claim 1, wherein the target nucleic acid sequence is in an open reading frame of a target mRNA.

8. The isolated nucleic acid molecule of claim 1, wherein the isolated nucleic acid molecule is a single-stranded RNA molecule.

9. The isolated nucleic acid of claim 1, wherein the isolated nucleic acid molecule is a double-stranded DNA molecule.

10. The isolated nucleic acid molecule of claim 9, wherein the isolated nucleic acid molecule is an expression vector.

11. The isolated nucleic acid molecule of claim 10, wherein the expression vector expresses an RNA molecule that comprises the OshRNA sequence.

12. The isolated nucleic acid molecule of claim 11, wherein the expressed RNA molecule is an mRNA molecule and the OshRNA sequence is located in an intron or a 3' untranslated region of the mRNA molecule.

13. A cell, comprising a nucleic acid molecule, comprising a nucleic acid sequence encoding organic shRNA (OshRNA) comprising, in 5' to 3' order, a 5' constant stem sequence, a guide sequence, a constant stem loop, a passenger sequence, and a 3' constant stem sequence; wherein:

the guide sequence is a nucleic acid sequence of 22 nucleotides in length that is the reverse complement of a target nucleic acid sequence; and the passenger sequence is a nucleic acid sequence that is the reverse complement of the guide sequence but wherein the complementary nucleotides at positions 11 and 12 are absent and wherein a non-complementing nucleotide is at position 19.

14. The cell of claim 13, wherein the 5' constant stem sequence, the constant stem loop, and the 3' constant stem sequence are a miR-30a 5' constant stem sequence, a miR-30a constant stem loop, and a miR-30a 3' constant stem sequence, respectively.

15. The cell of claim 14, wherein the miR-30a 5' constant stem sequence, the miR-30a constant stem loop, and the miR-30a 3' constant stem sequence are from human miR-30a, mouse miR-30a, or Xenopus miR-30a.

16. The cell of claim 13, wherein at least 3 of the 4 nucleotides at the 5' end of the guide sequence are A, T, or U.

17. The cell of claim 13, wherein at least 3 of the 4 nucleotides at the 3' end of the guide sequence are G or C.

18. The cell of claim 13, wherein the target nucleic acid sequence is in a 3' untranslated region of a target mRNA.

19. The cell of claim 13, wherein the target nucleic acid sequence is in an open reading frame of a target mRNA.

20. The cell of claim 13, wherein the nucleic acid molecule is a single-stranded RNA molecule.

21. The cell of claim 13, wherein the nucleic acid molecule is a double-stranded DNA molecule.

22. The cell of claim 21, wherein the nucleic acid molecule is an expression vector.

23. The cell of claim 22, wherein the expression vector expresses an RNA molecule that comprises the OshRNA sequence.

24. The cell of claim 23, wherein the expressed RNA molecule is an mRNA molecule and the OshRNA sequence is located in an intron or a 3' untranslated region of the mRNA molecule.

25. The cell of claim 21, wherein the nucleic acid molecule is integrated into the genomic DNA of the cell.

26. A transgenic non-human animal, comprising a nucleic acid molecule, comprising a nucleic acid sequence encoding organic shRNA (OshRNA) comprising, in 5' to 3' order, a 5' constant stem sequence, a guide sequence, a constant stem loop, a passenger sequence, and a 3' constant stem sequence; wherein:

the guide sequence is a nucleic acid sequence of 22 nucleotides in length that is the reverse complement of a target nucleic acid sequence; and the passenger sequence is a nucleic acid sequence that is the reverse complement of the guide sequence but wherein the complementary nucleotides at positions 11 and 12 are absent and wherein a non-complementing nucleotide is at position 19.

27. The transgenic non-human animal of claim 26, wherein the 5' constant stem sequence, the constant stem loop, and the 3' constant stem sequence are a miR-30a 5' constant stem sequence, a miR-30a constant stem loop, and a miR-30a 3' constant stem sequence, respectively.

28. The transgenic non-human animal of claim 27, wherein the miR-30a 5' constant stem sequence, the miR-30a constant stem loop, and the miR-30a 3' constant stem sequence are from human miR-30a, mouse miR-30a, or Xenopus miR-30a.

29. The transgenic non-human animal of claim 26, wherein at least 3 of the 4 nucleotides at the 5' end of the guide sequence are A, T, or U.

30. The transgenic non-human animal of claim 26, wherein at least 3 of the 4 nucleotides at the 3' end of the guide sequence are G or C.

31. The transgenic non-human animal of claim 26, wherein the target nucleic acid sequence is in a 3' untranslated region of a target mRNA.

32. The transgenic non-human animal of claim 26, wherein the target nucleic acid sequence is in an open reading frame of a target mRNA.

33. The transgenic non-human animal of claim 26, wherein the animal is a mouse.

34. The transgenic non-human animal of claim 26, wherein the nucleic acid molecule is integrated into the genome of the animal.

35. The transgenic non-human animal of claim 34, wherein the animal expresses an RNA molecule that comprises the OshRNA sequence.

36. The transgenic non-human animal of claim 35, wherein the expressed RNA molecule is an mRNA molecule and the OshRNA sequence is located in an intron or a 3' untranslated region of the mRNA molecule.

37. A method of inhibiting expression of a target nucleic acid in a cell, comprising contacting the cell with an isolated nucleic acid molecule of claim 1, wherein the target nucleic acid molecule comprises the target nucleic acid sequence.

38. The method of claim 37, wherein the isolated nucleic acid molecule is a single-stranded RNA molecule.

39. The method of claim 37, wherein the isolated nucleic acid molecule is a double-stranded DNA molecule.

40. The method of claim 39, wherein the isolated nucleic acid molecule is an expression vector.

41. The method of claim 40, wherein the expression vector expresses an RNA molecule that comprises the OshRNA sequence.

42. The method of claim 41, wherein the expressed RNA molecule is an mRNA molecule and the OshRNA sequence is located in an intron or a 3' untranslated region of the mRNA molecule.

43. The method of claim 37, wherein the cell is a human cell.

44. The method of claim 37, wherein the method is performed in vitro.

45. The method of claim 37, wherein the method is performed in vivo.

46. A kit, comprising an isolated nucleic acid molecule of claim 1.

47. The kit of claim 46, wherein the isolated nucleic acid molecule is a single-stranded RNA molecule.

48. The kit of claim 46, wherein the isolated nucleic acid molecule is a double-stranded DNA molecule.

49. The kit of claim 48, wherein the isolated nucleic acid molecule is an expression vector.

50. The kit of claim 49, wherein the expression vector expresses an RNA molecule that comprises the OshRNA sequence.

51. The kit of claim 50, wherein the expressed RNA molecule is an mRNA molecule and the OshRNA sequence is located in an intron or a 3' untranslated region of the mRNA molecule.

52. An OshRNA library, comprising at least 10 different isolated nucleic acid molecules of claim 1.

53. The library of claim 52, comprising at least 100 different isolated nucleic acid molecules of claim 1.

54. The library of claim 52, wherein the isolated nucleic acid molecules are single-stranded RNA molecules.

55. The library of claim 52, wherein the isolated nucleic acid molecules are double-stranded DNA molecules.

56. The library of claim 55, wherein the isolated nucleic acid molecules are expression vectors.

57. The library of claim 56, wherein the expression vectors express RNA molecules that comprise the OshRNA sequence.

58. The library of claim 57, wherein the expressed RNA molecules are mRNA molecules and the OshRNA sequence is located in an intron or a 3' untranslated region of the mRNA molecules.

* * * * *

SEQUENCE LISTING

```
<160> NUMBER OF SEQ ID NOS: 59

<210> SEQ ID NO 1
<211> LENGTH: 93
<212> TYPE: DNA
<213> ORGANISM: Artificial
<220> FEATURE:
<223> OTHER INFORMATION: Mouse miR-30a
<220> FEATURE:
<221> NAME/KEY: misc_feature
<222> LOCATION: (9)..(9)
<223> OTHER INFORMATION: N at position 9 is uracil
<220> FEATURE:
<221> NAME/KEY: misc_feature
<222> LOCATION: (17)..(17)
<223> OTHER INFORMATION: N at position 17 is uracil
<220> FEATURE:
<221> NAME/KEY: misc_feature
<222> LOCATION: (19)..(19)
<223> OTHER INFORMATION: N at position 19 is uracil
<220> FEATURE:
<221> NAME/KEY: misc_feature
<222> LOCATION: (25)..(25)
<223> OTHER INFORMATION: N at position 25 is uracil
<220> FEATURE:
<221> NAME/KEY: misc_feature
<222> LOCATION: (28)..(28)
<223> OTHER INFORMATION: N at position 28 is uracil
<220> FEATURE:
<221> NAME/KEY: misc_feature
<222> LOCATION: (33)..(33)
<223> OTHER INFORMATION: N at position 33 is uracil
<220> FEATURE:
<221> NAME/KEY: misc_feature
<222> LOCATION: (40)..(40)
<223> OTHER INFORMATION: N at position 40 is uracil
<220> FEATURE:
```

<221> NAME/KEY: misc_feature
<222> LOCATION: (42)..(42)
<223> OTHER INFORMATION: N at position 42 is uracil
<220> FEATURE:
<221> NAME/KEY: misc_feature
<222> LOCATION: (54)..(54)
<223> OTHER INFORMATION: N at position 54 is uracil
<220> FEATURE:
<221> NAME/KEY: misc_feature
<222> LOCATION: (59)..(61)
<223> OTHER INFORMATION: N at positions 59-61 is uracil
<220> FEATURE:
<221> NAME/KEY: misc_feature
<222> LOCATION: (65)..(65)
<223> OTHER INFORMATION: N at position 65 is uracil
<220> FEATURE:
<221> NAME/KEY: misc_feature
<222> LOCATION: (70)..(70)
<223> OTHER INFORMATION: N at position 70 is uracil
<220> FEATURE:
<221> NAME/KEY: misc_feature
<222> LOCATION: (72)..(74)
<223> OTHER INFORMATION: N at positions 72-74 is uracil
<220> FEATURE:
<221> NAME/KEY: misc_feature
<222> LOCATION: (80)..(80)
<223> OTHER INFORMATION: N at position 80 is uracil
<220> FEATURE:
<221> NAME/KEY: misc_feature
<222> LOCATION: (84)..(84)
<223> OTHER INFORMATION: N at position 84 is uracil
<220> FEATURE:
<221> NAME/KEY: misc_feature
<222> LOCATION: (87)..(87)
<223> OTHER INFORMATION: N at position 87 is uracil

<400> SEQUENCE: 1
gttgacagng agcgacngna aacanccncg acnggaagcn gngaagccac aaangggcnn 60
ncagncggan gnnngcagcn gccnacngcc tcc 93

<210> SEQ ID NO 2
<211> LENGTH: 91
<212> TYPE: DNA
<213> ORGANISM: Artificial
<220> FEATURE:
<223> OTHER INFORMATION: Xenopus miR-30a
<220> FEATURE:
<221> NAME/KEY: misc_feature
<222> LOCATION: (8)..(8)
<223> OTHER INFORMATION: N at position 8 is uracil
<220> FEATURE:
<221> NAME/KEY: misc_feature
<222> LOCATION: (10)..(10)
<223> OTHER INFORMATION: N at position 10 is uracil
<220> FEATURE:
<221> NAME/KEY: misc_feature
<222> LOCATION: (16)..(16)
<223> OTHER INFORMATION: N at position 16 is uracil
<220> FEATURE:
<221> NAME/KEY: misc_feature
<222> LOCATION: (18)..(18)
<223> OTHER INFORMATION: N at position 18 is uracil
<220> FEATURE:
<221> NAME/KEY: misc_feature
<222> LOCATION: (24)..(24)
<223> OTHER INFORMATION: N at position 24 is uracil
<220> FEATURE:
<221> NAME/KEY: misc_feature
<222> LOCATION: (27)..(27)
<223> OTHER INFORMATION: N at position 27 is uracil
<220> FEATURE:
<221> NAME/KEY: misc_feature
<222> LOCATION: (32)..(32)
<223> OTHER INFORMATION: N at position 32 is uracil
<220> FEATURE:
<221> NAME/KEY: misc_feature
<222> LOCATION: (39)..(39)
<223> OTHER INFORMATION: N at position 39 is uracil
<220> FEATURE:
<221> NAME/KEY: misc_feature
<222> LOCATION: (41)..(41)
<223> OTHER INFORMATION: N at position 41 is uracil
<220> FEATURE:
<221> NAME/KEY: misc_feature
<222> LOCATION: (49)..(50)
<223> OTHER INFORMATION: N at positions 49-50 is uracil
<220> FEATURE:
<221> NAME/KEY: misc_feature
<222> LOCATION: (58)..(60)
<223> OTHER INFORMATION: N at positions 58-60 is uracil
<220> FEATURE:
<221> NAME/KEY: misc_feature
<222> LOCATION: (64)..(64)
<223> OTHER INFORMATION: N at position 64 is uracil
<220> FEATURE:
<221> NAME/KEY: misc_feature
<222> LOCATION: (69)..(69)
<223> OTHER INFORMATION: N at position 69 is uracil
<220> FEATURE:
<221> NAME/KEY: misc_feature
<222> LOCATION: (71)..(73)
<223> OTHER INFORMATION: N at positions 71-73 is uracil
<220> FEATURE:
<221> NAME/KEY: misc_feature
<222> LOCATION: (79)..(79)
<223> OTHER INFORMATION: N at position 79 is uracil
<220> FEATURE:
<221> NAME/KEY: misc_feature
<222> LOCATION: (86)..(86)
<223> OTHER INFORMATION: N at position 86 is uracil

<400> SEQUENCE: 2
ctgacagnan gcgacngnaa acanccncga cnggaagcng ngaagcagnn gaagggcnnn 60
cagncagang nnngcagcng ccaacngcct t 91

<210> SEQ ID NO 3
<211> LENGTH: 20
<212> TYPE: DNA
<213> ORGANISM: Artificial
<220> FEATURE:
<223> OTHER INFORMATION: OshR passenger strand sequence

<400> SEQUENCE: 3
cgtgaacaaa tgtatagtaa 20

<210> SEQ ID NO 4
<211> LENGTH: 22
<212> TYPE: DNA
<213> ORGANISM: Artificial
<220> FEATURE:
<223> OTHER INFORMATION: Guide strand sequence

<400> SEQUENCE: 4
ttagtataca aatttgttca cg 22

<210> SEQ ID NO 5
<211> LENGTH: 95
<212> TYPE: DNA
<213> ORGANISM: Artificial
<220> FEATURE:
<223> OTHER INFORMATION: OshR 2A
<220> FEATURE:
<221> NAME/KEY: misc_feature
<222> LOCATION: (51)..(52)
<223> OTHER INFORMATION: N at positions 51-52 is uracil

<400> SEQUENCE: 5

-continued tgctgacagt atgcgactta gtatacaaat ttgttcacgc cgtgaagcag nngaagggcg 60
tgaacaaatg tatagtaagc tgccaactgc cttcg 95

<210> SEQ ID NO 6
<211> LENGTH: 95
<212> TYPE: DNA
<213> ORGANISM: Artificial
<220> FEATURE:
<223> OTHER INFORMATION: OshR 6C
<220> FEATURE:
<221> NAME/KEY: misc_feature
<222> LOCATION: (51)..(52)
<223> OTHER INFORMATION: N at positions 51-52 is uracil

<400> SEQUENCE: 6
tgctgacagt atgcgacttg ggaaagtccc agtgggccgc cgtgaagcag nngaagggcg 60
gcccactcac tttcctaagc tgccaactgc cttcg 95

<210> SEQ ID NO 7
<211> LENGTH: 95
<212> TYPE: DNA
<213> ORGANISM: Artificial
<220> FEATURE:
<223> OTHER INFORMATION: Second generation shTyr-2A

<400> SEQUENCE: 7
tgctgacagt gagcgccgtg aacaaatttg tatactaata gtgaagccac agatgtatta 60
gtatacaaat ttgttcacgt tgcctactgc cttcg 95

<210> SEQ ID NO 8
<211> LENGTH: 76
<212> TYPE: DNA
<213> ORGANISM: Artificial
<220> FEATURE:
<223> OTHER INFORMATION: miR-451 backbone shTyr-2A

<400> SEQUENCE: 8
gcacttggga atggcaaggt tagtatacaa atttgttcga acaaatttgt atactactct 60
tgctataccc agaaaa 76

<210> SEQ ID NO 9
<211> LENGTH: 26
<212> TYPE: DNA
<213> ORGANISM: Artificial
<220> FEATURE:
<223> OTHER INFORMATION: 5RES - Sphl

<400> SEQUENCE: 9
tttgcatgct gctgacagta tgcgac 26

<210> SEQ ID NO 10
<211> LENGTH: 26
<212> TYPE: DNA
<213> ORGANISM: Artificial
<220> FEATURE:
<223> OTHER INFORMATION: 5RES - Sall

<400> SEQUENCE: 10
tttgtcgact gctgacagta tgcgac 26

<210> SEQ ID NO 11
<211> LENGTH: 26
<212> TYPE: DNA
<213> ORGANISM: Artificial

<220> FEATURE:
<223> OTHER INFORMATION: 5RES - NsiI

<400> SEQUENCE: 11
tttatgcatt gctgacagta tgcgac 26

<210> SEQ ID NO 12
<211> LENGTH: 26
<212> TYPE: DNA
<213> ORGANISM: Artificial
<220> FEATURE:
<223> OTHER INFORMATION: 3RES - SalI

<400> SEQUENCE: 12
aaagtcgacc gaaggcagtt ggcagc 26

<210> SEQ ID NO 13
<211> LENGTH: 26
<212> TYPE: DNA
<213> ORGANISM: Artificial
<220> FEATURE:
<223> OTHER INFORMATION: 3RES - NsiI

<400> SEQUENCE: 13
aaaatgcatc gaaggcagtt ggcagc 26

<210> SEQ ID NO 14
<211> LENGTH: 26
<212> TYPE: DNA
<213> ORGANISM: Artificial
<220> FEATURE:
<223> OTHER INFORMATION: 3RES - MluI

<400> SEQUENCE: 14
aaaacgcgtc gaaggcagtt ggcagc 26

<210> SEQ ID NO 15
<211> LENGTH: 22
<212> TYPE: DNA
<213> ORGANISM: Artificial
<220> FEATURE:
<223> OTHER INFORMATION: Guide strand

<400> SEQUENCE: 15
ttagtataca aatttgttca cg 22

<210> SEQ ID NO 16
<211> LENGTH: 20
<212> TYPE: DNA
<213> ORGANISM: Artificial
<220> FEATURE:
<223> OTHER INFORMATION: Passenger strand reversed

<400> SEQUENCE: 16
aatgatatgt aaacaagtgc 20

<210> SEQ ID NO 17
<211> LENGTH: 20
<212> TYPE: DNA
<213> ORGANISM: Artificial
<220> FEATURE:
<223> OTHER INFORMATION: Passenger strand

<400> SEQUENCE: 17
cgtgaacaaa tgtatagtaa 20

-continued

<210> SEQ ID NO 18
<211> LENGTH: 15
<212> TYPE: DNA
<213> ORGANISM: Artificial
<220> FEATURE:
<223> OTHER INFORMATION: 5' Constant Stem

<400> SEQUENCE: 18
ctgacagtat gcgac 15

<210> SEQ ID NO 19
<211> LENGTH: 19
<212> TYPE: DNA
<213> ORGANISM: Artificial
<220> FEATURE:
<223> OTHER INFORMATION: Constant Stem Loop

<400> SEQUENCE: 19
ccgtgaagca gttgaaggg 19

<210> SEQ ID NO 20
<211> LENGTH: 17
<212> TYPE: DNA
<213> ORGANISM: Artificial
<220> FEATURE:
<223> OTHER INFORMATION: 3' Constant Stem

<400> SEQUENCE: 20
gctgccaact gccttcg 17

<210> SEQ ID NO 21
<211> LENGTH: 93
<212> TYPE: DNA
<213> ORGANISM: Artificial
<220> FEATURE:
<223> OTHER INFORMATION: shRNA template oligonucleotide

<400> SEQUENCE: 21
ctgacagtat gcgacttagt atacaaattt gttcacgccg tgaagcagtt gaagggcgtg 60
aacaaatgta tagtaagctg ccaactgcct tcg 93

<210> SEQ ID NO 22
<211> LENGTH: 113
<212> TYPE: DNA
<213> ORGANISM: Artificial
<220> FEATURE:
<223> OTHER INFORMATION: Sphl-Sall shRNA final

<400> SEQUENCE: 22
tttgcatgct gctgacagta tgcgacttag tatacaaatt tgttcacgcc gtgaagcagt 60
tgaagggcgt gaacaaatgt atagtaagct gccaactgcc ttcggtcgac ttt 113

<210> SEQ ID NO 23
<211> LENGTH: 113
<212> TYPE: DNA
<213> ORGANISM: Artificial
<220> FEATURE:
<223> OTHER INFORMATION: Sphl-Nsil shRNA final

<400> SEQUENCE: 23
tttgcatgct gctgacagta tgcgacttag tatacaaatt tgttcacgcc gtgaagcagt 60
tgaagggcgt gaacaaatgt atagtaagct gccaactgcc ttcgatgcat ttt 113

<210> SEQ ID NO 24
<211> LENGTH: 113
<212> TYPE: DNA
<213> ORGANISM: Artificial
<220> FEATURE:
<223> OTHER INFORMATION: Sphl-Mlul shRNA final

<400> SEQUENCE: 24
tttgcatgct gctgacagta tgcgacttag tatacaaatt tgttcacgcc gtgaagcagt 60
tgaagggcgt gaacaaatgt atagtaagct gccaactgcc ttcgacgcgt ttt 113

<210> SEQ ID NO 25
<211> LENGTH: 113
<212> TYPE: DNA
<213> ORGANISM: Artificial
<220> FEATURE:
<223> OTHER INFORMATION: Sall-Nsil shRNA final

<400> SEQUENCE: 25
tttgtcgact gctgacagta tgcgacttag tatacaaatt tgttcacgcc gtgaagcagt 60
tgaagggcgt gaacaaatgt atagtaagct gccaactgcc ttcgatgcat ttt 113

<210> SEQ ID NO 26
<211> LENGTH: 113
<212> TYPE: DNA
<213> ORGANISM: Artificial
<220> FEATURE:
<223> OTHER INFORMATION: Sall-Mlul shRNA final

<400> SEQUENCE: 26
tttgtcgact gctgacagta tgcgacttag tatacaaatt tgttcacgcc gtgaagcagt 60
tgaagggcgt gaacaaatgt atagtaagct gccaactgcc ttcgacgcgt ttt 113

<210> SEQ ID NO 27
<211> LENGTH: 113
<212> TYPE: DNA
<213> ORGANISM: Artificial
<220> FEATURE:
<223> OTHER INFORMATION: Nsil-Mlul shRNA final

<400> SEQUENCE: 27
tttatgcatt gctgacagta tgcgacttag tatacaaatt tgttcacgcc gtgaagcagt 60
tgaagggcgt gaacaaatgt atagtaagct gccaactgcc ttcgacgcgt ttt 113

<210> SEQ ID NO 28
<211> LENGTH: 18
<212> TYPE: DNA
<213> ORGANISM: Artificial
<220> FEATURE:
<223> OTHER INFORMATION: Forward primer pGSH0_FW3

<400> SEQUENCE: 28
ttgagggaga caccctcg 18

<210> SEQ ID NO 29
<211> LENGTH: 21
<212> TYPE: DNA
<213> ORGANISM: Artificial
<220> FEATURE:
<223> OTHER INFORMATION: Reverse primer pGSH0_RV2

<400> SEQUENCE: 29
tttgtatagt tcatccatgc c 21

-continued

<210> SEQ ID NO 30
<211> LENGTH: 2354
<212> TYPE: DNA
<213> ORGANISM: Artificial
<220> FEATURE:
<223> OTHER INFORMATION: Plasmid Xt_Tyr_NM001103048_3xFlag

<400> SEQUENCE: 30

```
gatcaggctc gggggagag tgaggagcag catggaaagg aacatggtcc ctctggcatt     60
ctgctgcctg ttcttcttcc tccatgtttg caggggccag ttcccaaggg catgtagcac    120
cgcagagtcg ctcctgagca aggagtgttg ccctgtgtgg tctggagatg ggtcctcttg    180
tggccagcta tcaggaaggg gtgtctgcca ggatgttgtc ctgaccagct ctgctactgg    240
ccctcagttt ccattcactg ggttgacga tagagagaac tggccaacag tattttacaa     300
caggacgtgc caatgccttg gcaacttcat gggctataac tgtgcagact gcaaatttgg    360
cttcagaggg ccaaactgca cagagagaag aacaatgata agaaaggaga tattccgaat    420
gagcagtgct gagaagagca aattcgttgc ctacttgaat ttggctaagc acaccaccag    480
ccgtgactat gtcatagtca ctggcaccta cgcccagatg aataatggct ccaaccctat    540
gtttgcggat atcaacgtgt atgacctctt tgtctggatg cattactatg cctcccgtga    600
tgtcttcata ggagaagatg ctctctggag agacattgac tttgcccatg aagctccggc    660
ttttgtgccc tggcacaggt acttcctgct gcactgggaa catgagattc agaaactcac    720
aggagatgag aattttacca tccctttctg ggattggaga gatgcccaag gttgtgacat    780
atgtacggat gagcttctgg gaggggtcca tcccaccacc accagcctat taagcccggc    840
atccttcttc gcttcatggc agatagtatg cagccgccct gaggaataca atgctcagag    900
gatcctatgc aatggtaccg gggaagggcc cctgttcaga aatcctggtg gccacgatcg    960
gagcagaacc ccccgattgc ctacaacagc tgaagttgag ctgtgtctgt cattaacaaa   1020
ttacgaaacg gagcccatgg atcggtcggc caactttagc ttcaggaaca ccctagaagg   1080
atttgcagat ccacgaactg ggatagccaa ccgctctcaa agcaacatgc ataactcgct   1140
gcatgtgttc ctcaacggct ccatgtcttc cgtccaagga tcggccaatg acccagtttt   1200
tgtcttgcac catgcttttg tcgacagcat ctttgagcaa tggctcagaa gacacggagc   1260
ttcagtagac atttacccag aagccaatgc accaattggc cacaatcgtg gctactacat   1320
ggttccattt attcctctat acacaaatgg agaattcttt gccgcttcta gagatcttgg   1380
atatgattac gattatctag cagaatcagg ttccattgaa gacttccttt tgccctacct   1440
ggagcaagcg cgacaaatct ggcagtggct ggtaggcgcg gctgtagttg gggactcat    1500
tactgctgtg attgccacta ttgtcggctt ggcgtgccga cggaaaagaa aattcccatc   1560
ggaggaaacg cagccgctgc tcatggaagc cgaagattat caacccacct atcagtctca   1620
cctagactac aaagacgatg acgacaagga ttataaggat gacgatgata aagactataa   1680
agatgatgat gacaaataga acccaaacac tagctaactg taactagcta ctcgtgaaca   1740
aatttgtata ctaattttta tattcggtgg gagccaactg tgtgctcctt gtctaatgtg   1800
ggaagtaact agttttaacc cattttattg cctaagactt gggttccagg gacccacaga   1860
acagcatcga ctacaggccc actctccgtc cttctctcac tttattctct taatgacttc   1920
tccttacatt caaccttctt ccttccattt ctcctctttg ttctcttata gagatggaga   1980
atgaccatgg tctcggcata acaggcaaat ggttgggtga gcagggggtc ccacctatac   2040
ctcggcccac tgggactttc ccaatatccc ggggacccag tccgacactg gccttgagag   2100
```

```
gaaagtcata ttgcccagtc aagtggatag agggttaatc aagttgtgta acacacaatg   2160

tactttttat aaatatatat ataaaaaata tatataatat gtatacttcc caattgatat   2220

gcccagccat ccctatatgt acaaagctga aagattaagg tttaaattcc atgtgataag   2280

ggctacaagt aaataatatt tgggagaaaa aaaaaaaaaa aaaaaaaaaa aaaaaaaaaa   2340

aaaaaaaaaa aaaa                                                     2354
```

<210> SEQ ID NO 31
<211> LENGTH: 5227
<212> TYPE: DNA
<213> ORGANISM: Artificial
<220> FEATURE:
<223> OTHER INFORMATION: Plasmid pGSH0

<400> SEQUENCE: 31

```
ctaaattgta agcgttaata ttttgttaaa attcgcgtta aatttttgtt aaatcagctc     60

atttttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgtagggat aacagggtaa tgcgcgcgta atacgactca    660

ctatagggcg aattgggtac cggccccccc ctcgaccata gccaattcaa tatggcgtat    720

atggactcat gccaattcaa tatggtggat ctggacctgt gccaattcaa tatggcgtat    780

atggactcgt gccaattcaa tatggtggat ctggacccca gccaattcaa tatggcggac    840

ttggcaccat gccaattcaa tatggcggac ttggcactgt gccaactggg gaggggtcta    900

cttggcacgg tgccaagttt gaggaggggt cttggccctg tgccaagtcc gccatattga    960

attggcatgg tgccaataat ggcggccata ttggctatat gccaggatca atatataggc   1020

aatatccaat atggccctat gccaatatgg ctattggcca ggttcaatac tatgtattgg   1080

ccctatgcca tatagtattc catatatggg ttttcctatt gacgtagata gcccctccca   1140

atgggcggtc ccatatacca tatatggggc ttcctaatac cgcccatagc cactccccca   1200

ttgacgtcaa tggtctctat atatggtctt tcctattgac gtcatatggg cggtcctatt   1260

gacgtatatg gcgcctcccc cattgacgtc aattacggta aatggcccgc ctggctcaat   1320

gcccattgac gtcaatagga ccacccacca ttgacgtcaa tgggatggct cattgcccat   1380

tcatatccgt tctcacgccc cctattgacg tcaatgacgg taaatggccc acttggcagt   1440

acatcaatat ctattaatag taacttggca agtacattac tattggaagt acgccagggt   1500

acattggcag tactcccatt gacgtcaatg gcggtaaatg gcccgcgatg gctgccaagt   1560

acatccccat tgacgtcaat ggggaggggc aatgacgcaa atgggcgttc cattgacgta   1620

aatgggcggt aggcgtgcct aatgggaggt ctatataagc aatgctcgtt tagggaaccg   1680

ccattctgcc tggggacgtc ggagcaagct agcttgcttg ttcttttttgc agaagctcag   1740
```

-continued

```
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgccttcgtc gaccttcatg catcttcacg cgtagcttcc cttaatacaa gtgagatgat   2280
ggcataccat ctttcgggac tgagttgatg tgaagagttt ttctgttttg ctgatcactt   2340
gtatattatg tgactaatag ttaaagtgcc aaaataaaat gtgggaacat tgaatgtgta   2400
tcctacttaa gggaatcgat ttcaaggagg acggaaacat cctcggccac aagttggaat   2460
acaactacaa ctcccacaac gtatacatca tggccgacaa gcaaaagaac ggcatcaaag   2520
ccaacttcaa gacccgccac aacatcgaag acggcggcgt gcaactcgct gatcattatc   2580
aacaaaatac tccaattggc gatgaccctg tccttttacc agacaaccat tacctgtcca   2640
cacaatctgc cctttcgaaa gatcccaacg aaaagagaga ccacatggtc cttcttgagt   2700
ttgtaacggc tgctgggatt acacatggca tggatgaact atacaaaaat ctagaactat   2760
agtgagtcgt attacgtaga tccagacatg ataagataca ttgatgagtt tggacaaacc   2820
acaactagaa tgcagtgaaa aaaatgcttt atttgtgaaa tttgtgatgc tattgcttta   2880
tttgtaacca ttataagctg caataaacaa gttaacaaca acaattgcat tcattttatg   2940
tttcaggttc agggggaggt gtgggaggtt ttttaattcg cggccgccac cgcggtggag   3000
ctccagcttt tgttcccttt agtgagggtt aattgcgcgc attaccctgt tatccctacg   3060
cgcttggcgt aatcatggtc atagctgttt cctgtgtgaa attgttatcc gctcacaatt   3120
ccacacaaca tacgagccgg aagcataaag tgtaaagcct ggggtgccta atgagtgagc   3180
taactcacat taattgcgtt gcgctcactg cccgctttcc agtcgggaaa cctgtcgtgc   3240
cagctgcatt aatgaatcgg ccaacgcgcg gggagaggcg gtttgcgtat tgggcgctct   3300
tccgcttcct cgctcactga ctcgctgcgc tcggtcgttc ggctgcggcg agcggtatca   3360
gctcactcaa aggcggtaat acggttatcc acagaatcag gggataacgc aggaaagaac   3420
atgtgagcaa aaggccagca aaaggccagg aaccgtaaaa aggccgcgtt gctggcgttt   3480
ttccataggc tccgcccccc tgacgagcat cacaaaaatc gacgctcaag tcagaggtgg   3540
cgaaacccga caggactata aagataccag gcgtttcccc ctggaagctc cctcgtgcgc   3600
tctcctgttc cgaccctgcc gcttaccgga tacctgtccg cctttctccc ttcgggaagc   3660
gtggcgcttt ctcatagctc acgctgtagg tatctcagtt cggtgtaggt cgttcgctcc   3720
aagctgggct gtgtgcacga accccccgtt cagcccgacc gctgcgcctt atccggtaac   3780
tatcgtcttg agtccaaccc ggtaagacac gacttatcgc cactggcagc agccactggt   3840
aacaggatta gcagagcgag gtatgtaggc ggtgctacag agttcttgaa gtggtggcct   3900
aactacggct acactagaag aacagtattt ggtatctgcg ctctgctgaa gccagttacc   3960
ttcggaaaaa gagttggtag ctcttgatcc ggcaaacaaa ccaccgctgg tagcggtggt   4020
tttttgtttg caagcagcag attacgcgca gaaaaaaagg atctcaagaa gatcctttga   4080
atcttttcta cggggtctga cgctcagtgg aacgaaaact cacgttaagg gattttggtc   4140
```

-continued atgagattat caaaaaggat cttcacctag atccttttaa attaaaaatg aagttttaaa 4200
tcaatctaaa gtatatatga gtaaacttgg tctgacagtt accaatgctt aatcagtgag 4260
gcacctatct cagcgatctg tctatttcgt tcatccatag ttgcctgact ccccgtcgtg 4320
tagataacta cgatacggga gggcttacca tctggcccca gtgctgcaat gataccgcga 4380
gacccacgct caccggctcc agatttatca gcaataaacc agccagccgg aagggccgag 4440
cgcagaagtg gtcctgcaac tttatccgcc tccatccagt ctattaattg ttgccgggaa 4500
gctagagtaa gtagttcgcc agttaatagt ttgcgcaacg ttgttgccat tgctacaggc 4560
atcgtggtgt cacgctcgtc gtttggtatg gcttcattca gctccggttc ccaacgatca 4620
aggcgagtta catgatcccc catgttgtgc aaaaaagcgg ttagctcctt cggtcctccg 4680
atcgttgtca gaagtaagtt ggccgcagtg ttatcactca tggttatggc agcactgcat 4740
aattctctta ctgtcatgcc atccgtaaga tgcttttctg tgactggtga gtactcaacc 4800
aagtcattct gagaatagtg tatgcggcga ccgagttgct cttgcccggc gtcaatacgg 4860
gataataccg cgccacatag cagaacttta aaagtgctca tcattggaaa acgttcttcg 4920
gggcgaaaac tctcaaggat cttaccgctg ttgagatcca gttcgatgta acccactcgt 4980
gcacccaact gatcttcagc atcttttact ttcaccagcg tttctgggtg agcaaaaaca 5040
ggaaggcaaa atgccgcaaa aaagggaata agggcgacac ggaaatgttg aatactcata 5100
ctcttccttt ttcaatatta ttgaagcatt tatcagggtt attgtctcat gagcggatac 5160
atatttgaat gtatttagaa aaataaacaa ataggggttc cgcgcacatt tccccgaaaa 5220
gtgccac 5227

<210> SEQ ID NO 32
<211> LENGTH: 5318
<212> TYPE: DNA
<213> ORGANISM: Artificial
<220> FEATURE:
<223> OTHER INFORMATION: Plasmid pGSH0_OshRNA_Tyr1A

<400> SEQUENCE: 32
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgtagggat aacagggtaa tgcgcgcgta atacgactca 660
ctatagggcg aattgggtac cgggcccccc ctcgaccata gccaattcaa tatggcgtat 720
atggactcat gccaattcaa tatggtggat ctggacctgt gccaattcaa tatggcgtat 780
atggactcgt gccaattcaa tatggtggat ctggacccca gccaattcaa tatggcggac 840
ttggcaccat gccaattcaa tatggcggac ttggcactgt gccaactggg gaggggtcta 900

-continued

```
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgccttcgtc gactgctgac agtatgcgac ttagtataca aatttgttca cgccgtgaag   2280
cagttgaagg gcgtgaacaa atgtatagta agctgccaac tgccttcgat gcatcttcac   2340
gcgtagcttc ccttaataca agtgagatga tggcatacca tctttcggga ctgagttgat   2400
gtgaagagtt tttctgtttt gctgatcact tgtatattat gtgactaata gttaaagtgc   2460
caaaataaaa tgtgggaaca ttgaatgtgt atcctactta agggaatcga tttcaaggag   2520
gacggaaaca tcctcggcca caagttggaa tacaactaca actcccacaa cgtatacatc   2580
atggccgaca agcaaaagaa cggcatcaaa gccaacttca agacccgcca caacatcgaa   2640
gacggcggcg tgcaactcgc tgatcattat caacaaaata ctccaattgg cgatgaccct   2700
gtccttttac cagacaacca ttacctgtcc acacaatctg ccctttcgaa agatcccaac   2760
gaaaagagag accacatggt ccttcttgag tttgtaacgg ctgctgggat tacacatggc   2820
atggatgaac tatacaaaaa tctagaacta tagtgagtcg tattacgtag atccagacat   2880
gataagatac attgatgagt ttggacaaac cacaactaga atgcagtgaa aaaaatgctt   2940
tatttgtgaa atttgtgatg ctattgcttt atttgtaacc attataagct gcaataaaca   3000
agttaacaac aacaattgca ttcattttat gtttcaggtt cagggggagg tgtgggaggt   3060
tttttaattc gcggccgcca ccgcggtgga gctccagctt ttgttccctt tagtgagggt   3120
taattgcgcg cattaccctg ttatccctac gcgcttggcg taatcatggt catagctgtt   3180
tcctgtgtga aattgttatc cgctcacaat tccacacaac atacgagccg gaagcataaa   3240
gtgtaaagcc tggggtgcct aatgagtgag ctaactcaca ttaattgcgt tgcgctcact   3300
```

-continued

```
gcccgctttc cagtcgggaa acctgtcgtg ccagctgcat taatgaatcg gccaacgcgc   3360
ggggagaggc ggtttgcgta ttgggcgctc ttccgcttcc tcgctcactg actcgctgcg   3420
ctcggtcgtt cggctgcggc gagcggtatc agctcactca aaggcggtaa tacggttatc   3480
cacagaatca ggggataacg caggaaagaa catgtgagca aaaggccagc aaaaggccag   3540
gaaccgtaaa aaggccgcgt tgctggcgtt tttccatagg ctccgccccc ctgacgagca   3600
tcacaaaaat cgacgctcaa gtcagaggtg gcgaaacccg acaggactat aaagatacca   3660
ggcgtttccc cctggaagct ccctcgtgcg ctctcctgtt ccgaccctgc cgcttaccgg   3720
atacctgtcc gcctttctcc cttcgggaag cgtggcgctt tctcatagct cacgctgtag   3780
gtatctcagt tcggtgtagg tcgttcgctc caagctgggc tgtgtgcacg aaccccccgt   3840
tcagcccgac cgctgcgcct tatccggtaa ctatcgtctt gagtccaacc cggtaagaca   3900
cgacttatcg ccactggcag cagccactgg taacaggatt agcagagcga ggtatgtagg   3960
cggtgctaca gagttcttga agtggtggcc taactacggc tacactagaa gaacagtatt   4020
tggtatctgc gctctgctga agccagttac cttcggaaaa agagttggta gctcttgatc   4080
cggcaaacaa accaccgctg gtagcggtgg tttttttgtt tgcaagcagc agattacgcg   4140
cagaaaaaaa ggatctcaag aagatccttt gatcttttct acggggtctg acgctcagtg   4200
gaacgaaaac tcacgttaag ggattttggt catgagatta tcaaaaagga tcttcaccta   4260
gatcctttta aattaaaaat gaagttttaa atcaatctaa agtatatatg agtaaacttg   4320
gtctgacagt taccaatgct taatcagtga ggcacctatc tcagcgatct gtctatttcg   4380
ttcatccata gttgcctgac tccccgtcgt gtagataact acgatacggg agggcttacc   4440
atctggcccc agtgctgcaa tgataccgcg agacccacgc tcaccggctc cagatttatc   4500
agcaataaac cagccagccg gaagggccga gcgcagaagt ggtcctgcaa ctttatccgc   4560
ctccatccag tctattaatt gttgccggga agctagagta agtagttcgc cagttaatag   4620
tttgcgcaac gttgttgcca ttgctacagg catcgtggtg tcacgctcgt cgtttggtat   4680
ggcttcattc agctccggtt cccaacgatc aaggcgagtt acatgatccc ccatgttgtg   4740
caaaaaagcg gttagctcct tcggtcctcc gatcgttgtc agaagtaagt tggccgcagt   4800
gttatcactc atggttatgg cagcactgca taattctctt actgtcatgc catccgtaag   4860
atgcttttct gtgactggtg agtactcaac caagtcattc tgagaatagt gtatgcggcg   4920
accgagttgc tcttgcccgg cgtcaatacg ggataatacc gcgccacata gcagaacttt   4980
aaaagtgctc atcattggaa aacgttcttc ggggcgaaaa ctctcaagga tcttaccgct   5040
gttgagatcc agttcgatgt aacccactcg tgcacccaac tgatcttcag catcttttac   5100
tttcaccagc gtttctgggt gagcaaaaac aggaaggcaa aatgccgcaa aaaagggaat   5160
aagggcgaca cggaaatgtt gaatactcat actcttcctt tttcaatatt attgaagcat   5220
ttatcagggt tattgtctca tgagcggata catatttgaa tgtatttaga aaaataaaca   5280
aataggggtt ccgcgcacat ttccccgaaa agtgccac                           5318
```

<210> SEQ ID NO 33
<211> LENGTH: 5318
<212> TYPE: DNA
<213> ORGANISM: Artificial
<220> FEATURE:
<223> OTHER INFORMATION: Plasmid pGSH0_OshRNA_Tyr2A

<400> SEQUENCE: 33

-continued

```
ctaaattgta agcgttaata ttttgttaaa attcgcgtta aatttttgtt aaatcagctc     60
atttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgtagggat aacagggtaa tgcgcgcgta atacgactca    660
ctatagggcg aattgggtac cgggcccccc ctcgaccata gccaattcaa tatggcgtat    720
atggactcat gccaattcaa tatggtggat ctggacctgt gccaattcaa tatggcgtat    780
atggactcgt gccaattcaa tatggtggat ctggacccca gccaattcaa tatggcggac    840
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttcttttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgccttcgtc gactgctgac agtatgcgac ttagtataca aatttgttca cgccgtgaag   2280
cagttgaagg gcgtgaacaa atgtatagta agctgccaac tgccttcgat gcatcttcac   2340
gcgtagcttc ccttaataca agtgagatga tggcatacca tctttcggga ctgagttgat   2400
```

-continued

```
gtgaagagtt tttctgtttt gctgatcact tgtatattat gtgactaata gttaaagtgc   2460
caaaataaaa tgtgggaaca ttgaatgtgt atcctactta agggaatcga tttcaaggag   2520
gacggaaaca tcctcggcca caagttggaa tacaactaca actcccacaa cgtatacatc   2580
atggccgaca agcaaaagaa cggcatcaaa gccaacttca agacccgcca caacatcgaa   2640
gacggcggcg tgcaactcgc tgatcattat caacaaaata ctccaattgg cgatgaccct   2700
gtccttttac cagacaacca ttacctgtcc acacaatctg ccctttcgaa agatcccaac   2760
gaaaagagag accacatggt ccttcttgag tttgtaacgg ctgctgggat tacacatggc   2820
atggatgaac tatacaaaaa tctagaacta tagtgagtcg tattacgtag atccagacat   2880
gataagatac attgatgagt ttggacaaac cacaactaga atgcagtgaa aaaaatgctt   2940
tatttgtgaa atttgtgatg ctattgcttt atttgtaacc attataagct gcaataaaca   3000
agttaacaac aacaattgca ttcattttat gtttcaggtt cagggggagg tgtgggaggt   3060
tttttaattc gcggccgcca ccgcggtgga gctccagctt ttgttccctt tagtgagggt   3120
taattgcgcg cattaccctg ttatccctac gcgcttggcg taatcatggt catagctgtt   3180
tcctgtgtga aattgttatc cgctcacaat tccacacaac atacgagccg gaagcataaa   3240
gtgtaaagcc tggggtgcct aatgagtgag ctaactcaca ttaattgcgt tgcgctcact   3300
gcccgctttc cagtcgggaa acctgtcgtg ccagctgcat taatgaatcg gccaacgcgc   3360
ggggagaggc ggtttgcgta ttgggcgctc ttccgcttcc tcgctcactg actcgctgcg   3420
ctcggtcgtt cggctgcggc gagcggtatc agctcactca aaggcggtaa tacggttatc   3480
cacagaatca ggggataacg caggaaagaa catgtgagca aaaggccagc aaaaggccag   3540
gaaccgtaaa aaggccgcgt tgctggcgtt tttccatagg ctccgccccc ctgacgagca   3600
tcacaaaaat cgacgctcaa gtcagaggtg gcgaaacccg acaggactat aaagatacca   3660
ggcgtttccc cctggaagct ccctcgtgcg ctctcctgtt ccgaccctgc cgcttaccgg   3720
atacctgtcc gcctttctcc cttcgggaag cgtggcgctt tctcatagct cacgctgtag   3780
gtatctcagt tcggtgtagg tcgttcgctc caagctgggc tgtgtgcacg aaccccccgt   3840
tcagcccgac cgctgcgcct tatccggtaa ctatcgtctt gagtccaacc cggtaagaca   3900
cgacttatcg ccactggcag cagccactgg taacaggatt agcagagcga ggtatgtagg   3960
cggtgctaca gagttcttga agtggtggcc taactacggc tacactagaa gaacagtatt   4020
tggtatctgc gctctgctga agccagttac cttcggaaaa agagttggta gctcttgatc   4080
cggcaaacaa accaccgctg gtagcggtgg tttttttgtt tgcaagcagc agattacgcg   4140
cagaaaaaaa ggatctcaag aagatccttt gatcttttct acggggtctg acgctcagtg   4200
gaacgaaaac tcacgttaag ggattttggt catgagatta tcaaaaagga tcttcaccta   4260
gatcctttta aattaaaaat gaagttttaa atcaatctaa agtatatatg agtaaacttg   4320
gtctgacagt taccaatgct taatcagtga ggcacctatc tcagcgatct gtctatttcg   4380
ttcatccata gttgcctgac tccccgtcgt gtagataact acgatacggg agggcttacc   4440
atctggcccc agtgctgcaa tgataccgcg agacccacgc tcaccggctc cagatttatc   4500
agcaataaac cagccagccg gaagggccga gcgcagaagt ggtcctgcaa ctttatccgc   4560
ctccatccag tctattaatt gttgccggga agctagagta agtagttcgc cagttaatag   4620
tttgcgcaac gttgttgcca ttgctacagg catcgtggtg tcacgctcgt cgtttggtat   4680
ggcttcattc agctccggtt cccaacgatc aaggcgagtt acatgatccc ccatgttgtg   4740
```

-continued

```
caaaaaagcg gttagctcct tcggtcctcc gatcgttgtc agaagtaagt tggccgcagt   4800

gttatcactc atggttatgg cagcactgca taattctctt actgtcatgc catccgtaag   4860

atgcttttct gtgactggtg agtactcaac caagtcattc tgagaatagt gtatgcggcg   4920

accgagttgc tcttgcccgg cgtcaatacg ggataatacc gcgccacata gcagaacttt   4980

aaaagtgctc atcattggaa aacgttcttc ggggcgaaaa ctctcaagga tcttaccgct   5040

gttgagatcc agttcgatgt aacccactcg tgcacccaac tgatcttcag catcttttac   5100

tttcaccagc gtttctgggt gagcaaaaac aggaaggcaa aatgccgcaa aaaagggaat   5160

aagggcgaca cggaaatgtt gaatactcat actcttcctt tttcaatatt attgaagcat   5220

ttatcagggt tattgtctca tgagcggata catatttgaa tgtatttaga aaaataaaca   5280

aataggggtt ccgcgcacat ttccccgaaa agtgccac                            5318
```

<210> SEQ ID NO 34
<211> LENGTH: 5308
<212> TYPE: DNA
<213> ORGANISM: Artificial
<220> FEATURE:
<223> OTHER INFORMATION: Plasmid pGSH0_OshRNA_Tyr1B

<400> SEQUENCE: 34

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgtagggat aacagggtaa tgcgcgcgta atacgactca    660

ctatagggcg aattgggtac cggggccccc ctcgaccata gccaattcaa tatggcgtat    720

atggactcat gccaattcaa tatggtggat ctggacctgt gccaattcaa tatggcgtat    780

atggactcgt gccaattcaa tatggtggat ctggacccca gccaattcaa tatggcggac    840

ttggcaccat gccaattcaa tatggcggac ttggcactgt gccaactggg gaggggtcta    900

cttggcacgg tgccaagttt gaggaggggt cttggccctg tgccaagtcc gccatattga    960

attggcatgg tgccaataat ggcggccata ttggctatat gccaggatca atatataggc   1020

aatatccaat atggccctat gccaatatgg ctattggcca ggttcaatac tatgtattgg   1080

ccctatgcca tatagtattc catatatggg ttttcctatt gacgtagata gcccctccca   1140

atgggcggtc ccatatacca tatatggggc ttcctaatac cgcccatagc cactccccca   1200

ttgacgtcaa tggtctctat atatggtctt tcctattgac gtcatatggg cggtcctatt   1260

gacgtatatg gcgcctcccc cattgacgtc aattacggta aatggcccgc ctggctcaat   1320

gcccattgac gtcaatagga ccacccacca ttgacgtcaa tgggatggct cattgcccat   1380

tcatatccgt tctcacgccc cctattgacg tcaatgacgg taaatggccc acttggcagt   1440

acatcaatat ctattaatag taacttggca agtacattac tattggaagt acgccagggt   1500
```

```
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac ttattcatct gggcgtaggt gcctgtgaag cagttgaagg   2280
gggacctacg aagatgaaca agctgccaac tgccttcgat gcatcttcac gcgtagcttc   2340
ccttaataca agtgagatga tggcatacca tctttcggga ctgagttgat gtgaagagtt   2400
tttctgtttt gctgatcact tgtatattat gtgactaata gttaaagtgc caaaataaaa   2460
tgtgggaaca ttgaatgtgt atcctactta agggaatcga tttcaaggag gacggaaaca   2520
tcctcggcca caagttggaa tacaactaca actcccacaa cgtatacatc atggccgaca   2580
agcaaaagaa cggcatcaaa gccaacttca agacccgcca caacatcgaa gacggcggcg   2640
tgcaactcgc tgatcattat caacaaaata ctccaattgg cgatgaccct gtccttttac   2700
cagacaacca ttacctgtcc acacaatctg ccctttcgaa agatcccaac gaaaagagag   2760
accacatggt ccttcttgag tttgtaacgg ctgctgggat tacacatggc atggatgaac   2820
tatacaaaaa tctagaacta tagtgagtcg tattacgtag atccagacat gataagatac   2880
attgatgagt ttggacaaac cacaactaga atgcagtgaa aaaaatgctt tatttgtgaa   2940
atttgtgatg ctattgcttt atttgtaacc attataagct gcaataaaca agttaacaac   3000
aacaattgca ttcattttat gtttcaggtt cagggggagg tgtgggaggt tttttaattc   3060
gcggccgcca ccgcggtgga gctccagctt ttgttccctt tagtgagggt taattgcgcg   3120
cattaccctg ttatccctac gcgcttggcg taatcatggt catagctgtt tcctgtgtga   3180
aattgttatc cgctcacaat tccacacaac atacgagccg gaagcataaa gtgtaaagcc   3240
tggggtgcct aatgagtgag ctaactcaca ttaattgcgt tgcgctcact gcccgctttc   3300
cagtcgggaa acctgtcgtg ccagctgcat taatgaatcg gccaacgcgc ggggagaggc   3360
ggtttgcgta ttgggcgctc ttccgcttcc tcgctcactg actcgctgcg ctcggtcgtt   3420
cggctgcggc gagcggtatc agctcactca aaggcggtaa tacggttatc cacagaatca   3480
ggggataacg caggaaagaa catgtgagca aaaggccagc aaaaggccag gaaccgtaaa   3540
aaggccgcgt tgctggcgtt tttccatagg ctccgccccc ctgacgagca tcacaaaaat   3600
cgacgctcaa gtcagaggtg gcgaaacccg acaggactat aaagatacca ggcgtttccc   3660
cctggaagct ccctcgtgcg ctctcctgtt ccgaccctgc cgcttaccgg atacctgtcc   3720
gcctttctcc cttcgggaag cgtggcgctt tctcatagct cacgctgtag gtatctcagt   3780
tcggtgtagg tcgttcgctc caagctgggc tgtgtgcacg aaccccccgt tcagcccgac   3840
```

-continued

```
cgctgcgcct tatccggtaa ctatcgtctt gagtccaacc cggtaagaca cgacttatcg   3900

ccactggcag cagccactgg taacaggatt agcagagcga ggtatgtagg cggtgctaca   3960

gagttcttga agtggtggcc taactacggc tacactagaa gaacagtatt tggtatctgc   4020

gctctgctga agccagttac cttcggaaaa agagttggta gctcttgatc cggcaaacaa   4080

accaccgctg gtagcggtgg tttttttgtt tgcaagcagc agattacgcg cagaaaaaaa   4140

ggatctcaag aagatccttt gatcttttct acggggtctg acgctcagtg gaacgaaaac   4200

tcacgttaag ggattttggt catgagatta tcaaaaagga tcttcaccta gatcctttta   4260

aattaaaaat gaagttttaa atcaatctaa agtatatatg agtaaacttg gtctgacagt   4320

taccaatgct taatcagtga ggcacctatc tcagcgatct gtctatttcg ttcatccata   4380

gttgcctgac tccccgtcgt gtagataact acgatacggg agggcttacc atctggcccc   4440

agtgctgcaa tgataccgcg agacccacgc tcaccggctc cagatttatc agcaataaac   4500

cagccagccg gaagggccga gcgcagaagt ggtcctgcaa ctttatccgc ctccatccag   4560

tctattaatt gttgccggga agctagagta agtagttcgc cagttaatag tttgcgcaac   4620

gttgttgcca ttgctacagg catcgtggtg tcacgctcgt cgtttggtat ggcttcattc   4680

agctccggtt cccaacgatc aaggcgagtt acatgatccc ccatgttgtg caaaaaagcg   4740

gttagctcct tcggtcctcc gatcgttgtc agaagtaagt tggccgcagt gttatcactc   4800

atggttatgg cagcactgca taattctctt actgtcatgc catccgtaag atgcttttct   4860

gtgactggtg agtactcaac caagtcattc tgagaatagt gtatgcggcg accgagttgc   4920

tcttgcccgg cgtcaatacg ggataatacc gcgccacata gcagaacttt aaaagtgctc   4980

atcattggaa aacgttcttc ggggcgaaaa ctctcaagga tcttaccgct gttgagatcc   5040

agttcgatgt aacccactcg tgcacccaac tgatcttcag catcttttac tttcaccagc   5100

gtttctgggt gagcaaaaac aggaaggcaa aatgccgcaa aaaagggaat aagggcgaca   5160

cggaaatgtt gaatactcat actcttcctt tttcaatatt attgaagcat ttatcagggt   5220

tattgtctca tgagcggata catatttgaa tgtatttaga aaaataaaca aataggggtt   5280

ccgcgcacat ttccccgaaa agtgccac                                      5308
```

<210> SEQ ID NO 35
<211> LENGTH: 5308
<212> TYPE: DNA
<213> ORGANISM: Artificial
<220> FEATURE:
<223> OTHER INFORMATION: Plasmid pGSH0_OshRNA_Tyr2B

<400> SEQUENCE: 35

```
ctaaattgta agcgttaata ttttgttaaa attcgcgtta aatttttgtt aaatcagctc     60

atttttttaac caataggccg aaatcggcaa aatcccttat aaatcaaaag aatagaccga   120

gatagggttg agtgttgttc cagtttggaa caagagtcca ctattaaaga acgtggactc   180

caacgtcaaa gggcgaaaaa ccgtctatca gggcgatggc ccactacgtg aaccatcacc   240

ctaatcaagt tttttggggt cgaggtgccg taaagcacta aatcggaacc ctaaagggag   300

cccccgattt agagcttgac ggggaaagcc ggcgaacgtg gcgagaaagg aagggaagaa   360

agcgaaagga gcgggcgcta gggcgctggc aagtgtagcg gtcacgctgc gcgtaaccac   420

cacacccgcc gcgcttaatg cgccgctaca gggcgcgtcc cattcgccat tcaggctgcg   480

caactgttgg gaagggcgat cggtgcgggc ctcttcgcta ttacgccagc tggcgaaagg   540

gggatgtgct gcaaggcgat taagttgggt aacgccaggg ttttcccagt cacgacgttg   600
```

```
taaaacgacg gccagtgagc gcgtagggat aacagggtaa tgcgcgcgta atacgactca    660
ctatagggcg aattgggtac cgggcccccc ctcgaccata gccaattcaa tatggcgtat    720
atggactcat gccaattcaa tatggtggat ctggacctgt gccaattcaa tatggcgtat    780
atggactcgt gccaattcaa tatggtggat ctggacccca gccaattcaa tatggcggac    840
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac ttgtggccaa ttggtgcatt ggctgtgaag cagttgaagg   2280
gccaatgcac cttggccata agctgccaac tgccttcgat gcatcttcac gcgtagcttc   2340
ccttaataca agtgagatga tggcatacca tctttcggga ctgagttgat gtgaagagtt   2400
tttctgtttt gctgatcact tgtatattat gtgactaata gttaaagtgc caaaataaaa   2460
tgtgggaaca ttgaatgtgt atcctactta agggaatcga tttcaaggag gacggaaaca   2520
tcctcggcca caagttggaa tacaactaca actcccacaa cgtatacatc atggccgaca   2580
agcaaaagaa cggcatcaaa gccaacttca agacccgcca caacatcgaa gacggcggcg   2640
tgcaactcgc tgatcattat caacaaaata ctccaattgg cgatgaccct gtccttttac   2700
cagacaacca ttacctgtcc acacaatctg ccctttcgaa agatcccaac gaaaagagag   2760
accacatggt ccttcttgag tttgtaacgg ctgctgggat tacacatggc atggatgaac   2820
tatacaaaaa tctagaacta tagtgagtcg tattacgtag atccagacat gataagatac   2880
attgatgagt ttggacaaac cacaactaga atgcagtgaa aaaaatgctt tatttgtgaa   2940
```

-continued

```
atttgtgatg ctattgcttt atttgtaacc attataagct gcaataaaca agttaacaac   3000
aacaattgca ttcattttat gtttcaggtt cagggggagg tgtgggaggt tttttaattc   3060
gcggccgcca ccgcggtgga gctccagctt ttgttccctt tagtgagggt taattgcgcg   3120
cattaccctg ttatccctac gcgcttggcg taatcatggt catagctgtt tcctgtgtga   3180
aattgttatc cgctcacaat tccacacaac atacgagccg gaagcataaa gtgtaaagcc   3240
tggggtgcct aatgagtgag ctaactcaca ttaattgcgt tgcgctcact gcccgctttc   3300
cagtcgggaa acctgtcgtg ccagctgcat taatgaatcg gccaacgcgc ggggagaggc   3360
ggtttgcgta ttgggcgctc ttccgcttcc tcgctcactg actcgctgcg ctcggtcgtt   3420
cggctgcggc gagcggtatc agctcactca aaggcggtaa tacggttatc cacagaatca   3480
ggggataacg caggaaagaa catgtgagca aaaggccagc aaaaggccag gaaccgtaaa   3540
aaggccgcgt tgctggcgtt tttccatagg ctccgccccc ctgacgagca tcacaaaaat   3600
cgacgctcaa gtcagaggtg gcgaaacccg acaggactat aaagatacca ggcgtttccc   3660
cctggaagct ccctcgtgcg ctctcctgtt ccgaccctgc cgcttaccgg atacctgtcc   3720
gcctttctcc cttcgggaag cgtggcgctt tctcatagct cacgctgtag gtatctcagt   3780
tcggtgtagg tcgttcgctc caagctgggc tgtgtgcacg aaccccccgt tcagcccgac   3840
cgctgcgcct tatccggtaa ctatcgtctt gagtccaacc cggtaagaca cgacttatcg   3900
ccactggcag cagccactgg taacaggatt agcagagcga ggtatgtagg cggtgctaca   3960
gagttcttga agtggtggcc taactacggc tacactagaa gaacagtatt tggtatctgc   4020
gctctgctga agccagttac cttcggaaaa agagttggta gctcttgatc cggcaaacaa   4080
accaccgctg gtagcggtgg tttttttgtt tgcaagcagc agattacgcg cagaaaaaaa   4140
ggatctcaag aagatccttt gatcttttct acggggtctg acgctcagtg gaacgaaaac   4200
tcacgttaag ggattttggt catgagatta tcaaaaagga tcttcaccta gatcctttta   4260
aattaaaaat gaagttttaa atcaatctaa agtatatatg agtaaacttg gtctgacagt   4320
taccaatgct taatcagtga ggcacctatc tcagcgatct gtctatttcg ttcatccata   4380
gttgcctgac tccccgtcgt gtagataact acgatacggg agggcttacc atctggcccc   4440
agtgctgcaa tgataccgcg agacccacgc tcaccggctc cagatttatc agcaataaac   4500
cagccagccg gaagggccga gcgcagaagt ggtcctgcaa ctttatccgc ctccatccag   4560
tctattaatt gttgccggga agctagagta agtagttcgc cagttaatag tttgcgcaac   4620
gttgttgcca ttgctacagg catcgtggtg tcacgctcgt cgtttggtat ggcttcattc   4680
agctccggtt cccaacgatc aaggcgagtt acatgatccc ccatgttgtg caaaaaagcg   4740
gttagctcct tcggtcctcc gatcgttgtc agaagtaagt tggccgcagt gttatcactc   4800
atggttatgg cagcactgca taattctctt actgtcatgc catccgtaag atgcttttct   4860
gtgactggtg agtactcaac caagtcattc tgagaatagt gtatgcggcg accgagttgc   4920
tcttgcccgg cgtcaatacg ggataatacc gcgccacata gcagaacttt aaaagtgctc   4980
atcattggaa aacgttcttc ggggcgaaaa ctctcaagga tcttaccgct gttgagatcc   5040
agttcgatgt aacccactcg tgcacccaac tgatcttcag catcttttac tttcaccagc   5100
gtttctgggt gagcaaaaac aggaaggcaa aatgccgcaa aaaagggaat aagggcgaca   5160
cggaaatgtt gaatactcat actcttcctt tttcaatatt attgaagcat ttatcagggt   5220
tattgtctca tgagcggata catatttgaa tgtatttaga aaaataaaca aataggggtt   5280
ccgcgcacat ttccccgaaa agtgccac                                      5308
```

<210> SEQ ID NO 36
<211> LENGTH: 5308
<212> TYPE: DNA
<213> ORGANISM: Artificial
<220> FEATURE:
<223> OTHER INFORMATION: Plasmid pGSH0_OshRNA_Tyr3B

<400> SEQUENCE: 36
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgtagggat aacagggtaa tgcgcgcgta atacgactca 660
ctatagggcg aattgggtac cggcccccc ctcgaccata gccaattcaa tatggcgtat 720
atggactcat gccaattcaa tatggtggat ctggacctgt gccaattcaa tatggcgtat 780
atggactcgt gccaattcaa tatggtggat ctggacccca gccaattcaa tatggcggac 840
ttggcaccat gccaattcaa tatggcggac ttggcactgt gccaactggg gaggggtcta 900
cttggcacgg tgccaagttt gaggaggggt cttggccctg tgccaagtcc gccatattga 960
attggcatgg tgccaataat ggcggccata ttggctatat gccaggatca atatataggc 1020
aatatccaat atggccctat gccaatatgg ctattggcca ggttcaatac tatgtattgg 1080
ccctatgcca tatagtattc catatatggg ttttcctatt gacgtagata gcccctccca 1140
atgggcggtc ccatatacca tatatggggc ttcctaatac cgcccatagc cactccccca 1200
ttgacgtcaa tggtctctat atatggtctt tcctattgac gtcatatggg cggtcctatt 1260
gacgtatatg gcgcctcccc cattgacgtc aattacggta aatggcccgc ctggctcaat 1320
gcccattgac gtcaatagga ccacccacca ttgacgtcaa tgggatggct cattgcccat 1380
tcatatccgt tctcacgccc cctattgacg tcaatgacgg taaatggccc acttggcagt 1440
acatcaatat ctattaatag taacttggca agtacattac tattggaagt acgccagggt 1500
acattggcag tactcccatt gacgtcaatg gcggtaaatg gcccgcgatg gctgccaagt 1560
acatccccat tgacgtcaat ggggaggggc aatgacgcaa atgggcgttc cattgacgta 1620
aatgggcggt aggcgtgcct aatgggaggt ctatataagc aatgctcgtt tagggaaccg 1680
ccattctgcc tggggacgtc ggagcaagct agcttgcttg ttcttttttgc agaagctcag 1740 aataaacgct caactttggc agatctgaat tcctgcagcc cgggggatcc acagccacca 1800
tgagtaaagg agaagaactt ttcactggag ttgtcccaat tcttgttgaa ttagatggtg 1860
atgttaatgg gtacaaattt tctgtcagtg gagagggtga aggtgatgca acatacggaa 1920
aacttaccct taaatttatt tgcactactg gaaaactacc tgttccatgg ccaacacttg 1980
tcactactct cacttatggt gttcaatgct tttcaagata tccagatcat atgaagcggc 2040

-continued

```
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac ttcccacatt agacaaggag cactgtgaag cagttgaagg   2280
gtgctccttg aaatgtggaa agctgccaac tgccttcgat gcatcttcac gcgtagcttc   2340
ccttaataca agtgagatga tggcatacca tctttcggga ctgagttgat gtgaagagtt   2400
tttctgtttt gctgatcact tgtatattat gtgactaata gttaaagtgc caaaataaaa   2460
tgtgggaaca ttgaatgtgt atcctactta agggaatcga tttcaaggag gacggaaaca   2520
tcctcggcca caagttggaa tacaactaca actcccacaa cgtatacatc atggccgaca   2580
agcaaaagaa cggcatcaaa gccaacttca agacccgcca caacatcgaa gacggcggcg   2640
tgcaactcgc tgatcattat caacaaaata ctccaattgg cgatgaccct gtccttttac   2700
cagacaacca ttacctgtcc acacaatctg ccctttcgaa agatcccaac gaaaagagag   2760
accacatggt ccttcttgag tttgtaacgg ctgctgggat tacacatggc atggatgaac   2820
tatacaaaaa tctagaacta tagtgagtcg tattacgtag atccagacat gataagatac   2880
attgatgagt ttggacaaac cacaactaga atgcagtgaa aaaaatgctt tatttgtgaa   2940
atttgtgatg ctattgcttt atttgtaacc attataagct gcaataaaca agttaacaac   3000
aacaattgca ttcattttat gtttcaggtt cagggggagg tgtgggaggt tttttaattc   3060
gcggccgcca ccgcggtgga gctccagctt ttgttccctt tagtgagggt taattgcgcg   3120
cattaccctg ttatccctac gcgcttggcg taatcatggt catagctgtt tcctgtgtga   3180
aattgttatc cgctcacaat tccacacaac atacgagccg gaagcataaa gtgtaaagcc   3240
tggggtgcct aatgagtgag ctaactcaca ttaattgcgt tgcgctcact gcccgctttc   3300
cagtcgggaa acctgtcgtg ccagctgcat taatgaatcg gccaacgcgc ggggagaggc   3360
ggtttgcgta ttgggcgctc ttccgcttcc tcgctcactg actcgctgcg ctcggtcgtt   3420
cggctgcggc gagcggtatc agctcactca aaggcggtaa tacggttatc cacagaatca   3480
ggggataacg caggaaagaa catgtgagca aaaggccagc aaaaggccag gaaccgtaaa   3540
aaggccgcgt tgctggcgtt tttccatagg ctccgccccc ctgacgagca tcacaaaaat   3600
cgacgctcaa gtcagaggtg gcgaaacccg acaggactat aaagatacca ggcgtttccc   3660
cctggaagct ccctcgtgcg ctctcctgtt ccgaccctgc cgcttaccgg atacctgtcc   3720
gcctttctcc cttcgggaag cgtggcgctt tctcatagct cacgctgtag gtatctcagt   3780
tcggtgtagg tcgttcgctc caagctgggc tgtgtgcacg aaccccccgt tcagcccgac   3840
cgctgcgcct tatccggtaa ctatcgtctt gagtccaacc cggtaagaca cgacttatcg   3900
ccactggcag cagccactgg taacaggatt agcagagcga ggtatgtagg cggtgctaca   3960
gagttcttga agtggtggcc taactacggc tacactagaa gaacagtatt tggtatctgc   4020
gctctgctga agccagttac cttcggaaaa agagttggta gctcttgatc cggcaaacaa   4080
accaccgctg gtagcggtgg tttttttgtt tgcaagcagc agattacgcg cagaaaaaaa   4140
ggatctcaag aagatccttt gatcttttct acggggtctg acgctcagtg gaacgaaaac   4200
tcacgttaag ggattttggt catgagatta tcaaaaagga tcttcaccta gatcctttta   4260
aattaaaaat gaagttttaa atcaatctaa agtatatatg agtaaacttg gtctgacagt   4320
taccaatgct taatcagtga ggcacctatc tcagcgatct gtctatttcg ttcatccata   4380
gttgcctgac tccccgtcgt gtagataact acgatacggg agggcttacc atctggcccc   4440
```

```
agtgctgcaa tgataccgcg agacccacgc tcaccggctc cagatttatc agcaataaac   4500
cagccagccg gaagggccga gcgcagaagt ggtcctgcaa ctttatccgc ctccatccag   4560
tctattaatt gttgccggga agctagagta agtagttcgc cagttaatag tttgcgcaac   4620
gttgttgcca ttgctacagg catcgtggtg tcacgctcgt cgtttggtat ggcttcattc   4680
agctccggtt cccaacgatc aaggcgagtt acatgatccc ccatgttgtg caaaaaagcg   4740
gttagctcct tcggtcctcc gatcgttgtc agaagtaagt tggccgcagt gttatcactc   4800
atggttatgg cagcactgca taattctctt actgtcatgc catccgtaag atgcttttct   4860
gtgactggtg agtactcaac caagtcattc tgagaatagt gtatgcggcg accgagttgc   4920
tcttgcccgg cgtcaatacg ggataatacc gcgccacata gcagaacttt aaaagtgctc   4980
atcattggaa aacgttcttc ggggcgaaaa ctctcaagga tcttaccgct gttgagatcc   5040
agttcgatgt aacccactcg tgcacccaac tgatcttcag catcttttac tttcaccagc   5100
gtttctgggt gagcaaaaac aggaaggcaa aatgccgcaa aaaagggaat aagggcgaca   5160
cggaaatgtt gaatactcat actcttcctt tttcaatatt attgaagcat ttatcagggt   5220
tattgtctca tgagcggata catatttgaa tgtatttaga aaaataaaca aataggggtt   5280
ccgcgcacat ttccccgaaa agtgccac                                       5308
```

<210> SEQ ID NO 37
<211> LENGTH: 5296
<212> TYPE: DNA
<213> ORGANISM: Artificial
<220> FEATURE:
<223> OTHER INFORMATION: Plasmid pGSH0_OshRNA_Tyr1C

<400> SEQUENCE: 37

```
ctaaattgta agcgttaata ttttgttaaa attcgcgtta aatttttgtt aaatcagctc     60
atttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgtagggat aacagggtaa tgcgcgcgta atacgactca    660
ctatagggcg aattgggtac cgggcccccc ctcgaccata gccaattcaa tatggcgtat    720
atggactcat gccaattcaa tatggtggat ctggacctgt gccaattcaa tatggcgtat    780
atggactcgt gccaattcaa tatggtggat ctggacccca gccaattcaa tatggcggac    840
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
```

-continued

```
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac taatgcatcc agacaaagag gctgtgaagc agttgaaggg   2280
cctctttgag gatgcactag ctgccaactg ccttcgacgc gtagcttccc ttaatacaag   2340
tgagatgatg gcataccatc tttcgggact gagttgatgt gaagagtttt tctgttttgc   2400
tgatcacttg tatattatgt gactaatagt taaagtgcca aaataaaatg tgggaacatt   2460
gaatgtgtat cctacttaag ggaatcgatt tcaaggagga cggaaacatc ctcggccaca   2520
agttggaata caactacaac tcccacaacg tatacatcat ggccgacaag caaaagaacg   2580
gcatcaaagc caacttcaag acccgccaca acatcgaaga cggcggcgtg caactcgctg   2640
atcattatca acaaaatact ccaattggcg atgaccctgt ccttttacca gacaaccatt   2700
acctgtccac acaatctgcc ctttcgaaag atcccaacga aaagagagac cacatggtcc   2760
ttcttgagtt tgtaacggct gctgggatta cacatggcat ggatgaacta tacaaaaatc   2820
tagaactata gtgagtcgta ttacgtagat ccagacatga taagatacat tgatgagttt   2880
ggacaaacca caactagaat gcagtgaaaa aaatgcttta tttgtgaaat ttgtgatgct   2940
attgctttat ttgtaaccat tataagctgc aataaacaag ttaacaacaa caattgcatt   3000
cattttatgt ttcaggttca gggggaggtg tgggaggttt tttaattcgc ggccgccacc   3060
gcggtggagc tccagctttt gttcccttta gtgagggtta attgcgcgca ttaccctgtt   3120
atccctacgc gcttggcgta atcatggtca tagctgtttc ctgtgtgaaa ttgttatccg   3180
ctcacaattc cacacaacat acgagccgga agcataaagt gtaaagcctg gggtgcctaa   3240
tgagtgagct aactcacatt aattgcgttg cgctcactgc ccgctttcca gtcgggaaac   3300
ctgtcgtgcc agctgcatta atgaatcggc caacgcgcgg ggagaggcgg tttgcgtatt   3360
gggcgctctt ccgcttcctc gctcactgac tcgctgcgct cggtcgttcg gctgcggcga   3420
gcggtatcag ctcactcaaa ggcggtaata cggttatcca cagaatcagg ggataacgca   3480
ggaaagaaca tgtgagcaaa aggccagcaa aaggccagga accgtaaaaa ggccgcgttg   3540
```

```
ctggcgtttt tccataggct ccgcccccct gacgagcatc acaaaaatcg acgctcaagt   3600

cagaggtggc gaaacccgac aggactataa agataccagg cgtttccccc tggaagctcc   3660

ctcgtgcgct ctcctgttcc gaccctgccg cttaccggat acctgtccgc ctttctccct   3720

tcgggaagcg tggcgctttc tcatagctca cgctgtaggt atctcagttc ggtgtaggtc   3780

gttcgctcca agctgggctg tgtgcacgaa ccccccgttc agcccgaccg ctgcgcctta   3840

tccggtaact atcgtcttga gtccaacccg gtaagacacg acttatcgcc actggcagca   3900

gccactggta acaggattag cagagcgagg tatgtaggcg gtgctacaga gttcttgaag   3960

tggtggccta actacggcta cactagaaga acagtatttg gtatctgcgc tctgctgaag   4020

ccagttacct tcggaaaaag agttggtagc tcttgatccg gcaaacaaac caccgctggt   4080

agcggtggtt tttttgtttg caagcagcag attacgcgca gaaaaaaagg atctcaagaa   4140

gatcctttga tcttttctac ggggtctgac gctcagtgga acgaaaactc acgttaaggg   4200

attttggtca tgagattatc aaaaaggatc ttcacctaga tccttttaaa ttaaaaatga   4260

agttttaaat caatctaaag tatatatgag taaacttggt ctgacagtta ccaatgctta   4320

atcagtgagg cacctatctc agcgatctgt ctatttcgtt catccatagt tgcctgactc   4380

cccgtcgtgt agataactac gatacgggag ggcttaccat ctggccccag tgctgcaatg   4440

ataccgcgag acccacgctc accggctcca gatttatcag caataaacca gccagccgga   4500

agggccgagc gcagaagtgg tcctgcaact ttatccgcct ccatccagtc tattaattgt   4560

tgccgggaag ctagagtaag tagttcgcca gttaatagtt tgcgcaacgt tgttgccatt   4620

gctacaggca tcgtggtgtc acgctcgtcg tttggtatgg cttcattcag ctccggttcc   4680

caacgatcaa ggcgagttac atgatccccc atgttgtgca aaaaagcggt tagctccttc   4740

ggtcctccga tcgttgtcag aagtaagttg gccgcagtgt tatcactcat ggttatggca   4800

gcactgcata attctcttac tgtcatgcca tccgtaagat gcttttctgt gactggtgag   4860

tactcaacca agtcattctg agaatagtgt atgcggcgac cgagttgctc ttgcccggcg   4920

tcaatacggg ataataccgc gccacatagc agaactttaa aagtgctcat cattggaaaa   4980

cgttcttcgg ggcgaaaact ctcaaggatc ttaccgctgt tgagatccag ttcgatgtaa   5040

cccactcgtg cacccaactg atcttcagca tcttttactt tcaccagcgt ttctgggtga   5100

gcaaaaacag gaaggcaaaa tgccgcaaaa aagggaataa gggcgacacg gaaatgttga   5160

atactcatac tcttcctttt tcaatattat tgaagcattt atcagggtta ttgtctcatg   5220

agcggataca tatttgaatg tatttagaaa aataaacaaa taggggttcc gcgcacattt   5280

ccccgaaaag tgccac                                                    5296
```

<210> SEQ ID NO 38
<211> LENGTH: 5308
<212> TYPE: DNA
<213> ORGANISM: Artificial
<220> FEATURE:
<223> OTHER INFORMATION: Plasmid pGSH0_OshRNA_Tyr2C

<400> SEQUENCE: 38

```
ctaaattgta agcgttaata ttttgttaaa attcgcgtta aatttttgtt aaatcagctc     60

atttttttaac caataggccg aaatcggcaa aatcccttat aaatcaaaag aatagaccga   120

gatagggttg agtgttgttc cagtttggaa caagagtcca ctattaaaga acgtggactc   180

caacgtcaaa gggcgaaaaa ccgtctatca gggcgatggc ccactacgtg aaccatcacc   240
```

-continued

```
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgtagggat aacagggtaa tgcgcgcgta atacgactca    660
ctatagggcg aattgggtac cgggcccccc ctcgaccata gccaattcaa tatggcgtat    720
atggactcat gccaattcaa tatggtggat ctggacctgt gccaattcaa tatggcgtat    780
atggactcgt gccaattcaa tatggtggat ctggacccca gccaattcaa tatggcggac    840
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac tcaatgtctc tccagagagc atctgtgaag cagttgaagg   2280
gatgctctct cgagacatcg agctgccaac tgccttcgat gcatcttcac gcgtagcttc   2340
ccttaataca agtgagatga tggcatacca tctttcggga ctgagttgat gtgaagagtt   2400
tttctgtttt gctgatcact tgtatattat gtgactaata gttaaagtgc caaaataaaa   2460
tgtgggaaca ttgaatgtgt atcctactta agggaatcga tttcaaggag gacggaaaca   2520
tcctcggcca caagttggaa tacaactaca actcccacaa cgtatacatc atggccgaca   2580
agcaaaagaa cggcatcaaa gccaacttca agacccgcca caacatcgaa gacggcggcg   2640
```

tgcaactcgc tgatcattat caacaaaata ctccaattgg cgatgaccct gtccttttac 2700
cagacaacca ttacctgtcc acacaatctg ccctttcgaa agatcccaac gaaaagagag 2760
accacatggt ccttcttgag tttgtaacgg ctgctgggat tacacatggc atggatgaac 2820
tatacaaaaa tctagaacta tagtgagtcg tattacgtag atccagacat gataagatac 2880
attgatgagt ttggacaaac cacaactaga atgcagtgaa aaaaatgctt tatttgtgaa 2940
atttgtgatg ctattgcttt atttgtaacc attataagct gcaataaaca agttaacaac 3000
aacaattgca ttcattttat gtttcaggtt cagggggagg tgtgggaggt tttttaattc 3060
gcggccgcca ccgcggtgga gctccagctt ttgttccctt tagtgagggt taattgcgcg 3120
cattaccctg ttatccctac gcgcttggcg taatcatggt catagctgtt tcctgtgtga 3180
aattgttatc cgctcacaat tccacacaac atacgagccg gaagcataaa gtgtaaagcc 3240
tggggtgcct aatgagtgag ctaactcaca ttaattgcgt tgcgctcact gcccgctttc 3300
cagtcgggaa acctgtcgtg ccagctgcat taatgaatcg gccaacgcgc ggggagaggc 3360
ggtttgcgta ttgggcgctc ttccgcttcc tcgctcactg actcgctgcg ctcggtcgtt 3420
cggctgcggc gagcggtatc agctcactca aaggcggtaa tacggttatc cacagaatca 3480
ggggataacg caggaaagaa catgtgagca aaaggccagc aaaaggccag gaaccgtaaa 3540
aaggccgcgt tgctggcgtt tttccatagg ctccgccccc ctgacgagca tcacaaaaat 3600
cgacgctcaa gtcagaggtg gcgaaacccg acaggactat aaagatacca ggcgtttccc 3660
cctggaagct ccctcgtgcg ctctcctgtt ccgaccctgc cgcttaccgg atacctgtcc 3720
gcctttctcc cttcgggaag cgtggcgctt tctcatagct cacgctgtag gtatctcagt 3780
tcggtgtagg tcgttcgctc caagctgggc tgtgtgcacg aaccccccgt tcagcccgac 3840
cgctgcgcct tatccggtaa ctatcgtctt gagtccaacc cggtaagaca cgacttatcg 3900
ccactggcag cagccactgg taacaggatt agcagagcga ggtatgtagg cggtgctaca 3960
gagttcttga agtggtggcc taactacggc tacactagaa gaacagtatt tggtatctgc 4020
gctctgctga agccagttac cttcggaaaa agagttggta gctcttgatc cggcaaacaa 4080
accaccgctg gtagcggtgg tttttttgtt tgcaagcagc agattacgcg cagaaaaaaa 4140
ggatctcaag aagatccttt gatcttttct acggggtctg acgctcagtg gaacgaaaac 4200
tcacgttaag ggattttggt catgagatta tcaaaaagga tcttcaccta gatcctttta 4260
aattaaaaat gaagttttaa atcaatctaa agtatatatg agtaaacttg gtctgacagt 4320
taccaatgct taatcagtga ggcacctatc tcagcgatct gtctatttcg ttcatccata 4380
gttgcctgac tccccgtcgt gtagataact acgatacggg agggcttacc atctggcccc 4440
agtgctgcaa tgataccgcg agacccacgc tcaccggctc cagatttatc agcaataaac 4500
cagccagccg gaagggccga gcgcagaagt ggtcctgcaa ctttatccgc ctccatccag 4560
tctattaatt gttgccggga agctagagta agtagttcgc cagttaatag tttgcgcaac 4620
gttgttgcca ttgctacagg catcgtggtg tcacgctcgt cgtttggtat ggcttcattc 4680
agctccggtt cccaacgatc aaggcgagtt acatgatccc ccatgttgtg caaaaaagcg 4740
gttagctcct tcggtcctcc gatcgttgtc agaagtaagt tggccgcagt gttatcactc 4800
atggttatgg cagcactgca taattctctt actgtcatgc catccgtaag atgcttttct 4860
gtgactggtg agtactcaac caagtcattc tgagaatagt gtatgcggcg accgagttgc 4920
tcttgcccgg cgtcaatacg ggataatacc gcgccacata gcagaacttt aaaagtgctc 4980

```
atcattggaa aacgttcttc ggggcgaaaa ctctcaagga tcttaccgct gttgagatcc   5040

agttcgatgt aacccactcg tgcacccaac tgatcttcag catcttttac tttcaccagc   5100

gtttctgggt gagcaaaaac aggaaggcaa aatgccgcaa aaaagggaat aagggcgaca   5160

cggaaatgtt gaatactcat actcttcctt tttcaatatt attgaagcat ttatcagggt   5220

tattgtctca tgagcggata catatttgaa tgtatttaga aaaataaaca aataggggtt   5280

ccgcgcacat ttccccgaaa agtgccac                                      5308
```

```
<210> SEQ ID NO 39
<211> LENGTH: 5306
<212> TYPE: DNA
<213> ORGANISM: Artificial
<220> FEATURE:
<223> OTHER INFORMATION: Plasmid pGSH0_OshRNA_Tyr3C

<400> SEQUENCE: 39
```

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgtagggat aacagggtaa tgcgcgcgta atacgactca    660

ctatagggcg aattgggtac cgggcccccc ctcgaccata gccaattcaa tatggcgtat    720

atggactcat gccaattcaa tatggtggat ctggacctgt gccaattcaa tatggcgtat    780

atggactcgt gccaattcaa tatggtggat ctggacccca gccaattcaa tatggcggac    840

ttggcaccat gccaattcaa tatggcggac ttggcactgt gccaactggg gaggggtcta    900

cttggcacgg tgccaagttt gaggaggggt cttggccctg tgccaagtcc gccatattga    960

attggcatgg tgccaataat ggcggccata ttggctatat gccaggatca atatataggc   1020

aatatccaat atggccctat gccaatatgg ctattggcca ggttcaatac tatgtattgg   1080

ccctatgcca tatagtattc catatatggg ttttcctatt gacgtagata gcccctccca   1140

atgggcggtc ccatatacca tatatggggc ttcctaatac cgcccatagc cactccccca   1200

ttgacgtcaa tggtctctat atatggtctt tcctattgac gtcatatggg cggtcctatt   1260

gacgtatatg gcgcctcccc cattgacgtc aattacggta aatggcccgc ctggctcaat   1320

gcccattgac gtcaatagga ccacccacca ttgacgtcaa tgggatggct cattgcccat   1380

tcatatccgt tctcacgccc cctattgacg tcaatgacgg taaatggccc acttggcagt   1440

acatcaatat ctattaatag taacttggca agtacattac tattggaagt acgccagggt   1500

acattggcag tactcccatt gacgtcaatg gcggtaaatg gcccgcgatg gctgccaagt   1560

acatccccat tgacgtcaat ggggaggggc aatgacgcaa atgggcgttc cattgacgta   1620

aatgggcggt aggcgtgcct aatgggaggt ctatataagc aatgctcgtt tagggaaccg   1680

ccattctgcc tggggacgtc ggagcaagct agcttgcttg ttctttttgc agaagctcag   1740
```

-continued

```
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac tgttcccagt gcagcaggaa gctgtgaagc agttgaaggg   2280
cttcctgcaa ctgggaccag ctgccaactg ccttcgatgc atcttcacgc gtagcttccc   2340
ttaatacaag tgagatgatg gcataccatc tttcgggact gagttgatgt gaagagtttt   2400
tctgttttgc tgatcacttg tatattatgt gactaatagt taaagtgcca aaataaaatg   2460
tgggaacatt gaatgtgtat cctacttaag ggaatcgatt tcaaggagga cggaaacatc   2520
ctcggccaca agttggaata caactacaac tcccacaacg tatacatcat ggccgacaag   2580
caaaagaacg gcatcaaagc caacttcaag acccgccaca acatcgaaga cggcggcgtg   2640
caactcgctg atcattatca acaaaatact ccaattggcg atgaccctgt ccttttacca   2700
gacaaccatt acctgtccac acaatctgcc ctttcgaaag atcccaacga aaagagagac   2760
cacatggtcc ttcttgagtt tgtaacggct gctgggatta cacatggcat ggatgaacta   2820
tacaaaaatc tagaactata gtgagtcgta ttacgtagat ccagacatga taagatacat   2880
tgatgagttt ggacaaacca caactagaat gcagtgaaaa aaatgcttta tttgtgaaat   2940
ttgtgatgct attgctttat ttgtaaccat tataagctgc aataaacaag ttaacaacaa   3000
caattgcatt cattttatgt ttcaggttca gggggaggtg tgggaggttt tttaattcgc   3060
ggccgccacc gcggtggagc tccagctttt gttcccttta gtgagggtta attgcgcgca   3120
ttaccctgtt atccctacgc gcttggcgta atcatggtca tagctgtttc ctgtgtgaaa   3180
ttgttatccg ctcacaattc cacacaacat acgagccgga agcataaagt gtaaagcctg   3240
gggtgcctaa tgagtgagct aactcacatt aattgcgttg cgctcactgc ccgctttcca   3300
gtcgggaaac ctgtcgtgcc agctgcatta atgaatcggc caacgcgcgg ggagaggcgg   3360
tttgcgtatt gggcgctctt ccgcttcctc gctcactgac tcgctgcgct cggtcgttcg   3420
gctgcggcga gcggtatcag ctcactcaaa ggcggtaata cggttatcca cagaatcagg   3480
ggataacgca ggaaagaaca tgtgagcaaa aggccagcaa aaggccagga accgtaaaaa   3540
ggccgcgttg ctggcgtttt tccataggct ccgcccccct gacgagcatc acaaaaatcg   3600
acgctcaagt cagaggtggc gaaacccgac aggactataa agataccagg cgtttccccc   3660
tggaagctcc ctcgtgcgct ctcctgttcc gaccctgccg cttaccggat acctgtccgc   3720
ctttctccct tcgggaagcg tggcgctttc tcatagctca cgctgtaggt atctcagttc   3780
ggtgtaggtc gttcgctcca agctgggctg tgtgcacgaa ccccccgttc agcccgaccg   3840
ctgcgcctta tccggtaact atcgtcttga gtccaacccg gtaagacacg acttatcgcc   3900
actggcagca gccactggta acaggattag cagagcgagg tatgtaggcg gtgctacaga   3960
gttcttgaag tggtggccta actacggcta cactagaaga acagtatttg gtatctgcgc   4020
tctgctgaag ccagttacct tcggaaaaag agttggtagc tcttgatccg gcaaacaaac   4080
```

```
caccgctggt agcggtggtt tttttgtttg caagcagcag attacgcgca gaaaaaaagg   4140
atctcaagaa gatcctttga tcttttctac ggggtctgac gctcagtgga acgaaaactc   4200
acgttaaggg attttggtca tgagattatc aaaaaggatc ttcacctaga tccttttaaa   4260
ttaaaaatga agttttaaat caatctaaag tatatatgag taaacttggt ctgacagtta   4320
ccaatgctta atcagtgagg cacctatctc agcgatctgt ctatttcgtt catccatagt   4380
tgcctgactc cccgtcgtgt agataactac gatacgggag ggcttaccat ctggccccag   4440
tgctgcaatg ataccgcgag acccacgctc accggctcca gatttatcag caataaacca   4500
gccagccgga agggccgagc gcagaagtgg tcctgcaact ttatccgcct ccatccagtc   4560
tattaattgt tgccgggaag ctagagtaag tagttcgcca gttaatagtt tgcgcaacgt   4620
tgttgccatt gctacaggca tcgtggtgtc acgctcgtcg tttggtatgg cttcattcag   4680
ctccggttcc caacgatcaa ggcgagttac atgatccccc atgttgtgca aaaaagcggt   4740
tagctccttc ggtcctccga tcgttgtcag aagtaagttg gccgcagtgt tatcactcat   4800
ggttatggca gcactgcata attctcttac tgtcatgcca tccgtaagat gcttttctgt   4860
gactggtgag tactcaacca agtcattctg agaatagtgt atgcggcgac cgagttgctc   4920
ttgcccggcg tcaatacggg ataataccgc gccacatagc agaactttaa aagtgctcat   4980
cattggaaaa cgttcttcgg ggcgaaaact ctcaaggatc ttaccgctgt tgagatccag   5040
ttcgatgtaa cccactcgtg cacccaactg atcttcagca tcttttactt tcaccagcgt   5100
ttctgggtga gcaaaaacag gaaggcaaaa tgccgcaaaa aagggaataa gggcgacacg   5160
gaaatgttga atactcatac tcttcctttt tcaatattat tgaagcattt atcagggtta   5220
ttgtctcatg agcggataca tatttgaatg tatttagaaa aataaacaaa taggggttcc   5280
gcgcacattt ccccgaaaag tgccac                                        5306
```

<210> SEQ ID NO 40
<211> LENGTH: 5308
<212> TYPE: DNA
<213> ORGANISM: Artificial
<220> FEATURE:
<223> OTHER INFORMATION: Plasmid pGSH0_OshRNA_Tyr4C

<400> SEQUENCE: 40

```
ctaaattgta agcgttaata ttttgttaaa attcgcgtta aatttttgtt aaatcagctc     60
atttttaacc aataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgtagggat aacagggtaa tgcgcgcgta atacgactca    660
ctatagggcg aattgggtac cgggcccccc ctcgaccata gccaattcaa tatggcgtat    720
atggactcat gccaattcaa tatggtggat ctggacctgt gccaattcaa tatggcgtat    780
atggactcgt gccaattcaa tatggtggat ctggacccca gccaattcaa tatggcggac    840
```

-continued

```
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac taatccttct agggtgttcc tgctgtgaag cagttgaagg   2280
gcaggaacac cagaaggagt agctgccaac tgccttcgat gcatcttcac gcgtagcttc   2340
ccttaataca agtgagatga tggcatacca tctttcggga ctgagttgat gtgaagagtt   2400
tttctgtttt gctgatcact tgtatattat gtgactaata gttaaagtgc caaaataaaa   2460
tgtgggaaca ttgaatgtgt atcctactta agggaatcga tttcaaggag gacggaaaca   2520
tcctcggcca caagttggaa tacaactaca actcccacaa cgtatacatc atggccgaca   2580
agcaaaagaa cggcatcaaa gccaacttca agacccgcca caacatcgaa gacggcggcg   2640
tgcaactcgc tgatcattat caacaaaata ctccaattgg cgatgaccct gtccttttac   2700
cagacaacca ttacctgtcc acacaatctg ccctttcgaa agatcccaac gaaaagagag   2760
accacatggt ccttcttgag tttgtaacgg ctgctgggat tacacatggc atggatgaac   2820
tatacaaaaa tctagaacta tagtgagtcg tattacgtag atccagacat gataagatac   2880
attgatgagt ttggacaaac cacaactaga atgcagtgaa aaaaatgctt tatttgtgaa   2940
atttgtgatg ctattgcttt atttgtaacc attataagct gcaataaaca agttaacaac   3000
aacaattgca ttcattttat gtttcaggtt cagggggagg tgtgggaggt tttttaattc   3060
gcggccgcca ccgcggtgga gctccagctt ttgttccctt tagtgagggt taattgcgcg   3120
cattaccctg ttatccctac gcgcttggcg taatcatggt catagctgtt tcctgtgtga   3180
```

-continued

```
aattgttatc cgctcacaat tccacacaac atacgagccg gaagcataaa gtgtaaagcc   3240

tggggtgcct aatgagtgag ctaactcaca ttaattgcgt tgcgctcact gcccgctttc   3300

cagtcgggaa acctgtcgtg ccagctgcat taatgaatcg gccaacgcgc ggggagaggc   3360

ggtttgcgta ttgggcgctc ttccgcttcc tcgctcactg actcgctgcg ctcggtcgtt   3420

cggctgcggc gagcggtatc agctcactca aaggcggtaa tacggttatc cacagaatca   3480

ggggataacg caggaaagaa catgtgagca aaaggccagc aaaaggccag gaaccgtaaa   3540

aaggccgcgt tgctggcgtt tttccatagg ctccgccccc ctgacgagca tcacaaaaat   3600

cgacgctcaa gtcagaggtg gcgaaacccg acaggactat aaagatacca ggcgtttccc   3660

cctggaagct ccctcgtgcg ctctcctgtt ccgaccctgc cgcttaccgg atacctgtcc   3720

gcctttctcc cttcgggaag cgtggcgctt tctcatagct cacgctgtag gtatctcagt   3780

tcggtgtagg tcgttcgctc caagctgggc tgtgtgcacg aaccccccgt tcagcccgac   3840

cgctgcgcct tatccggtaa ctatcgtctt gagtccaacc cggtaagaca cgacttatcg   3900

ccactggcag cagccactgg taacaggatt agcagagcga ggtatgtagg cggtgctaca   3960

gagttcttga agtggtggcc taactacggc tacactagaa gaacagtatt tggtatctgc   4020

gctctgctga agccagttac cttcggaaaa agagttggta gctcttgatc cggcaaacaa   4080

accaccgctg gtagcggtgg tttttttgtt tgcaagcagc agattacgcg cagaaaaaaa   4140

ggatctcaag aagatccttt gatcttttct acggggtctg acgctcagtg gaacgaaaac   4200

tcacgttaag ggattttggt catgagatta tcaaaaagga tcttcaccta gatcctttta   4260

aattaaaaat gaagttttaa atcaatctaa agtatatatg agtaaacttg gtctgacagt   4320

taccaatgct taatcagtga ggcacctatc tcagcgatct gtctatttcg ttcatccata   4380

gttgcctgac tccccgtcgt gtagataact acgatacggg agggcttacc atctggcccc   4440

agtgctgcaa tgataccgcg agacccacgc tcaccggctc cagatttatc agcaataaac   4500

cagccagccg gaagggccga gcgcagaagt ggtcctgcaa ctttatccgc ctccatccag   4560

tctattaatt gttgccggga agctagagta agtagttcgc cagttaatag tttgcgcaac   4620

gttgttgcca ttgctacagg catcgtggtg tcacgctcgt cgtttggtat ggcttcattc   4680

agctccggtt cccaacgatc aaggcgagtt acatgatccc ccatgttgtg caaaaaagcg   4740

gttagctcct tcggtcctcc gatcgttgtc agaagtaagt tggccgcagt gttatcactc   4800

atggttatgg cagcactgca taattctctt actgtcatgc catccgtaag atgcttttct   4860

gtgactggtg agtactcaac caagtcattc tgagaatagt gtatgcggcg accgagttgc   4920

tcttgcccgg cgtcaatacg ggataatacc gcgccacata gcagaacttt aaaagtgctc   4980

atcattggaa aacgttcttc ggggcgaaaa ctctcaagga tcttaccgct gttgagatcc   5040

agttcgatgt aacccactcg tgcacccaac tgatcttcag catcttttac tttcaccagc   5100

gtttctgggt gagcaaaaac aggaaggcaa aatgccgcaa aaaagggaat aagggcgaca   5160

cggaaatgtt gaatactcat actcttcctt tttcaatatt attgaagcat ttatcagggt   5220

tattgtctca tgagcggata catatttgaa tgtatttaga aaaataaaca aataggggtt   5280

ccgcgcacat ttccccgaaa agtgccac                                      5308
```

<210> SEQ ID NO 41
<211> LENGTH: 5308
<212> TYPE: DNA
<213> ORGANISM: Artificial
<220> FEATURE:
<223> OTHER INFORMATION: Plasmid pGSH0_OshRNA_Tyr5C

<400> SEQUENCE: 41

```
ctaaattgta agcgttaata ttttgttaaa attcgcgtta aatttttgtt aaatcagctc     60
atttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgtagggat aacagggtaa tgcgcgcgta atacgactca    660
ctatagggcg aattgggtac cgggcccccc ctcgaccata gccaattcaa tatggcgtat    720
atggactcat gccaattcaa tatggtggat ctggacctgt gccaattcaa tatggcgtat    780
atggactcgt gccaattcaa tatggtggat ctggacccca gccaattcaa tatggcggac    840
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac taggtgggac cccctgctca ccctgtgaag cagttgaagg   2280
```

-continued gggtgagcag agtcccactt agctgccaac tgccttcgat gcatcttcac gcgtagcttc 2340
ccttaataca agtgagatga tggcatacca tctttcggga ctgagttgat gtgaagagtt 2400
tttctgtttt gctgatcact tgtatattat gtgactaata gttaaagtgc caaaataaaa 2460
tgtgggaaca ttgaatgtgt atcctactta agggaatcga tttcaaggag gacggaaaca 2520
tcctcggcca caagttggaa tacaactaca actcccacaa cgtatacatc atggccgaca 2580
agcaaaagaa cggcatcaaa gccaacttca agacccgcca caacatcgaa gacggcggcg 2640
tgcaactcgc tgatcattat caacaaaata ctccaattgg cgatgaccct gtccttttac 2700
cagacaacca ttacctgtcc acacaatctg ccctttcgaa agatcccaac gaaaagagag 2760
accacatggt ccttcttgag tttgtaacgg ctgctgggat tacacatggc atggatgaac 2820
tatacaaaaa tctagaacta tagtgagtcg tattacgtag atccagacat gataagatac 2880
attgatgagt ttggacaaac cacaactaga atgcagtgaa aaaaatgctt tatttgtgaa 2940
atttgtgatg ctattgcttt atttgtaacc attataagct gcaataaaca agttaacaac 3000
aacaattgca ttcattttat gtttcaggtt cagggggagg tgtgggaggt tttttaattc 3060
gcggccgcca ccgcggtgga gctccagctt ttgttccctt tagtgagggt taattgcgcg 3120
cattaccctg ttatccctac gcgcttggcg taatcatggt catagctgtt tcctgtgtga 3180
aattgttatc cgctcacaat tccacacaac atacgagccg gaagcataaa gtgtaaagcc 3240
tggggtgcct aatgagtgag ctaactcaca ttaattgcgt tgcgctcact gcccgctttc 3300
cagtcgggaa acctgtcgtg ccagctgcat taatgaatcg gccaacgcgc ggggagaggc 3360
ggtttgcgta ttgggcgctc ttccgcttcc tcgctcactg actcgctgcg ctcggtcgtt 3420
cggctgcggc gagcggtatc agctcactca aaggcggtaa tacggttatc cacagaatca 3480
ggggataacg caggaaagaa catgtgagca aaaggccagc aaaaggccag gaaccgtaaa 3540
aaggccgcgt tgctggcgtt tttccatagg ctccgccccc ctgacgagca tcacaaaaat 3600
cgacgctcaa gtcagaggtg gcgaaacccg acaggactat aaagatacca ggcgtttccc 3660
cctggaagct ccctcgtgcg ctctcctgtt ccgaccctgc cgcttaccgg atacctgtcc 3720
gcctttctcc cttcgggaag cgtggcgctt tctcatagct cacgctgtag gtatctcagt 3780
tcggtgtagg tcgttcgctc caagctgggc tgtgtgcacg aaccccccgt tcagcccgac 3840
cgctgcgcct tatccggtaa ctatcgtctt gagtccaacc cggtaagaca cgacttatcg 3900
ccactggcag cagccactgg taacaggatt agcagagcga ggtatgtagg cggtgctaca 3960
gagttcttga agtggtggcc taactacggc tacactagaa gaacagtatt tggtatctgc 4020
gctctgctga agccagttac cttcggaaaa agagttggta gctcttgatc cggcaaacaa 4080
accaccgctg gtagcggtgg tttttttgtt tgcaagcagc agattacgcg cagaaaaaaa 4140
ggatctcaag aagatccttt gatcttttct acggggtctg acgctcagtg gaacgaaaac 4200
tcacgttaag ggattttggt catgagatta tcaaaaagga tcttcaccta gatcctttta 4260
aattaaaaat gaagttttaa atcaatctaa agtatatatg agtaaacttg gtctgacagt 4320
taccaatgct taatcagtga ggcacctatc tcagcgatct gtctatttcg ttcatccata 4380
gttgcctgac tccccgtcgt gtagataact acgatacggg agggcttacc atctggcccc 4440
agtgctgcaa tgataccgcg agacccacgc tcaccggctc cagatttatc agcaataaac 4500
cagccagccg gaagggccga gcgcagaagt ggtcctgcaa ctttatccgc ctccatccag 4560
tctattaatt gttgccggga agctagagta agtagttcgc cagttaatag tttgcgcaac 4620
gttgttgcca ttgctacagg catcgtggtg tcacgctcgt cgtttggtat ggcttcattc 4680

```
agctccggtt cccaacgatc aaggcgagtt acatgatccc ccatgttgtg caaaaaagcg   4740

gttagctcct tcggtcctcc gatcgttgtc agaagtaagt tggccgcagt gttatcactc   4800

atggttatgg cagcactgca taattctctt actgtcatgc catccgtaag atgcttttct   4860

gtgactggtg agtactcaac caagtcattc tgagaatagt gtatgcggcg accgagttgc   4920

tcttgcccgg cgtcaatacg ggataatacc gcgccacata gcagaacttt aaaagtgctc   4980

atcattggaa aacgttcttc ggggcgaaaa ctctcaagga tcttaccgct gttgagatcc   5040

agttcgatgt aacccactcg tgcacccaac tgatcttcag catcttttac tttcaccagc   5100

gtttctgggt gagcaaaaac aggaaggcaa aatgccgcaa aaaagggaat aagggcgaca   5160

cggaaatgtt gaatactcat actcttcctt tttcaatatt attgaagcat ttatcagggt   5220

tattgtctca tgagcggata catatttgaa tgtatttaga aaaataaaca aataggggtt   5280

ccgcgcacat ttccccgaaa agtgccac                                      5308
```

```
<210> SEQ ID NO 42
<211> LENGTH: 5308
<212> TYPE: DNA
<213> ORGANISM: Artificial
<220> FEATURE:
<223> OTHER INFORMATION: Plasmid pGSH0_OshRNA_Tyr6C

<400> SEQUENCE: 42

ctaaattgta agcgttaata ttttgttaaa attcgcgtta aatttttgtt aaatcagctc     60

atttttaac caataggccg aaatcggcaa aatcccttat aaatcaaaag aatagaccga     120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgtagggat aacagggtaa tgcgcgcgta atacgactca    660

ctatagggcg aattgggtac cggccccccc ctcgaccata gccaattcaa tatggcgtat    720

atggactcat gccaattcaa tatggtggat ctggacctgt gccaattcaa tatggcgtat    780

atggactcgt gccaattcaa tatggtggat ctggacccca gccaattcaa tatggcggac    840

ttggcaccat gccaattcaa tatggcggac ttggcactgt gccaactggg gaggggtcta    900

cttggcacgg tgccaagttt gaggaggggt cttggccctg tgccaagtcc gccatattga    960

attggcatgg tgccaataat ggcggccata ttggctatat gccaggatca atatataggc   1020

aatatccaat atggccctat gccaatatgg ctattggcca ggttcaatac tatgtattgg   1080

ccctatgcca tatagtattc catatatggg ttttcctatt gacgtagata gcccctccca   1140

atgggcggtc ccatatacca tatatggggc ttcctaatac cgcccatagc cactccccca   1200

ttgacgtcaa tggtctctat atatggtctt tcctattgac gtcatatggg cggtcctatt   1260

gacgtatatg gcgcctcccc cattgacgtc aattacggta aatggcccgc ctggctcaat   1320

gcccattgac gtcaatagga ccacccacca ttgacgtcaa tgggatggct cattgcccat   1380
```

-continued

```
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtatgcgac ttgggaaagt cccagtgggc cgctgtgaag cagttgaagg   2280
gcggcccact cactttccta agctgccaac tgccttcgat gcatcttcac gcgtagcttc   2340
ccttaataca agtgagatga tggcatacca tctttcggga ctgagttgat gtgaagagtt   2400
tttctgtttt gctgatcact tgtatattat gtgactaata gttaaagtgc caaaataaaa   2460
tgtgggaaca ttgaatgtgt atcctactta agggaatcga tttcaaggag gacggaaaca   2520
tcctcggcca caagttggaa tacaactaca actcccacaa cgtatacatc atggccgaca   2580
agcaaaagaa cggcatcaaa gccaacttca agacccgcca caacatcgaa gacggcggcg   2640
tgcaactcgc tgatcattat caacaaaata ctccaattgg cgatgaccct gtccttttac   2700
cagacaacca ttacctgtcc acacaatctg ccctttcgaa agatcccaac gaaaagagag   2760
accacatggt ccttcttgag tttgtaacgg ctgctgggat tacacatggc atggatgaac   2820
tatacaaaaa tctagaacta tagtgagtcg tattacgtag atccagacat gataagatac   2880
attgatgagt ttggacaaac cacaactaga atgcagtgaa aaaaatgctt tatttgtgaa   2940
atttgtgatg ctattgcttt atttgtaacc attataagct gcaataaaca agttaacaac   3000
aacaattgca ttcattttat gtttcaggtt cagggggagg tgtgggaggt tttttaattc   3060
gcggccgcca ccgcggtgga gctccagctt ttgttccctt tagtgagggt taattgcgcg   3120
cattaccctg ttatccctac gcgcttggcg taatcatggt catagctgtt tcctgtgtga   3180
aattgttatc cgctcacaat tccacacaac atacgagccg gaagcataaa gtgtaaagcc   3240
tggggtgcct aatgagtgag ctaactcaca ttaattgcgt tgcgctcact gcccgctttc   3300
cagtcgggaa acctgtcgtg ccagctgcat taatgaatcg gccaacgcgc ggggagaggc   3360
ggtttgcgta ttgggcgctc ttccgcttcc tcgctcactg actcgctgcg ctcggtcgtt   3420
cggctgcggc gagcggtatc agctcactca aaggcggtaa tacggttatc cacagaatca   3480
ggggataacg caggaaagaa catgtgagca aaaggccagc aaaaggccag gaaccgtaaa   3540
aaggccgcgt tgctggcgtt tttccatagg ctccgccccc ctgacgagca tcacaaaaat   3600
cgacgctcaa gtcagaggtg gcgaaacccg acaggactat aaagatacca ggcgtttccc   3660
cctggaagct ccctcgtgcg ctctcctgtt ccgaccctgc cgcttaccgg atacctgtcc   3720
gcctttctcc cttcgggaag cgtggcgctt tctcatagct cacgctgtag gtatctcagt   3780
```

```
tcggtgtagg tcgttcgctc caagctgggc tgtgtgcacg aacccccgt tcagcccgac   3840

cgctgcgcct tatccggtaa ctatcgtctt gagtccaacc cggtaagaca cgacttatcg   3900

ccactggcag cagccactgg taacaggatt agcagagcga ggtatgtagg cggtgctaca   3960

gagttcttga agtggtggcc taactacggc tacactagaa gaacagtatt tggtatctgc   4020

gctctgctga agccagttac cttcggaaaa agagttggta gctcttgatc cggcaaacaa   4080

accaccgctg gtagcggtgg tttttttgtt tgcaagcagc agattacgcg cagaaaaaaa   4140

ggatctcaag aagatccttt gatcttttct acggggtctg acgctcagtg gaacgaaaac   4200

tcacgttaag ggattttggt catgagatta tcaaaaagga tcttcaccta gatcctttta   4260

aattaaaaat gaagttttaa atcaatctaa agtatatatg agtaaacttg gtctgacagt   4320

taccaatgct taatcagtga ggcacctatc tcagcgatct gtctatttcg ttcatccata   4380

gttgcctgac tccccgtcgt gtagataact acgatacggg agggcttacc atctggcccc   4440

agtgctgcaa tgataccgcg agacccacgc tcaccggctc cagatttatc agcaataaac   4500

cagccagccg gaagggccga gcgcagaagt ggtcctgcaa ctttatccgc ctccatccag   4560

tctattaatt gttgccggga agctagagta agtagttcgc cagttaatag tttgcgcaac   4620

gttgttgcca ttgctacagg catcgtggtg tcacgctcgt cgtttggtat ggcttcattc   4680

agctccggtt cccaacgatc aaggcgagtt acatgatccc ccatgttgtg caaaaaagcg   4740

gttagctcct tcggtcctcc gatcgttgtc agaagtaagt tggccgcagt gttatcactc   4800

atggttatgg cagcactgca taattctctt actgtcatgc catccgtaag atgcttttct   4860

gtgactggtg agtactcaac caagtcattc tgagaatagt gtatgcggcg accgagttgc   4920

tcttgcccgg cgtcaatacg ggataatacc gcgccacata gcagaacttt aaaagtgctc   4980

atcattggaa aacgttcttc ggggcgaaaa ctctcaagga tcttaccgct gttgagatcc   5040

agttcgatgt aacccactcg tgcacccaac tgatcttcag catcttttac tttcaccagc   5100

gtttctgggt gagcaaaaac aggaaggcaa aatgccgcaa aaaagggaat aagggcgaca   5160

cggaaatgtt gaatactcat actcttcctt tttcaatatt attgaagcat ttatcagggt   5220

tattgtctca tgagcggata catatttgaa tgtatttaga aaaataaaca aataggggtt   5280

ccgcgcacat ttccccgaaa agtgccac                                      5308


<210> SEQ ID NO 43
<211> LENGTH: 5291
<212> TYPE: DNA
<213> ORGANISM: Artificial
<220> FEATURE:
<223> OTHER INFORMATION: Plasmid pGSH0_mir451shRNA_Tyr2A

<400> SEQUENCE: 43

ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480
```

-continued

```
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgtagggat aacagggtaa tgcgcgcgta atacgactca    660
ctatagggcg aattgggtac cgggcccccc ctcgaccata gccaattcaa tatggcgtat    720
atggactcat gccaattcaa tatggtggat ctggacctgt gccaattcaa tatggcgtat    780
atggactcgt gccaattcaa tatggtggat ctggacccca gccaattcaa tatggcggac    840
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgcgcacttg ggaatggcaa ggttagtata caaatttgtt cacgaacaaa tttgtatact   2280
actcttgcta tacccagaaa aatgcatctt cacgcgtagc ttcccttaat acaagtgaga   2340
tgatggcata ccatctttcg ggactgagtt gatgtgaaga gtttttctgt tttgctgatc   2400
acttgtatat tatgtgacta atagttaaag tgccaaaata aaatgtggga acattgaatg   2460
tgtatcctac ttaagggaat cgatttcaag gaggacggaa acatcctcgg ccacaagttg   2520
gaatacaact acaactccca caacgtatac atcatggccg acaagcaaaa gaacggcatc   2580
aaagccaact tcaagacccg ccacaacatc gaagacggcg gcgtgcaact cgctgatcat   2640
tatcaacaaa atactccaat tggcgatgac cctgtccttt taccagacaa ccattacctg   2700
tccacacaat ctgccctttc gaaagatccc aacgaaaaga gagaccacat ggtccttctt   2760
gagtttgtaa cggctgctgg gattacacat ggcatggatg aactatacaa aaatctagaa   2820
ctatagtgag tcgtattacg tagatccaga catgataaga tacattgatg agtttggaca   2880
```

-continued

```
aaccacaact agaatgcagt gaaaaaaatg ctttatttgt gaaatttgtg atgctattgc   2940
tttatttgta accattataa gctgcaataa acaagttaac aacaacaatt gcattcattt   3000
tatgtttcag gttcaggggg aggtgtggga ggttttttaa ttcgcggccg ccaccgcggt   3060
ggagctccag cttttgttcc ctttagtgag ggttaattgc gcgcattacc ctgttatccc   3120
tacgcgcttg gcgtaatcat ggtcatagct gtttcctgtg tgaaattgtt atccgctcac   3180
aattccacac aacatacgag ccggaagcat aaagtgtaaa gcctggggtg cctaatgagt   3240
gagctaactc acattaattg cgttgcgctc actgcccgct ttccagtcgg gaaacctgtc   3300
gtgccagctg cattaatgaa tcggccaacg cgcggggaga ggcggtttgc gtattgggcg   3360
ctcttccgct tcctcgctca ctgactcgct gcgctcggtc gttcggctgc ggcgagcggt   3420
atcagctcac tcaaaggcgg taatacggtt atccacagaa tcaggggata acgcaggaaa   3480
gaacatgtga gcaaaaggcc agcaaaaggc caggaaccgt aaaaaggccg cgttgctggc   3540
gtttttccat aggctccgcc cccctgacga gcatcacaaa aatcgacgct caagtcagag   3600
gtggcgaaac ccgacaggac tataaagata ccaggcgttt ccccctggaa gctccctcgt   3660
gcgctctcct gttccgaccc tgccgcttac cggatacctg tccgcctttc tcccttcggg   3720
aagcgtggcg ctttctcata gctcacgctg taggtatctc agttcggtgt aggtcgttcg   3780
ctccaagctg ggctgtgtgc acgaaccccc cgttcagccc gaccgctgcg ccttatccgg   3840
taactatcgt cttgagtcca acccggtaag acacgactta tcgccactgg cagcagccac   3900
tggtaacagg attagcagag cgaggtatgt aggcggtgct acagagttct tgaagtggtg   3960
gcctaactac ggctacacta gaagaacagt atttggtatc tgcgctctgc tgaagccagt   4020
taccttcgga aaaagagttg gtagctcttg atccggcaaa caaaccaccg ctggtagcgg   4080
tggttttttt gtttgcaagc agcagattac gcgcagaaaa aaaggatctc aagaagatcc   4140
tttgatcttt tctacggggt ctgacgctca gtggaacgaa aactcacgtt aagggatttt   4200
ggtcatgaga ttatcaaaaa ggatcttcac ctagatcctt ttaaattaaa aatgaagttt   4260
taaatcaatc taaagtatat atgagtaaac ttggtctgac agttaccaat gcttaatcag   4320
tgaggcacct atctcagcga tctgtctatt tcgttcatcc atagttgcct gactccccgt   4380
cgtgtagata actacgatac gggagggctt accatctggc cccagtgctg caatgatacc   4440
gcgagaccca cgctcaccgg ctccagattt atcagcaata aaccagccag ccggaagggc   4500
cgagcgcaga agtggtcctg caactttatc cgcctccatc cagtctatta attgttgccg   4560
ggaagctaga gtaagtagtt cgccagttaa tagtttgcgc aacgttgttg ccattgctac   4620
aggcatcgtg gtgtcacgct cgtcgtttgg tatggcttca ttcagctccg gttcccaacg   4680
atcaaggcga gttacatgat cccccatgtt gtgcaaaaaa gcggttagct ccttcggtcc   4740
tccgatcgtt gtcagaagta agttggccgc agtgttatca ctcatggtta tggcagcact   4800
gcataattct cttactgtca tgccatccgt aagatgcttt tctgtgactg gtgagtactc   4860
aaccaagtca ttctgagaat agtgtatgcg gcgaccgagt tgctcttgcc cggcgtcaat   4920
acgggataat accgcgccac atagcagaac tttaaaagtg ctcatcattg gaaaacgttc   4980
ttcggggcga aaactctcaa ggatcttacc gctgttgaga tccagttcga tgtaacccac   5040
tcgtgcaccc aactgatctt cagcatcttt tactttcacc agcgtttctg ggtgagcaaa   5100
aacaggaagg caaaatgccg caaaaaaggg aataagggcg acacggaaat gttgaatact   5160
catactcttc ctttttcaat attattgaag catttatcag ggttattgtc tcatgagcgg   5220
```

atacatattt gaatgtattt agaaaaataa acaaataggg gttccgcgca catttccccg 5280
aaaagtgcca c 5291

<210> SEQ ID NO 44
<211> LENGTH: 5291
<212> TYPE: DNA
<213> ORGANISM: Artificial
<220> FEATURE:
<223> OTHER INFORMATION: Plasmid pGSH0_mir451shRNA_Tyr6C

<400> SEQUENCE: 44
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgtagggat aacagggtaa tgcgcgcgta atacgactca 660
ctatagggcg aattgggtac cgggcccccc ctcgaccata gccaattcaa tatggcgtat 720
atggactcat gccaattcaa tatggtggat ctggacctgt gccaattcaa tatggcgtat 780
atggactcgt gccaattcaa tatggtggat ctggacccca gccaattcaa tatggcggac 840
ttggcaccat gccaattcaa tatggcggac ttggcactgt gccaactggg gaggggtcta 900
cttggcacgg tgccaagttt gaggaggggt cttggccctg tgccaagtcc gccatattga 960
attggcatgg tgccaataat ggcggccata ttggctatat gccaggatca atatataggc 1020
aatatccaat atggccctat gccaatatgg ctattggcca ggttcaatac tatgtattgg 1080
ccctatgcca tatagtattc catatatggg ttttcctatt gacgtagata gcccctccca 1140
atgggcggtc ccatatacca tatatggggc ttcctaatac cgcccatagc cactccccca 1200
ttgacgtcaa tggtctctat atatggtctt tcctattgac gtcatatggg cggtcctatt 1260
gacgtatatg gcgcctcccc cattgacgtc aattacggta aatggcccgc ctggctcaat 1320
gcccattgac gtcaatagga ccacccacca ttgacgtcaa tgggatggct cattgcccat 1380
tcatatccgt tctcacgccc cctattgacg tcaatgacgg taaatggccc acttggcagt 1440
acatcaatat ctattaatag taacttggca agtacattac tattggaagt acgccagggt 1500
acattggcag tactcccatt gacgtcaatg gcggtaaatg gcccgcgatg gctgccaagt 1560
acatccccat tgacgtcaat ggggaggggc aatgacgcaa atgggcgttc cattgacgta 1620
aatgggcggt aggcgtgcct aatgggaggt ctatataagc aatgctcgtt tagggaaccg 1680
ccattctgcc tggggacgtc ggagcaagct agcttgcttg ttctttttgc agaagctcag 1740
aataaacgct caactttggc agatctgaat tcctgcagcc cgggggatcc acagccacca 1800
tgagtaaagg agaagaactt ttcactggag ttgtcccaat tcttgttgaa ttagatggtg 1860
atgttaatgg gtacaaattt tctgtcagtg gagagggtga aggtgatgca acatacggaa 1920
aacttaccct taaatttatt tgcactactg gaaaactacc tgttccatgg ccaacacttg 1980

-continued

```
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgcgcacttg ggaatggcaa ggttgggaaa gtcccagtgg gccgccactg ggactttccc   2280
actcttgcta tacccagaaa aatgcatctt cacgcgtagc ttcccttaat acaagtgaga   2340
tgatggcata ccatctttcg ggactgagtt gatgtgaaga gtttttctgt tttgctgatc   2400
acttgtatat tatgtgacta atagttaaag tgccaaaata aaatgtggga acattgaatg   2460
tgtatcctac ttaagggaat cgatttcaag gaggacggaa acatcctcgg ccacaagttg   2520
gaatacaact acaactccca caacgtatac atcatggccg acaagcaaaa gaacggcatc   2580
aaagccaact tcaagacccg ccacaacatc gaagacggcg gcgtgcaact cgctgatcat   2640
tatcaacaaa atactccaat tggcgatgac cctgtccttt taccagacaa ccattacctg   2700
tccacacaat ctgccctttc gaaagatccc aacgaaaaga gagaccacat ggtccttctt   2760
gagtttgtaa cggctgctgg gattacacat ggcatggatg aactatacaa aaatctagaa   2820
ctatagtgag tcgtattacg tagatccaga catgataaga tacattgatg agtttggaca   2880
aaccacaact agaatgcagt gaaaaaaatg ctttatttgt gaaatttgtg atgctattgc   2940
tttatttgta accattataa gctgcaataa acaagttaac aacaacaatt gcattcattt   3000
tatgtttcag gttcaggggg aggtgtggga ggttttttaa ttcgcggccg ccaccgcggt   3060
ggagctccag cttttgttcc ctttagtgag ggttaattgc gcgcattacc ctgttatccc   3120
tacgcgcttg gcgtaatcat ggtcatagct gtttcctgtg tgaaattgtt atccgctcac   3180
aattccacac aacatacgag ccggaagcat aaagtgtaaa gcctggggtg cctaatgagt   3240
gagctaactc acattaattg cgttgcgctc actgcccgct ttccagtcgg gaaacctgtc   3300
gtgccagctg cattaatgaa tcggccaacg cgcggggaga ggcggtttgc gtattgggcg   3360
ctcttccgct tcctcgctca ctgactcgct gcgctcggtc gttcggctgc ggcgagcggt   3420
atcagctcac tcaaaggcgg taatacggtt atccacagaa tcaggggata acgcaggaaa   3480
gaacatgtga gcaaaaggcc agcaaaaggc caggaaccgt aaaaaggccg cgttgctggc   3540
gtttttccat aggctccgcc cccctgacga gcatcacaaa aatcgacgct caagtcagag   3600
gtggcgaaac ccgacaggac tataaagata ccaggcgttt ccccctggaa gctccctcgt   3660
gcgctctcct gttccgaccc tgccgcttac cggatacctg tccgcctttc tcccttcggg   3720
aagcgtggcg ctttctcata gctcacgctg taggtatctc agttcggtgt aggtcgttcg   3780
ctccaagctg ggctgtgtgc acgaaccccc cgttcagccc gaccgctgcg ccttatccgg   3840
taactatcgt cttgagtcca acccggtaag acacgactta tcgccactgg cagcagccac   3900
tggtaacagg attagcagag cgaggtatgt aggcggtgct acagagttct tgaagtggtg   3960
gcctaactac ggctacacta gaagaacagt atttggtatc tgcgctctgc tgaagccagt   4020
taccttcgga aaaagagttg gtagctcttg atccggcaaa caaaccaccg ctggtagcgg   4080
tggttttttt gtttgcaagc agcagattac gcgcagaaaa aaaggatctc aagaagatcc   4140
tttgatcttt tctacggggt ctgacgctca gtggaacgaa aactcacgtt aagggatttt   4200
ggtcatgaga ttatcaaaaa ggatcttcac ctagatcctt ttaaattaaa aatgaagttt   4260
taaatcaatc taaagtatat atgagtaaac ttggtctgac agttaccaat gcttaatcag   4320
```

```
tgaggcacct atctcagcga tctgtctatt tcgttcatcc atagttgcct gactccccgt   4380

cgtgtagata actacgatac gggagggctt accatctggc cccagtgctg caatgatacc   4440

gcgagaccca cgctcaccgg ctccagattt atcagcaata aaccagccag ccggaagggc   4500

cgagcgcaga agtggtcctg caactttatc cgcctccatc cagtctatta attgttgccg   4560

ggaagctaga gtaagtagtt cgccagttaa tagtttgcgc aacgttgttg ccattgctac   4620

aggcatcgtg gtgtcacgct cgtcgtttgg tatggcttca ttcagctccg gttcccaacg   4680

atcaaggcga gttacatgat cccccatgtt gtgcaaaaaa gcggttagct ccttcggtcc   4740

tccgatcgtt gtcagaagta agttggccgc agtgttatca ctcatggtta tggcagcact   4800

gcataattct cttactgtca tgccatccgt aagatgcttt tctgtgactg gtgagtactc   4860

aaccaagtca ttctgagaat agtgtatgcg gcgaccgagt tgctcttgcc cggcgtcaat   4920

acgggataat accgcgccac atagcagaac tttaaaagtg ctcatcattg gaaaacgttc   4980

ttcggggcga aaactctcaa ggatcttacc gctgttgaga tccagttcga tgtaacccac   5040

tcgtgcaccc aactgatctt cagcatcttt tactttcacc agcgtttctg ggtgagcaaa   5100

aacaggaagg caaaatgccg caaaaaaggg aataagggcg acacggaaat gttgaatact   5160

catactcttc ctttttcaat attattgaag catttatcag ggttattgtc tcatgagcgg   5220

atacatattt gaatgtattt agaaaaataa acaaataggg gttccgcgca catttccccg   5280

aaaagtgcca c                                                        5291


<210> SEQ ID NO 45
<211> LENGTH: 5306
<212> TYPE: DNA
<213> ORGANISM: Artificial
<220> FEATURE:
<223> OTHER INFORMATION: Plasmid pGSH0_2ndGenshRNA_Tyr2A

<400> SEQUENCE: 45

ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgtagggat aacagggtaa tgcgcgcgta atacgactca    660

ctatagggcg aattgggtac cgggcccccc ctcgaccata gccaattcaa tatggcgtat    720

atggactcat gccaattcaa tatggtggat ctggacctgt gccaattcaa tatggcgtat    780

atggactcgt gccaattcaa tatggtggat ctggacccca gccaattcaa tatggcggac    840

ttggcaccat gccaattcaa tatggcggac ttggcactgt gccaactggg gaggggtcta    900

cttggcacgg tgccaagttt gaggaggggt cttggccctg tgccaagtcc gccatattga    960

attggcatgg tgccaataat ggcggccata ttggctatat gccaggatca atatataggc   1020

aatatccaat atggccctat gccaatatgg ctattggcca ggttcaatac tatgtattgg   1080
```

-continued

```
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtgagcgcc gtgaacaaat ttgtatacta atagtgaagc cacagatgta   2280
ttagtataca aatttgttca cgttgcctac tgccttatgc atcttcacgc gtagcttccc   2340
ttaatacaag tgagatgatg gcataccatc tttcgggact gagttgatgt gaagagtttt   2400
tctgttttgc tgatcacttg tatattatgt gactaatagt taaagtgcca aaataaaatg   2460
tgggaacatt gaatgtgtat cctacttaag ggaatcgatt tcaaggagga cggaaacatc   2520
ctcggccaca agttggaata caactacaac tcccacaacg tatacatcat ggccgacaag   2580
caaaagaacg gcatcaaagc caacttcaag acccgccaca acatcgaaga cggcggcgtg   2640
caactcgctg atcattatca acaaaatact ccaattggcg atgaccctgt ccttttacca   2700
gacaaccatt acctgtccac acaatctgcc ctttcgaaag atcccaacga aaagagagac   2760
cacatggtcc ttcttgagtt tgtaacggct gctgggatta cacatggcat ggatgaacta   2820
tacaaaaatc tagaactata gtgagtcgta ttacgtagat ccagacatga taagatacat   2880
tgatgagttt ggacaaacca caactagaat gcagtgaaaa aaatgcttta tttgtgaaat   2940
ttgtgatgct attgctttat ttgtaaccat tataagctgc aataaacaag ttaacaacaa   3000
caattgcatt cattttatgt ttcaggttca gggggaggtg tgggaggttt tttaattcgc   3060
ggccgccacc gcggtggagc tccagctttt gttcccttta gtgagggtta attgcgcgca   3120
ttaccctgtt atccctacgc gcttggcgta atcatggtca tagctgtttc ctgtgtgaaa   3180
ttgttatccg ctcacaattc cacacaacat acgagccgga agcataaagt gtaaagcctg   3240
gggtgcctaa tgagtgagct aactcacatt aattgcgttg cgctcactgc ccgctttcca   3300
gtcgggaaac ctgtcgtgcc agctgcatta atgaatcggc caacgcgcgg ggagaggcgg   3360
tttgcgtatt gggcgctctt ccgcttcctc gctcactgac tcgctgcgct cggtcgttcg   3420
```

gctgcggcga gcggtatcag ctcactcaaa ggcggtaata cggttatcca cagaatcagg 3480
ggataacgca ggaaagaaca tgtgagcaaa aggccagcaa aaggccagga accgtaaaaa 3540
ggccgcgttg ctggcgtttt tccataggct ccgcccccct gacgagcatc acaaaaatcg 3600
acgctcaagt cagaggtggc gaaacccgac aggactataa agataccagg cgtttccccc 3660
tggaagctcc ctcgtgcgct ctcctgttcc gaccctgccg cttaccggat acctgtccgc 3720
ctttctccct tcgggaagcg tggcgctttc tcatagctca cgctgtaggt atctcagttc 3780
ggtgtaggtc gttcgctcca agctgggctg tgtgcacgaa ccccccgttc agcccgaccg 3840
ctgcgcctta tccggtaact atcgtcttga gtccaacccg gtaagacacg acttatcgcc 3900
actggcagca gccactggta acaggattag cagagcgagg tatgtaggcg gtgctacaga 3960
gttcttgaag tggtggccta actacggcta cactagaaga acagtatttg gtatctgcgc 4020
tctgctgaag ccagttacct tcggaaaaag agttggtagc tcttgatccg gcaaacaaac 4080
caccgctggt agcggtggtt tttttgtttg caagcagcag attacgcgca gaaaaaaagg 4140
atctcaagaa gatcctttga tcttttctac ggggtctgac gctcagtgga acgaaaactc 4200
acgttaaggg attttggtca tgagattatc aaaaaggatc ttcacctaga tccttttaaa 4260
ttaaaaatga agttttaaat caatctaaag tatatatgag taaacttggt ctgacagtta 4320
ccaatgctta atcagtgagg cacctatctc agcgatctgt ctatttcgtt catccatagt 4380
tgcctgactc cccgtcgtgt agataactac gatacgggag ggcttaccat ctggccccag 4440
tgctgcaatg ataccgcgag acccacgctc accggctcca gatttatcag caataaacca 4500
gccagccgga agggccgagc gcagaagtgg tcctgcaact ttatccgcct ccatccagtc 4560
tattaattgt tgccgggaag ctagagtaag tagttcgcca gttaatagtt tgcgcaacgt 4620
tgttgccatt gctacaggca tcgtggtgtc acgctcgtcg tttggtatgg cttcattcag 4680
ctccggttcc caacgatcaa ggcgagttac atgatccccc atgttgtgca aaaaagcggt 4740
tagctccttc ggtcctccga tcgttgtcag aagtaagttg gccgcagtgt tatcactcat 4800
ggttatggca gcactgcata attctcttac tgtcatgcca tccgtaagat gcttttctgt 4860
gactggtgag tactcaacca agtcattctg agaatagtgt atgcggcgac cgagttgctc 4920
ttgcccggcg tcaatacggg ataataccgc gccacatagc agaactttaa aagtgctcat 4980
cattggaaaa cgttcttcgg ggcgaaaact ctcaaggatc ttaccgctgt tgagatccag 5040
ttcgatgtaa cccactcgtg cacccaactg atcttcagca tcttttactt tcaccagcgt 5100
ttctgggtga gcaaaaacag gaaggcaaaa tgccgcaaaa aagggaataa gggcgacacg 5160
gaaatgttga atactcatac tcttcctttt tcaatattat tgaagcattt atcagggtta 5220
ttgtctcatg agcggataca tatttgaatg tatttagaaa aataaacaaa taggggttcc 5280
gcgcacattt ccccgaaaag tgccac 5306

<210> SEQ ID NO 46
<211> LENGTH: 5306
<212> TYPE: DNA
<213> ORGANISM: Artificial
<220> FEATURE:
<223> OTHER INFORMATION: Plasmid pGSH0_2ndGenshRNA_Tyr6C

<400> SEQUENCE: 46
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180

-continued

```
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgtagggat aacagggtaa tgcgcgcgta atacgactca    660
ctatagggcg aattgggtac cgggcccccc ctcgaccata gccaattcaa tatggcgtat    720
atggactcat gccaattcaa tatggtggat ctggacctgt gccaattcaa tatggcgtat    780
atggactcgt gccaattcaa tatggtggat ctggacccca gccaattcaa tatggcggac    840
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgctgctgac agtgagcgcc ggcccactgg gactttccca atagtgaagc cacagatgta   2280
ttgggaaagt cccagtgggc cgttgcctac tgccttatgc atcttcacgc gtagcttccc   2340
ttaatacaag tgagatgatg gcataccatc tttcgggact gagttgatgt gaagagtttt   2400
tctgttttgc tgatcacttg tatattatgt gactaatagt taaagtgcca aaataaaatg   2460
tgggaacatt gaatgtgtat cctacttaag ggaatcgatt tcaaggagga cggaaacatc   2520
```

-continued

```
ctcggccaca agttggaata caactacaac tcccacaacg tatacatcat ggccgacaag   2580
caaaagaacg gcatcaaagc caacttcaag acccgccaca acatcgaaga cggcggcgtg   2640
caactcgctg atcattatca acaaaatact ccaattggcg atgaccctgt ccttttacca   2700
gacaaccatt acctgtccac acaatctgcc ctttcgaaag atcccaacga aaagagagac   2760
cacatggtcc ttcttgagtt tgtaacggct gctgggatta cacatggcat ggatgaacta   2820
tacaaaaatc tagaactata gtgagtcgta ttacgtagat ccagacatga taagatacat   2880
tgatgagttt ggacaaacca caactagaat gcagtgaaaa aaatgcttta tttgtgaaat   2940
ttgtgatgct attgctttat ttgtaaccat tataagctgc aataaacaag ttaacaacaa   3000
caattgcatt cattttatgt ttcaggttca gggggaggtg tgggaggttt tttaattcgc   3060
ggccgccacc gcggtggagc tccagctttt gttcccttta gtgagggtta attgcgcgca   3120
ttaccctgtt atccctacgc gcttggcgta atcatggtca tagctgtttc ctgtgtgaaa   3180
ttgttatccg ctcacaattc cacacaacat acgagccgga agcataaagt gtaaagcctg   3240
gggtgcctaa tgagtgagct aactcacatt aattgcgttg cgctcactgc ccgctttcca   3300
gtcgggaaac ctgtcgtgcc agctgcatta atgaatcggc caacgcgcgg ggagaggcgg   3360
tttgcgtatt gggcgctctt ccgcttcctc gctcactgac tcgctgcgct cggtcgttcg   3420
gctgcggcga gcggtatcag ctcactcaaa ggcggtaata cggttatcca cagaatcagg   3480
ggataacgca ggaaagaaca tgtgagcaaa aggccagcaa aaggccagga accgtaaaaa   3540
ggccgcgttg ctggcgtttt tccataggct ccgcccccct gacgagcatc acaaaaatcg   3600
acgctcaagt cagaggtggc gaaacccgac aggactataa agataccagg cgtttccccc   3660
tggaagctcc ctcgtgcgct ctcctgttcc gaccctgccg cttaccggat acctgtccgc   3720
ctttctccct tcgggaagcg tggcgctttc tcatagctca cgctgtaggt atctcagttc   3780
ggtgtaggtc gttcgctcca agctgggctg tgtgcacgaa ccccccgttc agcccgaccg   3840
ctgcgcctta tccggtaact atcgtcttga gtccaacccg gtaagacacg acttatcgcc   3900
actggcagca gccactggta acaggattag cagagcgagg tatgtaggcg gtgctacaga   3960
gttcttgaag tggtggccta actacggcta cactagaaga acagtatttg gtatctgcgc   4020
tctgctgaag ccagttacct tcggaaaaag agttggtagc tcttgatccg gcaaacaaac   4080
caccgctggt agcggtggtt tttttgtttg caagcagcag attacgcgca gaaaaaaagg   4140
atctcaagaa gatcctttga tcttttctac ggggtctgac gctcagtgga acgaaaactc   4200
acgttaaggg attttggtca tgagattatc aaaaaggatc ttcacctaga tccttttaaa   4260
ttaaaaatga agttttaaat caatctaaag tatatatgag taaacttggt ctgacagtta   4320
ccaatgctta atcagtgagg cacctatctc agcgatctgt ctatttcgtt catccatagt   4380
tgcctgactc cccgtcgtgt agataactac gatacgggag ggcttaccat ctggccccag   4440
tgctgcaatg ataccgcgag acccacgctc accggctcca gatttatcag caataaacca   4500
gccagccgga agggccgagc gcagaagtgg tcctgcaact ttatccgcct ccatccagtc   4560
tattaattgt tgccgggaag ctagagtaag tagttcgcca gttaatagtt tgcgcaacgt   4620
tgttgccatt gctacaggca tcgtggtgtc acgctcgtcg tttggtatgg cttcattcag   4680
ctccggttcc caacgatcaa ggcgagttac atgatccccc atgttgtgca aaaaagcggt   4740
tagctccttc ggtcctccga tcgttgtcag aagtaagttg gccgcagtgt tatcactcat   4800
ggttatggca gcactgcata attctcttac tgtcatgcca tccgtaagat gcttttctgt   4860
gactggtgag tactcaacca agtcattctg agaatagtgt atgcggcgac cgagttgctc   4920
```

ttgcccggcg tcaatacggg ataataccgc gccacatagc agaactttaa aagtgctcat 4980
cattggaaaa cgttcttcgg ggcgaaaact ctcaaggatc ttaccgctgt tgagatccag 5040
ttcgatgtaa cccactcgtg cacccaactg atcttcagca tcttttactt tcaccagcgt 5100
ttctgggtga gcaaaaacag gaaggcaaaa tgccgcaaaa aagggaataa gggcgacacg 5160
gaaatgttga atactcatac tcttcctttt tcaatattat tgaagcattt atcagggtta 5220
ttgtctcatg agcggataca tatttgaatg tatttagaaa aataaacaaa taggggttcc 5280
gcgcacattt ccccgaaaag tgccac 5306

<210> SEQ ID NO 47
<211> LENGTH: 5316
<212> TYPE: DNA
<213> ORGANISM: Artificial
<220> FEATURE:
<223> OTHER INFORMATION: Plasmid GSH0_Nek2 OshR1

<400> SEQUENCE: 47
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgtagggat aacagggtaa tgcgcgcgta atacgactca 660
ctatagggcg aattgggtac cgggcccccc ctcgaccata gccaattcaa tatggcgtat 720
atggactcat gccaattcaa tatggtggat ctggacctgt gccaattcaa tatggcgtat 780
atggactcgt gccaattcaa tatggtggat ctggacccca gccaattcaa tatggcggac 840
ttggcaccat gccaattcaa tatggcggac ttggcactgt gccaactggg gaggggtcta 900
cttggcacgg tgccaagttt gaggaggggt cttggccctg tgccaagtcc gccatattga 960
attggcatgg tgccaataat ggcggccata ttggctatat gccaggatca atatataggc 1020
aatatccaat atggccctat gccaatatgg ctattggcca ggttcaatac tatgtattgg 1080
ccctatgcca tatagtattc catatatggg ttttcctatt gacgtagata gcccctccca 1140
atgggcggtc ccatatacca tatatggggc ttcctaatac cgcccatagc cactccccca 1200
ttgacgtcaa tggtctctat atatggtctt tcctattgac gtcatatggg cggtcctatt 1260
gacgtatatg gcgcctcccc cattgacgtc aattacggta aatggcccgc ctggctcaat 1320
gcccattgac gtcaatagga ccacccacca ttgacgtcaa tgggatggct cattgcccat 1380
tcatatccgt tctcacgccc cctattgacg tcaatgacgg taaatggccc acttggcagt 1440
acatcaatat ctattaatag taacttggca agtacattac tattggaagt acgccagggt 1500
acattggcag tactcccatt gacgtcaatg gcggtaaatg gcccgcgatg gctgccaagt 1560
acatccccat tgacgtcaat ggggaggggc aatgacgcaa atgggcgttc cattgacgta 1620

-continued

```
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cggggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgccttcgtc gaccgttgac agtgagcgac ttcttccact gaaggtcgat ggccgtgaag   2280
ccacaaatgg gccatcgacc tagtggatga agctgcctac tgcctaatgc atcttcacgc   2340
gtagcttccc ttaatacaag tgagatgatg gcataccatc tttcgggact gagttgatgt   2400
gaagagtttt tctgttttgc tgatcacttg tatattatgt gactaatagt taaagtgcca   2460
aaataaaatg tgggaacatt gaatgtgtat cctacttaag ggaatcgatt tcaaggagga   2520
cggaaacatc ctcggccaca agttggaata caactacaac tcccacaacg tatacatcat   2580
ggccgacaag caaaagaacg gcatcaaagc caacttcaag acccgccaca acatcgaaga   2640
cggcggcgtg caactcgctg atcattatca acaaaatact ccaattggcg atgaccctgt   2700
ccttttacca gacaaccatt acctgtccac acaatctgcc ctttcgaaag atcccaacga   2760
aaagagagac cacatggtcc ttcttgagtt tgtaacggct gctgggatta cacatggcat   2820
ggatgaacta tacaaaaatc tagaactata gtgagtcgta ttacgtagat ccagacatga   2880
taagatacat tgatgagttt ggacaaacca caactagaat gcagtgaaaa aaatgcttta   2940
tttgtgaaat ttgtgatgct attgctttat ttgtaaccat tataagctgc aataaacaag   3000
ttaacaacaa caattgcatt cattttatgt ttcaggttca gggggaggtg tgggaggttt   3060
tttaattcgc ggccgccacc gcggtggagc tccagctttt gttcccttta gtgagggtta   3120
attgcgcgca ttaccctgtt atccctacgc gcttggcgta atcatggtca tagctgtttc   3180
ctgtgtgaaa ttgttatccg ctcacaattc cacacaacat acgagccgga agcataaagt   3240
gtaaagcctg gggtgcctaa tgagtgagct aactcacatt aattgcgttg cgctcactgc   3300
ccgctttcca gtcgggaaac ctgtcgtgcc agctgcatta atgaatcggc caacgcgcgg   3360
ggagaggcgg tttgcgtatt gggcgctctt ccgcttcctc gctcactgac tcgctgcgct   3420
cggtcgttcg gctgcggcga gcggtatcag ctcactcaaa ggcggtaata cggttatcca   3480
cagaatcagg ggataacgca ggaaagaaca tgtgagcaaa aggccagcaa aaggccagga   3540
accgtaaaaa ggccgcgttg ctggcgtttt tccataggct ccgcccccct gacgagcatc   3600
acaaaaatcg acgctcaagt cagaggtggc gaaacccgac aggactataa agataccagg   3660
cgtttccccc tggaagctcc ctcgtgcgct ctcctgttcc gaccctgccg cttaccggat   3720
acctgtccgc ctttctccct tcgggaagcg tggcgctttc tcatagctca cgctgtaggt   3780
atctcagttc ggtgtaggtc gttcgctcca agctgggctg tgtgcacgaa ccccccgttc   3840
agcccgaccg ctgcgcctta tccggtaact atcgtcttga gtccaacccg gtaagacacg   3900
acttatcgcc actggcagca gccactggta acaggattag cagagcgagg tatgtaggcg   3960
gtgctacaga gttcttgaag tggtggccta actacggcta cactagaaga acagtatttg   4020
```

gtatctgcgc tctgctgaag ccagttacct tcggaaaaag agttggtagc tcttgatccg 4080
gcaaacaaac caccgctggt agcggtggtt tttttgtttg caagcagcag attacgcgca 4140
gaaaaaaagg atctcaagaa gatcctttga tcttttctac ggggtctgac gctcagtgga 4200
acgaaaactc acgttaaggg attttggtca tgagattatc aaaaaggatc ttcacctaga 4260
tccttttaaa ttaaaaatga agttttaaat caatctaaag tatatatgag taaacttggt 4320
ctgacagtta ccaatgctta atcagtgagg cacctatctc agcgatctgt ctatttcgtt 4380
catccatagt tgcctgactc cccgtcgtgt agataactac gatacgggag ggcttaccat 4440
ctggccccag tgctgcaatg ataccgcgag acccacgctc accggctcca gatttatcag 4500
caataaacca gccagccgga agggccgagc gcagaagtgg tcctgcaact ttatccgcct 4560
ccatccagtc tattaattgt tgccgggaag ctagagtaag tagttcgcca gttaatagtt 4620
tgcgcaacgt tgttgccatt gctacaggca tcgtggtgtc acgctcgtcg tttggtatgg 4680
cttcattcag ctccggttcc caacgatcaa ggcgagttac atgatccccc atgttgtgca 4740
aaaaagcggt tagctccttc ggtcctccga tcgttgtcag aagtaagttg gccgcagtgt 4800
tatcactcat ggttatggca gcactgcata attctcttac tgtcatgcca tccgtaagat 4860
gcttttctgt gactggtgag tactcaacca agtcattctg agaatagtgt atgcggcgac 4920
cgagttgctc ttgcccggcg tcaatacggg ataataccgc gccacatagc agaactttaa 4980
aagtgctcat cattggaaaa cgttcttcgg ggcgaaaact ctcaaggatc ttaccgctgt 5040
tgagatccag ttcgatgtaa cccactcgtg cacccaactg atcttcagca tcttttactt 5100
tcaccagcgt ttctgggtga gcaaaaacag gaaggcaaaa tgccgcaaaa aagggaataa 5160
gggcgacacg gaaatgttga atactcatac tcttcctttt tcaatattat tgaagcattt 5220
atcagggtta ttgtctcatg agcggataca tatttgaatg tatttagaaa aataaacaaa 5280
taggggttcc gcgcacattt ccccgaaaag tgccac 5316

<210> SEQ ID NO 48
<211> LENGTH: 5316
<212> TYPE: DNA
<213> ORGANISM: Artificial
<220> FEATURE:
<223> OTHER INFORMATION: Plasmid GSH0_Nek2 OshR2

<400> SEQUENCE: 48
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgtagggat aacagggtaa tgcgcgcgta atacgactca 660
ctatagggcg aattgggtac cgggcccccc ctcgaccata gccaattcaa tatggcgtat 720

-continued

```
atggactcat gccaattcaa tatggtggat ctggacctgt gccaattcaa tatggcgtat    780
atggactcgt gccaattcaa tatggtggat ctggacccca gccaattcaa tatggcggac    840
ttggcaccat gccaattcaa tatggcggac ttggcactgt gccaactggg gaggggtcta    900
cttggcacgg tgccaagttt gaggaggggt cttggccctg tgccaagtcc gccatattga    960
attggcatgg tgccaataat ggcggccata ttggctatat gccaggatca atatataggc   1020
aatatccaat atggccctat gccaatatgg ctattggcca ggttcaatac tatgtattgg   1080
ccctatgcca tatagtattc catatatggg ttttcctatt gacgtagata gcccctccca   1140
atgggcggtc ccatatacca tatatggggc ttcctaatac cgcccatagc cactccccca   1200
ttgacgtcaa tggtctctat atatggtctt tcctattgac gtcatatggg cggtcctatt   1260
gacgtatatg gcgcctcccc cattgacgtc aattacggta aatggcccgc ctggctcaat   1320
gcccattgac gtcaatagga ccacccacca ttgacgtcaa tgggatggct cattgcccat   1380
tcatatccgt tctcacgccc cctattgacg tcaatgacgg taaatggccc acttggcagt   1440
acatcaatat ctattaatag taacttggca agtacattac tattggaagt acgccagggt   1500
acattggcag tactcccatt gacgtcaatg gcggtaaatg gcccgcgatg gctgccaagt   1560
acatccccat tgacgtcaat ggggaggggc aatgacgcaa atgggcgttc cattgacgta   1620
aatgggcggt aggcgtgcct aatgggaggt ctatataagc aatgctcgtt tagggaaccg   1680
ccattctgcc tggggacgtc ggagcaagct agcttgcttg ttctttttgc agaagctcag   1740
aataaacgct caactttggc agatctgaat tcctgcagcc cgggggatcc acagccacca   1800
tgagtaaagg agaagaactt ttcactggag ttgtcccaat tcttgttgaa ttagatggtg   1860
atgttaatgg gtacaaattt tctgtcagtg gagagggtga aggtgatgca acatacggaa   1920
aacttaccct taaatttatt tgcactactg gaaaactacc tgttccatgg ccaacacttg   1980
tcactactct cacttatggt gttcaatgct tttcaagata tccagatcat atgaagcggc   2040
acgacttctt caagagcgcc atgcctgagg gatacgtgca ggagaggacc atcttcttca   2100
aggacgacgg gaactacaag acacgtgctg aagtcaagtt tgagggagac accctcgtca   2160
acaggatcga gcttaaggta agaaaagttc acatctgagt aggtagaata aaaagctgca   2220
tgccttcgtc gaccgttgac agtgagcgac ttgtcctctg caagtctctc tcccgtgaag   2280
ccacaaatgg ggagagagac taagaggtca agctgcctac tgcctaatgc atcttcacgc   2340
gtagcttccc ttaatacaag tgagatgatg gcataccatc tttcgggact gagttgatgt   2400
gaagagtttt tctgttttgc tgatcacttg tatattatgt gactaatagt taaagtgcca   2460
aaataaaatg tgggaacatt gaatgtgtat cctacttaag ggaatcgatt tcaaggagga   2520
cggaaacatc ctcggccaca agttggaata caactacaac tcccacaacg tatacatcat   2580
ggccgacaag caaaagaacg gcatcaaagc caacttcaag acccgccaca acatcgaaga   2640
cggcggcgtg caactcgctg atcattatca acaaaatact ccaattggcg atgaccctgt   2700
ccttttacca gacaaccatt acctgtccac acaatctgcc ctttcgaaag atcccaacga   2760
aaagagagac cacatggtcc ttcttgagtt tgtaacggct gctgggatta cacatggcat   2820
ggatgaacta tacaaaaatc tagaactata gtgagtcgta ttacgtagat ccagacatga   2880
taagatacat tgatgagttt ggacaaacca caactagaat gcagtgaaaa aaatgcttta   2940
tttgtgaaat ttgtgatgct attgctttat ttgtaaccat tataagctgc aataaacaag   3000
ttaacaacaa caattgcatt cattttatgt ttcaggttca gggggaggtg tgggaggttt   3060
tttaattcgc ggccgccacc gcggtggagc tccagctttt gttcccttta gtgagggtta   3120
```

-continued

```
attgcgcgca ttaccctgtt atccctacgc gcttggcgta atcatggtca tagctgtttc   3180

ctgtgtgaaa ttgttatccg ctcacaattc cacacaacat acgagccgga agcataaagt   3240

gtaaagcctg gggtgcctaa tgagtgagct aactcacatt aattgcgttg cgctcactgc   3300

ccgctttcca gtcgggaaac ctgtcgtgcc agctgcatta atgaatcggc caacgcgcgg   3360

ggagaggcgg tttgcgtatt gggcgctctt ccgcttcctc gctcactgac tcgctgcgct   3420

cggtcgttcg gctgcggcga gcggtatcag ctcactcaaa ggcggtaata cggttatcca   3480

cagaatcagg ggataacgca ggaaagaaca tgtgagcaaa aggccagcaa aaggccagga   3540

accgtaaaaa ggccgcgttg ctggcgtttt tccataggct ccgcccccct gacgagcatc   3600

acaaaaatcg acgctcaagt cagaggtggc gaaacccgac aggactataa agataccagg   3660

cgtttccccc tggaagctcc ctcgtgcgct ctcctgttcc gaccctgccg cttaccggat   3720

acctgtccgc ctttctccct tcgggaagcg tggcgctttc tcatagctca cgctgtaggt   3780

atctcagttc ggtgtaggtc gttcgctcca agctgggctg tgtgcacgaa ccccccgttc   3840

agcccgaccg ctgcgcctta tccggtaact atcgtcttga gtccaacccg gtaagacacg   3900

acttatcgcc actggcagca gccactggta acaggattag cagagcgagg tatgtaggcg   3960

gtgctacaga gttcttgaag tggtggccta actacggcta cactagaaga acagtatttg   4020

gtatctgcgc tctgctgaag ccagttacct tcggaaaaag agttggtagc tcttgatccg   4080

gcaaacaaac caccgctggt agcggtggtt tttttgtttg caagcagcag attacgcgca   4140

gaaaaaaagg atctcaagaa gatcctttga tcttttctac ggggtctgac gctcagtgga   4200

acgaaaactc acgttaaggg attttggtca tgagattatc aaaaaggatc ttcacctaga   4260

tccttttaaa ttaaaaatga agttttaaat caatctaaag tatatatgag taaacttggt   4320

ctgacagtta ccaatgctta atcagtgagg cacctatctc agcgatctgt ctatttcgtt   4380

catccatagt tgcctgactc cccgtcgtgt agataactac gatacgggag ggcttaccat   4440

ctggccccag tgctgcaatg ataccgcgag acccacgctc accggctcca gatttatcag   4500

caataaacca gccagccgga agggccgagc gcagaagtgg tcctgcaact ttatccgcct   4560

ccatccagtc tattaattgt tgccgggaag ctagagtaag tagttcgcca gttaatagtt   4620

tgcgcaacgt tgttgccatt gctacaggca tcgtggtgtc acgctcgtcg tttggtatgg   4680

cttcattcag ctccggttcc caacgatcaa ggcgagttac atgatccccc atgttgtgca   4740

aaaaagcggt tagctccttc ggtcctccga tcgttgtcag aagtaagttg gccgcagtgt   4800

tatcactcat ggttatggca gcactgcata attctcttac tgtcatgcca tccgtaagat   4860

gcttttctgt gactggtgag tactcaacca agtcattctg agaatagtgt atgcggcgac   4920

cgagttgctc ttgcccggcg tcaatacggg ataataccgc gccacatagc agaactttaa   4980

aagtgctcat cattggaaaa cgttcttcgg ggcgaaaact ctcaaggatc ttaccgctgt   5040

tgagatccag ttcgatgtaa cccactcgtg cacccaactg atcttcagca tcttttactt   5100

tcaccagcgt ttctgggtga gcaaaaacag gaaggcaaaa tgccgcaaaa aagggaataa   5160

gggcgacacg gaaatgttga atactcatac tcttcctttt tcaatattat tgaagcattt   5220

atcagggtta ttgtctcatg agcggataca tatttgaatg tatttagaaa aataaacaaa   5280

taggggttcc gcgcacattt ccccgaaaag tgccac                             5316
```

<210> SEQ ID NO 49
<211> LENGTH: 5316
<212> TYPE: DNA

<213> ORGANISM: Artificial
<220> FEATURE:
<223> OTHER INFORMATION: Plasmid GSH0_Nek2 OshR3

<400> SEQUENCE: 49
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgtagggat aacagggtaa tgcgcgcgta atacgactca 660
ctatagggcg aattgggtac cggccccccc ctcgaccata gccaattcaa tatggcgtat 720
atggactcat gccaattcaa tatggtggat ctggacctgt gccaattcaa tatggcgtat 780
atggactcgt gccaattcaa tatggtggat ctggacccca gccaattcaa tatggcggac 840
ttggcaccat gccaattcaa tatggcggac ttggcactgt gccaactggg gaggggtcta 900
cttggcacgg tgccaagttt gaggaggggt cttggccctg tgccaagtcc gccatattga 960
attggcatgg tgccaataat ggcggccata ttggctatat gccaggatca atatataggc 1020
aatatccaat atggccctat gccaatatgg ctattggcca ggttcaatac tatgtattgg 1080
ccctatgcca tatagtattc catatatggg ttttcctatt gacgtagata gcccctccca 1140
atgggcggtc ccatatacca tatatggggc ttcctaatac cgcccatagc cactccccca 1200
ttgacgtcaa tggtctctat atatggtctt tcctattgac gtcatatggg cggtcctatt 1260
gacgtatatg gcgcctcccc cattgacgtc aattacggta aatggcccgc ctggctcaat 1320
gcccattgac gtcaatagga ccacccacca ttgacgtcaa tgggatggct cattgcccat 1380
tcatatccgt tctcacgccc cctattgacg tcaatgacgg taaatggccc acttggcagt 1440
acatcaatat ctattaatag taacttggca agtacattac tattggaagt acgccagggt 1500
acattggcag tactcccatt gacgtcaatg gcggtaaatg gcccgcgatg gctgccaagt 1560
acatccccat tgacgtcaat ggggaggggc aatgacgcaa atgggcgttc cattgacgta 1620
aatgggcggt aggcgtgcct aatgggaggt ctatataagc aatgctcgtt tagggaaccg 1680
ccattctgcc tggggacgtc ggagcaagct agcttgcttg ttctttttgc agaagctcag 1740
aataaacgct caactttggc agatctgaat tcctgcagcc cgggggatcc acagccacca 1800
tgagtaaagg agaagaactt ttcactggag ttgtcccaat tcttgttgaa ttagatggtg 1860
atgttaatgg gtacaaattt tctgtcagtg gagagggtga aggtgatgca acatacggaa 1920
aacttaccct taaatttatt tgcactactg gaaaactacc tgttccatgg ccaacacttg 1980
tcactactct cacttatggt gttcaatgct tttcaagata tccagatcat atgaagcggc 2040
acgacttctt caagagcgcc atgcctgagg gatacgtgca ggagaggacc atcttcttca 2100
aggacgacgg gaactacaag acacgtgctg aagtcaagtt tgagggagac accctcgtca 2160
acaggatcga gcttaaggta agaaaagttc acatctgagt aggtagaata aaaagctgca 2220

-continued

```
tgccttcgtc gaccgttgac agtgagcgac ttcttcaggt ccctgcactt ggccgtgaag   2280
ccacaaatgg gccaagtgca gccctgatga agctgcctac tgcctaatgc atcttcacgc   2340
gtagcttccc ttaatacaag tgagatgatg gcataccatc tttcgggact gagttgatgt   2400
gaagagtttt tctgttttgc tgatcacttg tatattatgt gactaatagt taaagtgcca   2460
aaataaaatg tgggaacatt gaatgtgtat cctacttaag ggaatcgatt tcaaggagga   2520
cggaaacatc ctcggccaca agttggaata caactacaac tcccacaacg tatacatcat   2580
ggccgacaag caaaagaacg gcatcaaagc caacttcaag acccgccaca acatcgaaga   2640
cggcggcgtg caactcgctg atcattatca acaaaatact ccaattggcg atgaccctgt   2700
ccttttacca gacaaccatt acctgtccac acaatctgcc ctttcgaaag atcccaacga   2760
aaagagagac cacatggtcc ttcttgagtt tgtaacggct gctgggatta cacatggcat   2820
ggatgaacta tacaaaaatc tagaactata gtgagtcgta ttacgtagat ccagacatga   2880
taagatacat tgatgagttt ggacaaacca caactagaat gcagtgaaaa aaatgcttta   2940
tttgtgaaat ttgtgatgct attgctttat ttgtaaccat tataagctgc aataaacaag   3000
ttaacaacaa caattgcatt cattttatgt ttcaggttca gggggaggtg tgggaggttt   3060
tttaattcgc ggccgccacc gcggtggagc tccagctttt gttcccttta gtgagggtta   3120
attgcgcgca ttaccctgtt atccctacgc gcttggcgta atcatggtca tagctgtttc   3180
ctgtgtgaaa ttgttatccg ctcacaattc cacacaacat acgagccgga agcataaagt   3240
gtaaagcctg gggtgcctaa tgagtgagct aactcacatt aattgcgttg cgctcactgc   3300
ccgctttcca gtcgggaaac ctgtcgtgcc agctgcatta atgaatcggc caacgcgcgg   3360
ggagaggcgg tttgcgtatt gggcgctctt ccgcttcctc gctcactgac tcgctgcgct   3420
cggtcgttcg gctgcggcga gcggtatcag ctcactcaaa ggcggtaata cggttatcca   3480
cagaatcagg ggataacgca ggaaagaaca tgtgagcaaa aggccagcaa aaggccagga   3540
accgtaaaaa ggccgcgttg ctggcgtttt tccataggct ccgcccccct gacgagcatc   3600
acaaaaatcg acgctcaagt cagaggtggc gaaacccgac aggactataa agataccagg   3660
cgtttccccc tggaagctcc ctcgtgcgct ctcctgttcc gaccctgccg cttaccggat   3720
acctgtccgc ctttctccct tcgggaagcg tggcgctttc tcatagctca cgctgtaggt   3780
atctcagttc ggtgtaggtc gttcgctcca agctgggctg tgtgcacgaa ccccccgttc   3840
agcccgaccg ctgcgcctta tccggtaact atcgtcttga gtccaacccg gtaagacacg   3900
acttatcgcc actggcagca gccactggta acaggattag cagagcgagg tatgtaggcg   3960
gtgctacaga gttcttgaag tggtggccta actacggcta cactagaaga acagtatttg   4020
gtatctgcgc tctgctgaag ccagttacct tcggaaaaag agttggtagc tcttgatccg   4080
gcaaacaaac caccgctggt agcggtggtt tttttgtttg caagcagcag attacgcgca   4140
gaaaaaaagg atctcaagaa gatcctttga tcttttctac ggggtctgac gctcagtgga   4200
acgaaaactc acgttaaggg attttggtca tgagattatc aaaaaggatc ttcacctaga   4260
tccttttaaa ttaaaaatga agttttaaat caatctaaag tatatatgag taaacttggt   4320
ctgacagtta ccaatgctta atcagtgagg cacctatctc agcgatctgt ctatttcgtt   4380
catccatagt tgcctgactc cccgtcgtgt agataactac gatacgggag ggcttaccat   4440
ctggccccag tgctgcaatg ataccgcgag acccacgctc accggctcca gatttatcag   4500
caataaacca gccagccgga agggccgagc gcagaagtgg tcctgcaact ttatccgcct   4560
```

ccatccagtc tattaattgt tgccgggaag ctagagtaag tagttcgcca gttaatagtt 4620
tgcgcaacgt tgttgccatt gctacaggca tcgtggtgtc acgctcgtcg tttggtatgg 4680
cttcattcag ctccggttcc caacgatcaa ggcgagttac atgatccccc atgttgtgca 4740
aaaaagcggt tagctccttc ggtcctccga tcgttgtcag aagtaagttg gccgcagtgt 4800
tatcactcat ggttatggca gcactgcata attctcttac tgtcatgcca tccgtaagat 4860
gcttttctgt gactggtgag tactcaacca agtcattctg agaatagtgt atgcggcgac 4920
cgagttgctc ttgcccggcg tcaatacggg ataataccgc gccacatagc agaactttaa 4980
aagtgctcat cattggaaaa cgttcttcgg ggcgaaaact ctcaaggatc ttaccgctgt 5040
tgagatccag ttcgatgtaa cccactcgtg cacccaactg atcttcagca tcttttactt 5100
tcaccagcgt ttctgggtga gcaaaaacag gaaggcaaaa tgccgcaaaa aagggaataa 5160
gggcgacacg gaaatgttga atactcatac tcttcctttt tcaatattat tgaagcattt 5220
atcagggtta ttgtctcatg agcggataca tatttgaatg tatttagaaa aataaacaaa 5280
taggggttcc gcgcacattt ccccgaaaag tgccac 5316

<210> SEQ ID NO 50
<211> LENGTH: 1452
<212> TYPE: DNA
<213> ORGANISM: Artificial
<220> FEATURE:
<223> OTHER INFORMATION: Plasmid NEK2 wild type ORF with myc epitope

<400> SEQUENCE: 50
atggcatcaa tgcagaagct gatctcagag gaggacctgc ttatggccat ggaggcccga 60
attcggtcga ccgagatctc tcgaagcggc gcggtggtgt ggttgccagg gtggccgctc 120
gccatgccgt cccgggtgga ggactacgag gtgctgcaca gcatcggcac cggctcctac 180
ggccgctgtc agaagattcg gaggaagagc gacggcaaga tcctggtgtg gaaagagctt 240
gactatggct ccatgacgga ggtggagaag cagatgcttg tgtctgaagt gaacttgctt 300
cgggagctga aacatccaaa catcgtccgt tactatgatc gcattattga ccgaaccaac 360
acaaccctgt acatcgtaat ggaatactgt gagggagggg acctggctag tgtcatttca 420
aaggggacca aggatagaca gtacttggaa gaagagtttg tccttcgagt gatgactcag 480
ttgacgctgg ccctgaaaga gtgtcacaga aggagcgatg gtggccacac tgtgcttcac 540
cgggacctga agccagccaa tgtcttcctg gacagcaaac acaatgtcaa gctgggggac 600
tttggactag ctagaatatt aaatcacgac acgagttttg caaaaacgtt tgttggcaca 660
ccctattaca tgtctcctga acagatgagc tgcttatcct acaacgagaa gtcggacatc 720
tggtccttgg gctgcctgct gtatgagctg tgtgcactaa tgcctccctt tacagctttc 780
aaccaaaaag agctagctgg gaaaatcagg gaagggaggt tcaggcgcat cccctaccgc 840
tactctgatg gcttgaatga cctcatcact cggatgctga atttaaagga ctaccatcga 900
ccttcagtgg aagaaattct ggagagccct ttgatagcag acatggttgc agaagagcaa 960
aggagaaatc tggagaggag aggacggcgc tcaggcgagc cttcgaagct gccggactcc 1020
agccctgtgc tgagcgagct caagttgaag gaaaggcaac tgcaggatcg agagcaagca 1080
ctcagagctc gggaggacat tctggagcag aaggaacgtg aactttgtat tcgagagaga 1140
cttgcagagg acaaactggc cagagccgag agcctgatga agaactacag cctgctgaag 1200
gagcacaggc tcctatgtct ggctggtggc ccagaacttg atcttccatc ctcagccatg 1260
aagaagaagg ttcatttcca cggggaaagc aaagagaaca ccgcaaggag tgagaattct 1320
gagagctacc ttgccaagtc caagtgcagg gacctgaaga agaggcttca tgctgcccag 1380
ctgcgggctc aagccctggc tgatattgaa aaaaactacc agctaaagag caggcagatc 1440
ctgggcatgc gc 1452

<210> SEQ ID NO 51
<211> LENGTH: 1452
<212> TYPE: DNA
<213> ORGANISM: Artificial
<220> FEATURE:
<223> OTHER INFORMATION: Plasmid NEK2 OshR1 SDM

<400> SEQUENCE: 51
atggcatcaa tgcagaagct gatctcagag gaggacctgc ttatggccat ggaggcccga 60
attcggtcga ccgagatctc tcgaagcggc gcggtggtgt ggttgccagg gtggccgctc 120
gccatgccgt cccgggtgga ggactacgag gtgctgcaca gcatcggcac cggctcctac 180
ggccgctgtc agaagattcg gaggaagagc gacggcaaga tcctggtgtg gaaagagctt 240
gactatggct ccatgacgga ggtggagaag cagatgcttg tgtctgaagt gaacttgctt 300
cgggagctga aacatccaaa catcgtccgt tactatgatc gcattattga ccgaaccaac 360
acaaccctgt acatcgtaat ggaatactgt gagggagggg acctggctag tgtcatttca 420
aaggggacca aggatagaca gtacttggaa gaagagtttg tccttcgagt gatgactcag 480
ttgacgctgg ccctgaaaga gtgtcacaga aggagcgatg gtggccacac tgtgcttcac 540
cgggacctga agccagccaa tgtcttcctg gacagcaaac acaatgtcaa gctgggggac 600
tttggactag ctagaatatt aaatcacgac acgagttttg caaaaacgtt tgttggcaca 660
ccctattaca tgtctcctga acagatgagc tgcttatcct acaacgagaa gtcggacatc 720
tggtccttgg gctgcctgct gtatgagctg tgtgcactaa tgcctccctt tacagctttc 780
aaccaaaaag agctagctgg gaaaatcagg gaagggaggt tcaggcgcat cccctaccgc 840
tactctgatg gcttgaatga cctcatcact cggatgctga atttaaagga ctaccatcga 900
ccttcagtgg aggaaattct ggagagccct ttgatagcag acatggttgc agaagagcaa 960
aggagaaatc tggagaggag aggacggcgc tcaggcgagc cttcgaagct gccggactcc 1020
agccctgtgc tgagcgagct caagttgaag gaaaggcaac tgcaggatcg agagcaagca 1080
ctcagagctc gggaggacat tctggagcag aaggaacgtg aactttgtat tcgagagaga 1140
cttgcagagg acaaactggc cagagccgag agcctgatga agaactacag cctgctgaag 1200
gagcacaggc tcctatgtct ggctggtggc ccagaacttg atcttccatc ctcagccatg 1260
aagaagaagg ttcatttcca cggggaaagc aaagagaaca ccgcaaggag tgagaattct 1320
gagagctacc ttgccaagtc caagtgcagg gacctgaaga agaggcttca tgctgcccag 1380
ctgcgggctc aagccctggc tgatattgaa aaaaactacc agctaaagag caggcagatc 1440
ctgggcatgc gc 1452

<210> SEQ ID NO 52
<211> LENGTH: 1452
<212> TYPE: DNA
<213> ORGANISM: Artificial
<220> FEATURE:
<223> OTHER INFORMATION: Plasmid NEK2 OshR2 SDM

<400> SEQUENCE: 52
atggcatcaa tgcagaagct gatctcagag gaggacctgc ttatggccat ggaggcccga 60

```
attcggtcga ccgagatctc tcgaagcggc gcggtggtgt ggttgccagg gtggccgctc    120
gccatgccgt cccgggtgga ggactacgag gtgctgcaca gcatcggcac cggctcctac    180
ggccgctgtc agaagattcg gaggaagagc gacggcaaga tcctggtgtg gaaagagctt    240
gactatggct ccatgacgga ggtggagaag cagatgcttg tgtctgaagt gaacttgctt    300
cgggagctga aacatccaaa catcgtccgt tactatgatc gcattattga ccgaaccaac    360
acaaccctgt acatcgtaat ggaatactgt gagggagggg acctggctag tgtcatttca    420
aaggggacca aggatagaca gtacttggaa gaagagtttg tccttcgagt gatgactcag    480
ttgacgctgg ccctgaaaga gtgtcacaga aggagcgatg gtggccacac tgtgcttcac    540
cgggacctga agccagccaa tgtcttcctg gacagcaaac acaatgtcaa gctgggggac    600
tttggactag ctagaatatt aaatcacgac acgagttttg caaaaacgtt tgttggcaca    660
ccctattaca tgtctcctga acagatgagc tgcttatcct acaacgagaa gtcggacatc    720
tggtccttgg gctgcctgct gtatgagctg tgtgcactaa tgcctcccct tacagctttc    780
aaccaaaaag agctagctgg gaaaatcagg gaagggaggt tcaggcgcat cccctaccgc    840
tactctgatg gcttgaatga cctcatcact cggatgctga atttaaagga ctaccatcga    900
ccttcagtgg aagaaattct ggagagccct ttgatagcag acatggttgc agaagagcaa    960
aggagaaatc tggagaggag aggacggcgc tcaggcgagc cttcgaagct gccggactcc   1020
agccctgtgc tgagcgagct caagttgaag gaaaggcaac tgcaggatcg agagcaagca   1080
ctcagagctc gggaggacat tctggagcag aaggaacgtg aactttgtat tcgagagaga   1140
cttgccgagg acaaactggc cagagccgag agcctgatga agaactacag cctgctgaag   1200
gagcacaggc tcctatgtct ggctggtggc ccagaacttg atcttccatc ctcagccatg   1260
aagaagaagg ttcatttcca cggggaaagc aaagagaaca ccgcaaggag tgagaattct   1320
gagagctacc ttgccaagtc caagtgcagg gacctgaaga agaggcttca tgctgcccag   1380
ctgcgggctc aagccctggc tgatattgaa aaaaactacc agctaaagag caggcagatc   1440
ctgggcatgc gc                                                       1452
```

```
<210> SEQ ID NO 53
<211> LENGTH: 1452
<212> TYPE: DNA
<213> ORGANISM: Artificial
<220> FEATURE:
<223> OTHER INFORMATION: Plasmid NEK2 OshR3 SDM

<400> SEQUENCE: 53

atggcatcaa tgcagaagct gatctcagag gaggacctgc ttatggccat ggaggcccga     60
attcggtcga ccgagatctc tcgaagcggc gcggtggtgt ggttgccagg gtggccgctc    120
gccatgccgt cccgggtgga ggactacgag gtgctgcaca gcatcggcac cggctcctac    180
ggccgctgtc agaagattcg gaggaagagc gacggcaaga tcctggtgtg gaaagagctt    240
gactatggct ccatgacgga ggtggagaag cagatgcttg tgtctgaagt gaacttgctt    300
cgggagctga aacatccaaa catcgtccgt tactatgatc gcattattga ccgaaccaac    360
acaaccctgt acatcgtaat ggaatactgt gagggagggg acctggctag tgtcatttca    420
aaggggacca aggatagaca gtacttggaa gaagagtttg tccttcgagt gatgactcag    480
ttgacgctgg ccctgaaaga gtgtcacaga aggagcgatg gtggccacac tgtgcttcac    540
cgggacctga agccagccaa tgtcttcctg gacagcaaac acaatgtcaa gctgggggac    600
tttggactag ctagaatatt aaatcacgac acgagttttg caaaaacgtt tgttggcaca    660
```

-continued ccctattaca tgtctcctga acagatgagc tgcttatcct acaacgagaa gtcggacatc 720
tggtccttgg gctgcctgct gtatgagctg tgtgcactaa tgcctccctt tacagctttc 780
aaccaaaaag agctagctgg gaaaatcagg gaagggaggt tcaggcgcat cccctaccgc 840
tactctgatg gcttgaatga cctcatcact cggatgctga atttaaagga ctaccatcga 900
ccttcagtgg aagaaattct ggagagccct ttgatagcag acatggttgc agaagagcaa 960
aggagaaatc tggagaggag aggacggcgc tcaggcgagc cttcgaagct gccggactcc 1020
agccctgtgc tgagcgagct caagttgaag gaaaggcaac tgcaggatcg agagcaagca 1080
ctcagagctc gggaggacat tctggagcag aaggaacgtg aactttgtat tcgagagaga 1140
cttgcagagg acaaactggc cagagccgag agcctgatga agaactacag cctgctgaag 1200
gagcacaggc tcctatgtct ggctggtggc ccagaacttg atcttccatc ctcagccatg 1260
aagaagaagg ttcatttcca cggggaaagc aaagagaaca ccgcaaggag tgagaattct 1320
gagagctacc ttgccaaatc caagtgcagg gacctcaaga agaggcttca tgctgcccag 1380
ctgcgggctc aagccctggc tgatattgaa aaaaactacc agctaaagag caggcagatc 1440
ctgggcatgc gc 1452

<210> SEQ ID NO 54
<211> LENGTH: 16
<212> TYPE: DNA
<213> ORGANISM: Artificial
<220> FEATURE:
<223> OTHER INFORMATION: 3' constant stem derived from mouse and human miR-30a

<400> SEQUENCE: 54
gctgcctact gcctcc 16

<210> SEQ ID NO 55
<211> LENGTH: 15
<212> TYPE: DNA
<213> ORGANISM: Artificial
<220> FEATURE:
<223> OTHER INFORMATION: 3' constant stem derived from Xenopus miR-30a

<400> SEQUENCE: 55
gctgccaact gcctt 15

<210> SEQ ID NO 56
<211> LENGTH: 15
<212> TYPE: DNA
<213> ORGANISM: Artificial
<220> FEATURE:
<223> OTHER INFORMATION: 5' constant stem derived from mouse and human miR-30a

<400> SEQUENCE: 56
gttgacagtg agcga 15

<210> SEQ ID NO 57
<211> LENGTH: 15
<212> TYPE: DNA
<213> ORGANISM: Artificial
<220> FEATURE:
<223> OTHER INFORMATION: 5' constant stem derived from Xenopus miR-30a

<400> SEQUENCE: 57
ctgacagtat gcgac 15

-continued

<210> SEQ ID NO 58
<211> LENGTH: 19
<212> TYPE: DNA
<213> ORGANISM: Artificial
<220> FEATURE:
<223> OTHER INFORMATION: Constant loop derived from mouse and human miR-30a

<400> SEQUENCE: 58
ccgtgaagcc acaaatggg 19

<210> SEQ ID NO 59
<211> LENGTH: 19
<212> TYPE: DNA
<213> ORGANISM: Artificial
<220> FEATURE:
<223> OTHER INFORMATION: Constant loop derived from Xenopus miR-30a

<400> SEQUENCE: 59
ccgtgaagca gttgaaggg 19